US012180284B2

(12) United States Patent
Poma et al.

(10) Patent No.: US 12,180,284 B2

(45) Date of Patent: Dec. 31, 2024

(54) CLINICAL METHODS FOR USE OF A PD-L1-BINDING MOLECULE COMPRISING A SHIGA TOXIN EFFECTOR

(71) Applicant: Molecular Templates, Inc., Austin, TX (US)

(72) Inventors: Eric Poma, New York, NY (US); Erin Willert, Round Rock, TX (US); Hilario Ramos, Austin, TX (US); Jensing Liu, Round Rock, TX (US); Roger Waltzman, New York, NY (US)

(73) Assignee: Molecular Templates, Inc., Austin, TX (US)

( * ) Notice: Subject to any disclaimer, the term of this patent is extended or adjusted under 35 U.S.C. 154(b) by 14 days.

(21) Appl. No.: 17/553,333

(22) Filed: Dec. 16, 2021

(65) Prior Publication Data

US 2022/0195050 A1 Jun. 23, 2022

Related U.S. Application Data

(60) Provisional application No. 63/126,304, filed on Dec. 16, 2020.

(51) Int. Cl.

| | |
|---|---|
| ***C07K 16/28*** | (2006.01) |
| ***A61K 9/00*** | (2006.01) |
| ***A61K 31/7036*** | (2006.01) |
| ***A61K 35/74*** | (2015.01) |
| ***A61K 39/00*** | (2006.01) |
| ***A61K 45/06*** | (2006.01) |
| ***A61K 47/26*** | (2006.01) |
| ***A61P 35/00*** | (2006.01) |

(52) U.S. Cl.

CPC ........ *C07K 16/2827* (2013.01); *A61K 9/0019* (2013.01); *A61K 31/7036* (2013.01); *A61K 35/74* (2013.01); *A61K 45/06* (2013.01); *A61K 47/26* (2013.01); *A61P 35/00* (2018.01); *A61K 2039/505* (2013.01); *A61K 2039/545* (2013.01)

(58) Field of Classification Search

CPC .............. C07K 16/2827; A61K 9/0019; A61K 31/7036; A61K 35/74; A61K 45/06; A61K 47/26; A61K 2039/505; A61K 2039/545; A61P 35/00

See application file for complete search history.

(56) References Cited

U.S. PATENT DOCUMENTS

| | | | |
|---|---|---|---|
| 4,342,566 A | 8/1982 | Theofilopoulos et al. | |
| 4,704,692 A | 11/1987 | Ladner | |
| 4,816,567 A | 3/1989 | Cabilly et al. | |
| 7,635,757 B2 | 12/2009 | Freeman et al. | |
| 7,887,801 B2 | 2/2011 | Wels et al. | |
| 7,892,540 B2 | 2/2011 | Chen et al. | |
| 7,943,743 B2 | 5/2011 | Korman et al. | |
| 8,217,149 B2 | 7/2012 | Irving et al. | |
| 8,460,927 B2 | 6/2013 | Chen | |
| 8,530,637 B2 | 9/2013 | Wels et al. | |
| 8,552,154 B2 | 10/2013 | Freeman et al. | |
| 8,779,108 B2 | 7/2014 | Queva et al. | |
| 8,981,063 B2 | 3/2015 | Chen | |
| 9,102,727 B2 | 4/2015 | Freeman et al. | |
| 9,493,565 B2 | 11/2016 | Queva et al. | |
| 9,580,507 B2 | 2/2017 | Korman et al. | |
| 9,624,298 B2 | 4/2017 | Nastri et al. | |
| 9,920,123 B2 | 3/2018 | Irving et al. | |
| 10,501,538 B2 * | 12/2019 | Zhang | G01N 33/57426 |
| 10,815,469 B2 | 10/2020 | Poma et al. | |
| 11,078,298 B2 * | 8/2021 | Catania | A61P 9/10 |
| 11,136,395 B2 * | 10/2021 | Poma | C07K 16/2827 |
| 11,918,649 B2 | 3/2024 | Poma et al. | |
| 2002/0197695 A1 | 12/2002 | Glucksmann et al. | |
| 2004/0028685 A1 | 2/2004 | Kinch et al. | |
| 2006/0115832 A1 | 6/2006 | Hoon | |
| 2007/0298434 A1 | 12/2007 | Gariepy et al. | |
| 2009/0156417 A1 | 6/2009 | Gariepy et al. | |

(Continued)

FOREIGN PATENT DOCUMENTS

| | | |
|---|---|---|
| WO | WO 94/04679 A1 | 3/1994 |
| WO | WO 94/29348 A2 | 12/1994 |

(Continued)

OTHER PUBLICATIONS

European Medicines Agency (EMA) (Assessment Report, Jul. 2018, Committee for Medicinal Products for Human Use (CHMP) (Year: 2018).*

Yan et al., Squamous cell carcinoma—similarities and differences among anatomical sites, 2011, American Journal of Cancer Research, vol. 1, Issue 3, pp. 275-300 (Year: 2011).*

Villabona, HLA-A*02 and its Prognostic Traits in Cancer, 2016, Karolinska Institutet (Year: 2016).*

Medlineplus, PDL1 (Immunotherapy) Tests, 2019, retrieved from: https://medlineplus.gov/lab-tests/pdl1-immunotherapy-tests/#:~:text=A%20PD%2DL1%20test%20uses,of%20cancer%20treatment%20called%20immunotherapy (Year: 2019).*

Naucler et al., The emerging role of human cytomegalovirus infection in human carcinogenesis: a review of current evidence and potential therapeutic implications, 2019, Oncotarget, vol. 10, No. 42, pp. 4333-4347 (Year: 2019).*

(Continued)

*Primary Examiner* — Jeffrey Stucker
*Assistant Examiner* — Brittney E Donoghue
(74) *Attorney, Agent, or Firm* — COOLEY LLP

(57) ABSTRACT

The present disclosure relates to PD-L1-binding molecules comprising a Shiga toxin effector region, a PD-L1-binding region, and a T cell epitope, and pharmaceutical compositions thereof. The PD-L1 binding molecules and pharmaceutical compositions thereof have uses for selectively killing specific cells (e.g., PD-L1 positive tumor cells and/or immune cells), for selectively delivering cargos to specific cells (e.g., PD-L1 positive tumor cells or immune cells), and as therapeutics for treating or slowing the progression of cancer (e.g., non-small cell lung cancer or squamous cell carcinoma of the head and neck). The present disclosure also relates to clinical methods for use of the disclosed PD-L1 binding molecules for treating a subject in need thereof.

41 Claims, 27 Drawing Sheets

Specification includes a Sequence Listing.

(56) References Cited

U.S. PATENT DOCUMENTS

| | | | |
|---|---|---|---|
| 2010/0041074 A1 | 2/2010 | Kimura | |
| 2012/0178111 A1 | 7/2012 | Diamandis et al. | |
| 2013/0196928 A1 | 8/2013 | Gariepy et al. | |
| 2015/0259428 A1 | 9/2015 | Poma et al. | |
| 2016/0017784 A1 | 1/2016 | Kumar | |
| 2016/0069900 A1 | 3/2016 | Ayanoglu et al. | |
| 2016/0177284 A1 | 6/2016 | Poma et al. | |
| 2016/0376328 A1 | 12/2016 | Poma et al. | |
| 2017/0002016 A1 | 1/2017 | Shishido et al. | |
| 2017/0143814 A1 | 5/2017 | Poma et al. | |
| 2017/0275382 A1 | 9/2017 | Poma et al. | |
| 2017/0281764 A1 | 10/2017 | Tso et al. | |
| 2017/0283497 A1* | 10/2017 | Schiffer-Mannioui | C07K 14/7051 |
| 2018/0243432 A1 | 8/2018 | Poma et al. | |
| 2018/0258143 A1 | 9/2018 | Poma et al. | |
| 2018/0291359 A1 | 10/2018 | Poma et al. | |
| 2019/0083644 A1 | 3/2019 | Yoo et al. | |
| 2019/0153044 A1 | 5/2019 | Poma et al. | |
| 2021/0017284 A1 | 1/2021 | Shimkets et al. | |
| 2021/0079097 A1* | 3/2021 | Poma | C07K 16/2827 |
| 2021/0079098 A1 | 3/2021 | Poma et al. | |
| 2021/0324082 A1 | 10/2021 | Poma et al. | |
| 2022/0306700 A1 | 9/2022 | Poma et al. | |

FOREIGN PATENT DOCUMENTS

| | | |
|---|---|---|
| WO | WO 2007/005874 A2 | 1/2007 |
| WO | WO 2018/080812 A1 | 1/2007 |
| WO | WO 2008/097866 A2 | 8/2008 |
| WO | WO 2011/000054 A1 | 1/2011 |
| WO | WO 2014/164680 A1 | 10/2014 |
| WO | WO 2014/164693 A2 | 10/2014 |
| WO | WO 2015/113005 A1 | 7/2015 |
| WO | WO 2015/113007 A1 | 7/2015 |
| WO | WO 2015/138435 A1 | 9/2015 |
| WO | WO 2015/138452 A1 | 9/2015 |
| WO | WO 2015/191764 A1 | 12/2015 |
| WO | WO 2016/196344 A1 | 12/2016 |
| WO | WO 2017/019623 A2 | 2/2017 |
| WO | WO 2018/106895 A1 | 6/2018 |
| WO | WO 2018/140427 A1 | 8/2018 |
| WO | WO 2018/159615 A1 | 9/2018 |
| WO | WO 2018/162749 A1 | 9/2018 |
| WO | WO 2019/059400 A1 | 3/2019 |
| WO | WO 2019/183093 A1 | 9/2019 |
| WO | WO 2020/081493 A1 | 4/2020 |
| WO | WO 2020/154475 A1 | 7/2020 |
| WO | WO 2021/055816 A1 | 3/2021 |

OTHER PUBLICATIONS

U.S. Appl. No. 62/746,153, filed Oct. 16, 2018, Willert.

Abelson, A. K. et al., "No evidence of association between genetic variants of the PDCD1 ligands and SLE," Genes and Immunity, 8:69-74 (2007).

Akula, Y. T. et al., "TAM Receptor Tyrosine Kinases as Emerging Targets of Innate Immune Checkpoint Blockade for Cancer Therapy," Immunol Rev., 276(1):165-177 (2017); doi:doi:10.1111/imr.12522.

Al-Jaufy, A. Y. et al., "Cytotoxicity of a Shiga toxin A Subunit-CD4 Fusion Protein to Human Immunodeficiency Virus-Infected Cells," Infection and Immunity, 62(3):956-960 (1994).

Alpdogan, O. & Van Den Brink, M. R. M., "Immune Tolerance and Transplantation," Semin Oncol, 39:629-642 (2012).

Andorsky, D. J. et al., "Programmed Death Ligand 1 Is Expressed by Non-Hodgkin Lymphomas and Inhibits the Activity of Tumor-Associated T Cells," Clin Cancer Res, 17(13):4232-4244 (2011).

Antignani, A. & Fitzgerald, D., Immunotoxins: The Role of the Toxin, Toxins, 5:1486-1505 (2013).

Arrieta, O. et al., "Expression of PD-1/PD-L1 and PD-L2 in peripheral T-cells from non-small cell lung cancer patients," Oncotarget, 8(60):101994-102005 (2017).

Au, T. K. et al., "The plant ribosome inactivating proteins luffin and saporin are potent inhibitors of HIV-1 integrase," FEBS Letters, 471:169-172 (2000).

Bagga, S. et al., "The Cytotoxic Activity of Ribosome-inactivating Protein Saporin-6 Is Attributed to Its rRNA N-Glycosidase and Internucleosomal DNA Fragmentation Activities," The Journal of Biological Chemistry, 278(7):4813-4820 (2003).

Ballbach, M. et al., "Expression of checkpoint molecules on myeloid-derived suppressor cells," Immunology Letters, 192:1-6 (2017).

Barbieri, L. et al., "Polynucleotide: adenosine glycosidase activity of ribosome-inactivating proteins: effect on DNA, RNA and poly(A)," Nucleic Acids Research, 25(3):518-522 (1997).

Barbieri, L. et al., "Polynucleotide: adenosine glycosidase activity of saporin-L1: effect on various forms of mammalian DNA," Biochimica et Biophysica Acta, 1480:258-266 (2000).

Barbieri, L. et al., "Polynucleotide: Adenosine Glycosidase Is the Sole Activity of Ribosome-Inactivating Proteins on DNA," J. Biochem, 128:883-889 (2000).

Barbieri, L. et al., "Polynucleotide: adenosine glycosidase activity of saporin-L1: effect on DNA, RNA and poly(A)," Biochem. J., 319:507-513 (1996).

Barbieri, L. et al., "Some ribosome-inactivating proteins depurinate ribosomal RNA at multiple sites," Biochem. J., 286:1-4 (1992).

Barbieri, L. et al., "Unexpected activity of saporins," Nature, 372:624 (1994).

Bielaszewska, M. et al., "Shiga Toxin Gene Loss and Transfer In Vitro and In Vivo during Enterohemorrhagic *Escherichia coli* O26 Infection in Humans," Applied and Environmental Microbiology, 73(10):3144-3150 (2007).

Bocanegra, A. et al., "PD-L1 Expression in Systemic Immune Cell Populations as a Potential Predictive Biomarker of Responses to PD-L1/PD-1 Blockade Therapy in Lung Cancer," Int. J. Mol. Sci., 20:1631 (2019); doi.10.3390/http://dx.doi.org/10.3390/ijms20071631, 13 pages.

Burgess, B. J. et al., "Proteolytic cleavage at arginine residues within the hydrophilic disulphide loop of the *Escherichia coli* Shiga-like toxin I A subunit is not essential for cytotoxicity," Molecular Microbiology, 10(1):171-179 (1993).

Bräunlein, E. & Krackhardt, A. M., "Identification and Characterization of Neoantigens As Well As Respective Immune Responses in Cancer Patients," Frontiers in Immunology, 8:1702 (2017), 8 pages.

Brieschke, B. et al., Abstract 4912, "Antigen Seeding Technology by Engineered Toxin Bodies Provides a Targeted Immuno-Oncology Approach for Treatment of Cancers," Molecular Templates, AACR Annual Meeting 2018; Apr. 14-18, 2018; Chicago, IL, 2018, 2 pages, with Poster.

Brieschke, B. et al., Abstract P804, "In vivo efficacy of a PD-L1 targeted Engineered Toxin Body (ETB) comprised of direct cytotoxicity and T-cell mediated tumor targeting," Molecular Templates, SITC 2019, Poster, 1 page.

Brieschke, B. et al., "In vivo efficacy of a PD-L1 targeted Engineered Toxin Body (ETB) comprised of direct cytotoxicity and T-cell mediated tumor targeting," Journal for ImmunoTherapy of Cancer, 7(Suppl 1):P804 (2019), 2 pages.

Brieschke, B. et al., Abstract 12, "PD-L1 targeted engineered toxin body provides directed cytotoxicity and T-cell mediated tumor targeting," 2020 ASCO-SITC Clinical Immuno-Oncology Symposium, 1 page.

Brieschke, B. et al., "P9 Identification and functional profiling of PD-L1 targeted engineered toxin bodies for antigen seeding technology and redirection of T cell response to tumors," Journal for Immunotherapy of Cancer, 6(Suppl 1):114, p. 5 (2018).

Brigotti, M. et al., "Damage to nuclear DNA induced by Shiga toxin 1 and ricin in human endothelial cells," The FASEB Journal, 16:365-372 (2002).

Brigotti, M. et al., "Shiga toxin 1: damage to DNA in vitro," Toxicon, 39:341-348 (2001).

Brigotti, M. et al, "The RNA-N-Glycosidase Activity of Shiga-like Toxin 1: Kinetic Parameters of the Native and Activated Toxin," Toxicon, 35(9):1431-1437 (1997).

(56) References Cited

OTHER PUBLICATIONS

Brown, J. A. et al., "Blockade of Programmed Death-1 Ligands on Dendritic Cells Enhances T Cell Activation and Cytokine Production," The Journal of Immunology, 170:1257-1266 (2003).
Butte, M. J. et al., "Programmed Death-1 Ligand 1 Interacts Specifically with the B7-1 Costimulatory Molecule to Inhibit T Cell Responses," Immunity, 27:111-122 (2007).
Cao, Y. et al., "Construction and characterization of novel, recombinant immunotoxins targeting the Her2/neu oncogene product: in vitro and in vivo studies," Cancer Research, 69(23): 8987-8995 (2009).
Cao, C. et al., "Construction of Mutant Genes for a Non-Toxic Verotoxin 2 Variant (VT2vp1 of *Escherichia coli* and Characterization of Purified Mutant Toxins," Microbiol. Immunol., 38(6):441-447 (1994).
Carreras-Sangrà, N. et al., "Production and characterization of a colon cancer-specific immunotoxin based on the fungal ribotoxin α-sarcin," Protein Engineering, Design & Selection, 25(8):425-435 (2012).
Chatterjee, S. et al., "Noninvasive Imaging of Immune Checkpoint Ligand PD-L1 in Tumors and Metastases for Guiding Immunotherapy," Molecular Imaging, 16:1-5 (2017).
Chen, L. & Han, X., "Anti-PD-1/PD-L1 therapy of human cancer: past, present, and future," J Clin Invest., 125(9):3384-3391 (2015); https://doi.org/10.1172/JCI80011.
Chen, L., "Co-Inhibitory Molecules of the B7-CD28 Family in the Control of T-cell Immunity," Nature, Nature Reviews Immunology, 4:336-347 (2004).
Chen, J. et al., "Interferon-γ-induced PD-L1 surface expression on human oral squamous carcinoma via PKD2 signal pathway," Immunobiology, 217:385-393 (2012).
Chen, B. J. et al., "PD-L1 Expression Is Characteristic of a Subset of Aggressive B-cell Lymphomas and Virus-Associated Malignancies," Clin Cancer Res, 19(13):3462-3473 (2013).
Chen, L. et al., "PD-L1 Expression Promotes Epithelial to Mesenchymal Transition in Human Esophageal Cancer," Cell Physiol biochem, 42:2267-2280 (2017); doi:10.1159/000480000 Published online: Aug. 17, 2017.
Chen, M.-F. et al., "The role of PD-L1 in the radiation response and prognosis for esophageal squamous cell carcinoma related to IL-6 and T-cell immunosuppression," Oncotarget, 7(7):7913-7924 (2016).
Cheung, M. C. et al., "An evolved ribo-inactivating protein targets and kills human melanoma cells in vitro and in vivo," Molecular Cancer, 9(28):1-14 (2010).
Darvin, P. et al., "Immune checkpoint inhibitors: recent progress and potential biomarkers," Experimental & Molecular Medicine, 50:165 (2018), https://doi.org/10.1038/s12276-018-0191-1, 11 pages.
Das, S. et al., "Immune-related adverse events and antitumor efficacy of immune checkpoint inhibitors," Journal for ImmunoTherapy of Cancer, 7:306 (2019), 11 pages.
De Lorenzo, C. & D'Alessio, G., "From ImmunoToxins to ImmunoRNases," Current Pharmaceutical Biotechnology, 9:210-214 (2008).
De Lorenzo, C. et al., "Intracellular route and mechanism of action of ERB-hRNase, a human anti-Erb2 anticancer immunoagent," FEBS Letters, 581:296-300 (2007).
De Sousa Linhares, A. et al., "Therapeutic PD-L1 antibodies are more effective than PD-1 antibodies in blocking PD-1/PD-L1 signaling," Scientific Reports, 9:11472 (2019), 9 pages; https://doi.org/10.1038/s41598-019-47910-1.
De Virgilio, M. et al., "Ribosome-Inactivating Proteins: From Plant Defense to Tumor Attack," Toxins, 2:2699-2737 (2010); doi:10.3390/toxins2112699.
Dekker, J. D. et al., Abstract 1791, "Engineered toxin bodies delivering immunogenic MHC class I peptides to tumor cells summon polyfunctional and relevant CTL responses against cancers," Molecular Templates, AAI 2019, 2 pages.
Deng, R. et al., "B7H1/CD80 Interaction Augments PD-1-Dependent T Cell Apoptosis and Ameliorates Graft-versus-Host Disease," The Journal of Immunology, 194:560-574 (2015).
Deresiewicz, R. L. et al., "Mutations Affecting the Activity of the Shiga-like Toxin I A-Chain," Biochemistry, 31(12):3272-3280 (1992).
Deresiewicz, R. L. et al., "The role of tyrosine-114 in the enzymatic activity of the Shiga-like toxin I A-chain," Mol. Gen. Genet., 241:467-473 (1993).
Déret, S. et al., "SUBIM: a program for analysing the Kabat database and determining the variability subgroup of a new immunoglobulin sequence," Cabios, 11(4):435-439 (1995).
Dermer, G. B., "Another Anniversary for the War on Cancer," Bio/Technology 12:320 (1994).
Dhanda, S. K. et al., "IEDB-AR: Immune epitope database—analysis resource in 2019," Nucleic Acids Research, 47:W502-W506 (2019).
Di, R. et al., "Identification of amino acids critical for the cytotoxicity of Shiga toxin 1 and 2 in *Saccharomyces cerevisiae*," Toxicon, 57(4):525-539 (2011).
Dong, H. et al., "B7-H1, a third member of the B7 family, co-stimulates T-cell proliferation and interleukin-10 secretion," Nature Medicine, 5(12):1365-1369 (1999).
Dong, H. et al., "Tumor-associated B7—H1 promotes T-cell apoptosis: A potential mechanism of immune evasion," Nature Medicine, 8(8):793-800 (2002).
Engedal, N. et al., "Shiga toxin and its use in targeted cancer therapy and imaging," Microbial Biotechnology, 4(1):32-46 (2011).
Erice, A. et al., "Anti-Human Immunodeficiency Virus Type 1 Activity of an Anti-CD4 Immunoconjugate Containing Pokeweed Antiviral Protein," Antimicrobial Agents and Chemotherapy, 37(4):835-838 (1993).
Flies, D. B. et al., "Blockade of the B7—H1/DP-1 Pathway for Cancer Immunotherapy," Yale Journal of Biology and Medicine, 84:409-421 (2011).
Foss, F. M. et al., "Diphtheria Toxin Fusion Proteins," Clinical Applications of Immunotoxins, 234:63-81 (1998).
Fracasso, G. et al., "Ribosome-Inactivating Protein-Containing Conjugates for Therapeutic Use," Toxic Plant Proteins, Plant Cell Monographs, 18:225-263, J. M. Lord and M. R. Hartley (eds.) (2010).
Freeman, G. J. et al., "Engagement of the PD-1 Immunoinhibitory Receptor by a Novel B7 Family Member Leads to Negative Regulation of Lymphocyte Activation," J. Exp. Med., 192(7):1027-1034 (2000).
Fuenmayor, J. & Montaño, R. F., "Novel Antibody-Based Proteins for Cancer Immunotherapy," Cancers, 3:33370-3393 (2011); doi:10.3390/cancers3033370.
Gabrilovich, D. I., "Myeloid-derived suppressor cells," Cancer Immunol Res, 5(1):3-8 (2017); doi: 10.1158/2326-6066.CIR-16-0297.
Gato-Cañas, M. et al., "PDL1 Signals through Conserved Sequence Motifs to Overcome Interferon-Mediated Cytotoxicity," Cell Reports, 20:1818-1829 (2017).
Ge, X. et al., "Cancer Immunotherapies Targeting Tumor-Associated Regulatory T Cells," Oncotargets and Therapy, 12:11033-11044 (2019).
GenBank Accession No. AAI13735.1, CD274 molecule [*Homo sapiens*], Jun. 29, 2006, 2 pages.
Gielis, S. et al., "Detection of Enriched T Cell Epitope Specificity in Full T Cell Receptor Sequence Repertoires," Frontiers in Immunology, vol. 10, Article 2820, pp. 1-2 (2019).
Glockshuber, R. et al., "A comparison of strategies to stabilize immunoglobulin Fv-fragments," Biochemistry, 29(6):1362-1367 (1990); doi: 10.1021/bi00458a002.
González-Escalona, N. & Kase, J. A., "Virulence gene profiles and phylogeny of Shiga toxin-positive *Escherichia coli* strains isolated from FDA regulated foods during 2010-2017," PLoS One, 14(4):e0214620 (2019), https://doi.org/10.1371/journal.pone.0214620, 26 pages.
Grotiuz, G. et al., "Shiga Toxin-2 Producing *Acinetobacter haemolyticus* Associated with a Case of Bloody Diarrhea," Journal of Clinical Microbiology, 44(10):3838-3841 (2006).
Grotzke, J. E. et al., "The ongoing saga of the mechanism(s) of MHC class I-restricted cross-presentation," Current Opinion in Immunology, 46:89-96 (2017).

(56) References Cited

OTHER PUBLICATIONS

Haddad, J. E. et al., "Minimum Domain of the Shiga Toxin A subunit Required for Enzymatic Activity," Journal of Bacteriology, 175(16):4970-4978 (1993).
Haeryfar, S. M. M. & Schell, T. D., "PD-1/PD-L1 co-inhibition shapes anticancer T cell immunodominance: facing the consequences of an immunological ménage à trois," Cancer Immunology, Immunotherapy, 67:1669-1672 (2018).
Hartley, G. P. et al., "Programmed Cell Death Ligand 1 (PD-L1) Signaling Regulates Macrophage Proliferation and Activation," Cancer Immunol Res, 6(10):1260-1273 (2018).
Hayashi, M. et al., "Association of an A/C single nucleotide polymorphism in programmed cell death-ligand 1 gene with Graves' disease in Japanese patients," European Journal of Endocrinology, 158:817-822 (2008).
Head, S. C. et al., "Preparation of VT1 and VT2 Hybrid Toxins from Their Purified Dissociated Subunits," The Journal of Biological Chemistry, 266(6):3617-3621 (1991).
Henson, S. M. & Akbar, A. N., KLRG1—more than a marker for T cell senescence, AGE, 31:285-291 (2009).
Hegde, N. R. et al., "The use of databases, data mining and immunoinformatics in vaccinology: where are we?" Expert Opinion on Drug Discovery, 13(2):117-130 (2018).
Hirano, F. et al., "Blockade of B7—H1 and PD-1 by Monoclonal Antibodies Potentiates Cancer Therapeutic Immunity," Cancer Res, 65(3):1089-1096 (2005).
Hovde, C. J. et al., "Evidence that glutamic acid 167 is an active-site residue of Shiga-like toxin-I," Proceedings of the National Academy of Sciences of the United States of America, 85(8):2568-2572 (1988).
Ilié, M. et al., "Detection of PD-L1 in circulating tumor cells and white blood cells from patients with advanced non-small-cell lung cancer," Annals of Oncology, 29:193-199 (2018).
Ishida, Y. et al., "Induced expression of PD-1, a novel member of the immunoglobulin gene superfamily, upon programmed cell death," The EMBO Journal, 11(11):3887-3895 (1992).
Jalali, S. et al., "Reverse signaling via PD-L1 supports malignant cell growth and survival in classical Hodgkin lymphoma," Blood Cancer Journal, 9:22 (2019), https://doi.org/10.1038/s41408-019-0185-9, 9 pages.
Ji, C. et al., "Myocarditis in Cynomolgus Monkeys Following Treatment with Immune Checkpoint Inhibitors," Clin Cancer Res., 25:4735-4748 (2019).
Johannes, L. & Römer, W., "Shiga Toxins—from cell biology to biomedical applications," Nature Reviews Microbiology, 8:105-116 (2010).
Khalil, R. K. S. et al., "Phage-mediated Shiga toxin (Stx) horizontal gene transfer and expression in non-Shiga toxigenic *Enterobacter* and *Escherichia coli* strains," Pathogens and Disease, 74(5):ftw037 (2016); doi:10.1093/femspd/ftw037, 11 pages.
Kar, P. et al., "Current methods for the prediction of T-cell epitopes," Peptide Science, 110:e24046 (2018); https://doi.org/10.1002/pep2.24046, 17 pages.
Karwacz, K. et al., "PD-L1 co-stimulation contributes to ligand-induced T cell receptor down-modulation on CD8+T cells," EMBO Mol Med, 3:581-592 (2011).
Kehry, M. et al., "W. 73—Discovery of Checkpoint Agonist Antibodies for Autoimmune/ Inflammatory Disease," General Autoimmunity Poster, W. 73 FOCiS Annual Meeting, Jun. 19, 2019, 3 pages.
Kowanetz, M. et al., "Differential regulation of PD-L1 expression by immune and tumor cells in NSCLC and the response to treatment with atezolizumab (anti-PD-L1)," PNAS, 115(43):e10119-e10126 (2018).
Lacadena, J. et al., "Fungal ribotoxins: molecular dissection of a family of natural killers," FEMS, 31:212-237 (2007).
Lakhrif, Z. et al., "A method to confer protein L binding ability to any antibody fragment," MAbs, 8(2):379-388 (2016).
Lapadula, W. J. et al., "Revising the Taxonomic Distribution, Origin and Evolution of Ribosome Inactivating Protein Genes," PLoS One, 8(9):e72825 (2013); doi:10.1371/journal.pone.0072825, 8 pages.
Lapointe, P. et al., "A Role for the Protease-sensitive Loop Region of Shiga-like Toxin 1 in the Retrotranslocation of its A Domain from the Endoplasmic Reticulum Lumen," Journal of Biological Chemistry, 280(24):23310-23318 (2005).
Latchman, Y. et al., "PD-L2 is a second ligand for PD-1 and inhibits T cell activation," Nature Immunology, 2(3):261-268 (2001).
Lau, J. et al., "Tumour and host cell PD-L1 is required to mediate suppression of anti-tumour immunity in mice," Nature Communications, 8:14572 (2017); doi:10.1038/ncomms14572, 11 pages.
Lea, N. et al., "Proteolytic cleavage of the A subunit is essential for maximal cytotoxicity of *Escherichia coli* O157:h7 Shiga-like toxin-1," Microbiology, 145(5):999-1004 (1999).
Lecis, D. et al., "Immune Checkpoint Ligand Reverse Signaling: Looking Back to Go Forward in Cancer Therapy," Cancers, 11:624 (2019); doi:10.3390/cancers11050624, 13 pages.
Lee, H. T. et al., "Molecular mechanism of PD-1/PD-L1 blockade via anti-PD-L1 antibodies atezolizumab and durvalumab," Scientific Reports, 7(1):5532 (2017), 12 pages; doi:10.1038/s41598-017-06002-8.
Lee, H. T. et al., "Molecular Interactions of Antibody Drugs Targeting PD-1, PD-L1, and CTLA-4 in Immuno-Oncology," Molecules, 24:1190 (2019); http://dx.doi.org/10.3390/molecules24061190, 16 pages.
Li, Y. et al., "Correction to: Discovery and preclinical characterization of the antagonist anti-PD-L1 monoclonal antibody LY3300054," Journal for Immuno Therapy of Cancer, vol. 6, No. 1, Jun. 2018, p. 1.
Lin, H. et al., "Selection and Characterization of Human Anti-MAGE-A1 scFv and Immunotoxin," Anti-Cancer Agents in Medicinal Chemistry, 13:1259-1266 (2013).
Ling, J. et al., "Cleavage of supercoiled double-stranded DNA by several ribosome-inactivating proteins in vitro," FEBS Letters, 345:143-146 (1994).
Lu, C. et al., "The expression profiles and regulation of PD-L1 in tumor-induced myeloid-derived suppressor cells," Oncoimmunology, 5(12):e1247135 (2016), 13 pages; http://dx.doi.org/10.1080/2162402X.2016.1247135.
Lu, C. et al., "Current perspectives on the immunosuppressive tumor microenvironment in hepatocellular carcinoma: challenges and opportunities," Molecular Cancer, 18:130 (2019); https://doi.org/10.1186/s12943-019-1047-6, 12 pages.
Lyu, M.-A. et al., "Cell Targeting Fusion Constructs Containing Recombinant Gelonin," Chapter 8: Methods in Immunology, 502:167-214 (2012).
Ma, W. et al., "Current status and perspectives in translational biomarker research for PD-1/PD-L1 immune checkpoint blockade therapy," Journal of Hematology & Oncology, 9:47 (2016); doi:10.1186/s13045-016-0277-y.
Ma, Y. et al., "Polymorphisms of co-inhibitory molecules (CTLA-4/PD-1/PD-L1) and the risk of non-small cell lung cancer in a Chinese population," Int J Clin Exp Med, 8(9):16585-16591 (2015).
McCluskey et al., "Charged and hydrophobic Surfaces on the A chain of Shiga-like Toxin 1 recognize the C-terminal Domain of Ribosomal Stalk Proteins," PLoS One 7(2):e31191 (2012).
Meeting Abstracts, "33rd Annual Meeting & Pre-Conference Programs of the Society for Immunotherapy of Cancer (SITC 2018)," Washington, D.C., USA, Nov. 7-11, 2018, Journal for ImmunoTherapy of Cancer, vol. 6, Supplement No. 1, Nov. 2018, pp. 1-205.
Meeting Abstracts, "34th Annual Meeting & Pre-Conference Programs of the Society for Immunotherapy of Cancer (SITC 2019): Part 2: National Harbor, MD, USA, Nov. 10, 2019," Journal for ImmunoTherapy of Cancer, vol. 7, Supplement No. 1, Nov. 2019, pp. 1-237, Abstract P804.
Memarnejadian, A. et al., "PD-1 Blockade Promotes Epitope Spreading in Anticancer CD8+ T Cell Responses by Preventing Fratricidal Death of Subdominant Clones to Relieve Immunodomination," The Journal of Immunology, 199:3348-3359 (2017).
Menzel, C. et al., "Human antibody RNase fusion protein targeting CD30+ lymphomas," Blood, 111:3830-3837 (2008).

(56) References Cited

OTHER PUBLICATIONS

Mitchell, A. L. et al., "Programmed Death Ligand 1 (PD-L1) Gene Variants Contribute to Autoimmune Addison's Disease and Graves' Disease Susceptibility," J Clin Endocrinol Metab, 94:5139-5145 (2009).
Moise, L. et al., "T cell epitope engineering: an avian H7N9 influenza vaccine strategy for pandemic preparedness and response," Human Vaccines & Immunotherapeutics, 14(9):2203-2207 (2018).
Molecular Templates, Molecular Templates Provides Corporate Update and Outlines 2020 Milestones, Jan. 8, 2020, 2 pages.
Molecular Templates, "New Data on Molecular Templates' Engineered Toxin Bodies to be Presented at the American Association of Cancer Research (AACR) Annual Meeting 2019," Feb. 27, 2019, 2 pages.
Molecular Templates, "Study on Molecular Templates' PD-L1 ETB with Antigen Seeding Technology Presented at SITC Annual Meeting," Nov. 9, 2018, 1 page.
Molecular Templates Inc.: R&D Day, Conference Call Transcript (Nov. 15, 2019) Fair Disclosure Wire, pp. 1-17; retrieved on Jan. 15, 2021 from https://dialog.proquest.com/professional/docview/2320577373, 17 pages.
Molecular Templates Corporate Presentation, Nov. 2019, 26 pages.
Nilson, B. H. K. et al., "Protein L from Peptostreptococcus magnus binds to the kappa light chain variable domain," Journal of Biological Chemistry, 267(4):2234-2239 (1992).
Nilson, B. H. K. et al., "Purification of antibodies using protein L-binding framework structures in the light chain variable domain," Journal of Immunological Methods, 164(1):33-40 (1993).
Muzard, J. et al., "Grafting of protein L-binding activity onto recombinant antibody fragments," Analytical Biochemistry, 388:331-338 (2009).
Myers, K. V. et al., "Targeting Tyro3, Axl and MerTK (TAM receptors): implications for macrophages in the tumor microenvironment," Molecular Cancer, 18:94 (2019); https://doi.org/10.1186/s12943-019-1022-2, 14 pages.
Nakamura, Y., "Biomarkers for Immune Checkpoint Inhibitor-Mediated Tumor Response and Adverse Events," Frontiers in Medicine, vol. 6, Article 119 (May 2019), 18 pages.
Newland, J. W. et al., "Cloning of Genes for Production of *Escherichia coli* Shiga-Like Toxin Type II," Infection and Immunity, 55(11):2675-2680 (1987).
Newton, D. L. et al., "Potent and specific antitumor effects of an anti-CD22-targeted cytotoxic ribonuclease: potential for the treatment of non-Hodgkin lymphoma," Blood, 97:528-535 (2001).
Nomi, T. et al., "Clinical Significance and Therapeutic Potential of the Programmed Death-1 Ligand/programmed Death-1 Pathway in Human Pancreatic Cancer," Clin Cancer Res, 13(7):2151-2157 (2007).
O'Brien, A. D. et al., "Shiga Toxin: Biochemistry, Genetics, Mode of Action, and Role in Pathogenesis," Current Topics in Microbiology and Immunology, 180:65-94 (1992).
Ogishi, M. & Yotsuyanagi, H., "Quantitative Prediction of the Landscape of T Cell Epitope Immunogenicity in Sequence Space," Frontiers in Immunology, vol. 10, Article 827, 2019, pp. 1-20.
Ohmura, M. et al., "Characterization of non-toxic mutant toxins of Vero toxin I that were constructed by replacing amino acids in the A subunit," Microbial Pathogenesis, 15(3):169-176 (1993).
Olsnes, S., "The history of ricin, abrin and related toxins," Toxicon, 44:361-370 (2004).
Park, J.-J. et al., "B7-H1/CD80 interaction is required for the induction and maintenance of peripheral T-cell tolerance," Blood, 116(8): 1291-1298 (2010).
Parikh, B. A. & Tumer, N. E., "Antiviral Activity Of Ribosome Inactivating Proteins In Medicine," Mini-Reviews in Medicinal Chemistry, 4:523-543 (2004).
Pastan, I. et al., "Immunotoxin therapy of cancer," Nature Reviews Cancer, 6:559-565 (2006).
Pastan, I. et al., "Recombinant toxins as novel therapeutic agents," Annu. Rev. Biochem., 61:331-354 (1992).
Picard, D. et al., "Pokeweed Antiviral Protein Inhibits Brome Mosaic Virus Replication in Plant Cells," The Journal of Biological Chemistry, 280(20):20069-20075 (2005).
Pillai, R. N. et al., "Comparison of the Toxicity Profile of PD-1 Versus PD-L1 Inhibitors in Non-Small Cell Lung Cancer: A Systematic Analysis of the Literature," Cancer, 124:271-277 (2018).
Polito, L. et al., "Saporin-S6: A Useful Tool in Cancer Therapy," Toxins, 5:1698-1722 (2013).
Press Release Molecular Templates' Presentations at the American Association of Cancer Research (AACR) Annual Meeting 2019 Highlight Evolution of ETB Platform, Apr. 2, 2019, 3 pages.
Press Release New Data on Molecular Templates' Engineered Toxin Bodies to be Presented at the American Association of Cancer Research (AACR) Annual Meeting 2019, Feb. 27, 2019, 4 pages.
Press Release Molecular Templates Announces FDA Acceptance of IND Application for MT-5111, An Engineered Toxin Body Targeting HER2, Austin Texas, Apr. 22, 2019, 2 pages.
Press Release Molecular Templates Provides Corporate Update and Outlines 2022 Milestones, Austin, Texas, Nov. 30, 2021, 6 pages.
Prima, V. et al., "COX2/mPGES1/PGE2 pathway regulates PD-L1 expression in tumor-associated macrophages and myeloid-derived suppressor cells," PNAS, 114(5):1117-1122 (2017).
Probert, W. S. et al., "Isolation and Identification of an *Enterobacter cloacae* Strain Producing a Novel Subtype of Shiga Toxin Type 1," Journal of Clinical Microbiology, 52(7):2346-2351 (2014).
Puri, M. et al., "Ribosome-inactivating proteins: current status and biomedical applications," Drug Discovery Today, 17(13-14):774-783 (2012).
Rajagopalan, S. et al., "Abstract 595: Next-generation engineered toxin bodies:CD38, PD-L1 and HER2 targeted ETBs," In: Proceedings of the 107th Annual Meeting of the American Association for Cancer Research; Apr. 16-20, 2016; New Orleans, LA. Philadelphia (PA): AACR; Cancer Res 2016;76(14 Suppl):Abstract nr 595, 2 pages.
Ribas, A. & Wolchok, J. D., "Cancer immunotherapy using checkpoint blockade," Science, 359:1350-1355 (2018).
Roncuzzi, L. & Gasperi-Campani, A., "DNA-nuclease activity of the single-chain ribosome-inactivating proteins dianthin 30, saporin 6 and gelonin," FEBS Letters, 392:16-20 (1996).
Saha, A. et al., "Host programmed death ligand 1 is dominant over programmed death ligand 2 expression in regulating graft-versus-host disease lethality," Blood, 122(17):3062-3073 (2013).
Scheutz, F. et al., "Multicenter Evaluation of a Sequence-Based Protocol for Subtyping Shiga Toxins and Standardizing Stx Nomenclature," Journal of Clinical Microbiology, 50(9):2951-2963 (2012).
Schumacher, F.-R. et al., "Building proteomic tool boxes to monitor MHC class I and class II peptides," Proteomics, 17(1-2) (2017), 16 pages; doi:10.1002/pmic.201600061.
Shapira, A. & Benhar, I., "Toxin-Based Therapeutic Approaches," Toxins, 2:2519-2583 (2010); doi:10.3390/toxins2112519.
Sharma, N. et al., "Isolation and Characterization of an RIP (Ribosome-Inactivating Protein)-Like Protein from Tobacco with Dual Enzymatic Activity," Plant Physiology, 134:171-181 (2004).
Singh, N. K. et al., "Emerging Concepts in TCR Specificity: Rationalizing and (Maybe) Predicting Outcomes," The Journal of Immunology, 199:2203-2213 (2017).
Spranger, S. et al., "Up-Regulation of PD-L1, IDO, and Tregs in the Melanoma Tumor Microenvironment Is Driven by CD8+ T Cells," Science Translational Medicine, 5(200):200ra116 (2013), 10 pages.
Stirpe, F. et al., "Activities associated with the presence of ribosome-inactivating proteins increase in senescent and stressed levels," FEBS Letters, 382:309-312 (1996).
Stirpe, F., "On the action of ribosome-inactivating proteins: are plant ribosomes species-specific," Biochemical Journal Letters, 202:279-280 (1982).
Stone, J. D. et al., "T-cell receptor binding affinities and kinetics: impact on T-cell activity and specificity," Immunology, 126:165-176 (2009).
Strauch, E. et al., "Characterization of a Shiga Toxin-Encoding Temperate Bacteriophage of *Shigella sonnei*," Infection and Immunity, 69(12):7588-7595 (2001).

(56) References Cited

OTHER PUBLICATIONS

Strome, S. E. et al., "B7—H1 Blockade Augments Adoptive T-Cell Immunotherapy for Squamous Cell Carcinoma," Cancer Research, 63:6501-6505 (2003).
Suhan, M. L. et al., "Disruption of an Internal Membrane-Spanning Region in Shiga Toxin I Reduces Cytotoxicity," Infection and Immunity, 66(11):5252-5259 (1998).
Tang, F. et al., "Tumor cells versus host immune cells: whose PD-L1 contributes to PD-1/PD-L1 blockade mediated cancer immuno-therapy?," Cell & Bioscience, 8:34 (2018), 8 pages.
Tesh, V. L. et al., "Comparison of the Relative Toxicities of Shiga-Like Toxins Type I and Type II for Mice," Infection and Immunity, 61(8):3392-3402 (1993).
Thompson, R. H. et al., "PD-1 Is Expressed by Tumor-Infiltrating Immune Cells and Is Associated with Poor Outcome for Patients with Renal Cell Carcinoma," Clin Cancer Res, 13(6):1757-1761 (2007).
Thompson, R. H. et al., "Tumor B7—H1 Is Associated with Poor Prognosis in Renal Cell Carcinoma Patients with Long-term Follow-up," Cancer Res, 66(7):3381-3385 (2006).
Tkachev, V. et al., "Programmed Death-1 Controls T Cell Survival by Regulating Oxidative Metabolism," The Journal of Immunology, 194:5789-5800 (2015).
UnitProtKB Q9NZQ7 (PD1L1_Human), last modified Apr. 7, 2021, 10 pages.
Van Heeckeren, W. J. et al., "Randomised comparison of two B-cell purging protocols for patients with B-cell non-Hodgkin lymphoma: in vivo purging with rituximab versus ex vivo purging with CliniMACS CD34+ cell enrichment device," British Journal of Haematology, 132:42-55 (2005).
Von Minckwitz, G. et al., "Phase I clinical study of the recombinant antibody toxin scFv(FRP5)-ETA specific for the ErbB2/HER2 receptor in patients with advanced solid malignomas," Breast Cancer Research, 7(5):R617-R626 (2005).
Vouri, M. & Hafizi, S., "TAM Receptor Tyrosine Kinases in Cancer Drug Resistance," Cancer Res, 77(11):2775-2778 (2017).
Walsh, M. J. et al., "Ribosome-inactivating proteins. Potent poisons and molecular tools," Virulence, 4(8):774-784 (2013).
Wang, P. & Tumer, N. E., "Pokeweed antiviral protein cleaves double-stranded supercoiled DNA using the same active site required to depurinate rRNA," Nucleic Acids Research, 27(8):1900-1905 (1999).
Wang, S.-C et al., "Polymorphisms of Genes for Programmed Cell Death 1 Ligands in Patients with Rheumatoid Arthritis," J Clin Immunol, 27:563-567 (2007).
Weldon, J. E. & Pastan, I., "A guide to taming a toxin—recombinant immunotoxins constructed from *Pseudomonas exotoxin* A for the treatment of cancer," FEBS Journal, 278:4683-4700 (2011).
Weidle, U. H. et al., "Prospects of Bacterial and Plant Protein-based Immunotoxins for Treatment of Cancer," Cancer Genomics & Proteomics, 11:25-38 (2014).
Wels, W. et al., "Selective Inhibition of Tumor Cell Growth by a Recombinant Single-Chain Antibody-Toxin Specific for the erbB-2 Receptor," Cancer Research, 52:6310-6317 (1992).
Wintterle, S. et al., "Expression of the B7-Related Molecule B7—H1 by Glioma Cells: A Potential Mechanism of Immune Paralysis," Cancer Research, 63:7462-7467 (2003).
Wu, C.-T. et al., "The role of PD-L1 in the radiation response and clinical outcome for bladder cancer," Scientific Reports, 6:19740 (2016), 9 pages; doi:10.1038/srep19740.
Xiao, W. et al., "IFNAR1 Controls Autocrine Type I IFN Regulation of PD-L1 Expression in Myeloid-Derived Suppressor Cells," The Journal of Immunology, 201:264-277 (2018).
Yang, Q. et al., "Association of polymorphisms in the programmed cell death of 1 (PD-1) and PD-1 ligand genes with ankylosing spondylitis in a Chinese population," Clinical and Experimental Rheumatology, 29:13-18 (2011).
Zhang, Y. et al., "Expression and clinical significance of programmed death-1 on lymphocytes and programmed death ligand-1 on monocytes in the peripheral blood of patients with cervical cancer," Oncology Letters, 14:7225-7231 (2017).
Zhaxybayeva, O. & Doolittle, W. F., "Lateral gene transfer," Current Biology, 21(7):R242-R246 (2011).
Zheng, P. & Zhou, Z., "Human Cancer Immunotherapy with PD-1/PD-L1 Blockade," Biomarkers in Cancer, 7(S2):15-18 (2015); doi:10.4137/BiC.s29325.
Zou, W. & Chen, L., "Inhibitory B7-family molecules in the tumour microenvironment," Nature Reviews Immunology, 8:467-477 (2008).
Romaniuk, D. S. et al., "Rapid Multiplex Genotyping of 20 HLA-A*02:01 Restricted Minor Histocompatibility Antigens," Front. Immunol., vol. 10, Article 1226 (2019), 10 pages; https://doi.org/10.3389/fimmu.2019.01226.
Rozanov, D. V. et al., "MHC class I loaded ligands from breast cancer cell lines: A potential HLA-I-typed antigen collection," J Proteomics, 176:13-23 (2018); doi:10.1016/j.jprot.2018.01.004.
Song, S. et al., "Full screening and accurate subtyping of HLA-A*02 alleles through group-specific amplification and mono-allelic sequencing," Cellular & Molecular Immunology, 10:490-496 (2013).
Vannitamby, A. et al., "A Novel Approach to Detect Programed Death Ligand 1 (PD-L1) Status and Multiple Tumor Mutations Using a Single Non-Small-Cell Lung Cancer (NSCLC) Bronchoscopy Specimen," The Journal of Molecular Diagnostics, 21(2):186-197 (2019).
Xu, S. et al., "PD-L1 monoclonal antibody-conjugated nanoparticles enhance drug delivery level and chemotherapy efficacy in gastric cancer cells," Int J Nanomedicine, 14:17-32 (2019).
Baxevanis, C.N., "Antibody-based Cancer Therapy," Expert Opin Drug Discov. Apr. 2008; 3(4):441-52. doi: 10.1517/17460441.3.4.441.
Bendig, M. M., "Humanization of Rodent Monoclonal Antibodies by CDR Grafting." Methods: A Companion to Methods: A Companion to Methods in Enzymology, 8:83-93 (1995).
Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," Cell Biol. Nov. 1990; 111(5 Pt 1):2129-38. doi: 10.1083/jcb.111.5.2129.
Cuzick et al., "Overview of the main outcomes in breast-cancer prevention trials," Lancet. Jan. 25, 2003; 361(9354):296-300. doi: 10.1016/S0140-6736(03)12342-2.
Dubel, S., Handbook of Therapeutic Antibodies, 2007, pp. 100-101.
Evans, T. R. & Kaye, S. B., "Vaccine therapy for cancer—fact or fiction?" Q.J. Med. Jun. 1999; 92(6):299-307. doi: 10.1093/qjmed/92.6.299.
Hernandez-Ledesma, B., et al., "Lunasin, a novel seed peptide for cancer prevention", Peptides. Feb. 2009;30(2):426-30. doi: 10.1016/j.peptides.2008.11.002. Epub Nov. 13, 2008.
Johnson, G. & Wu, T. T., "The Kabat Database and a Bioinformatics Example," Methods Mol Biol. 2004;248:11-25. doi: 10.1385/1-59259-666-5:11.
Komenaka, I., et al., "Immunotherapy for Melanoma," Clin Dermatol. May-Jun. 2004; 22(3):251-65. doi: 10.1016/j.clindermatol.2003.12.001.
Lazar E., et al., "Transforming Growth Factor Alpha: Mutation of Aspartic Acid 47 and Leucine 48 Results in Different Biological Activities," Molecular and Cellular Biology, Mar. 1988, vol. 8 (3), pp. 1247-1252.
Paul, W.E. (1993) "Fv Structure and Diversity in Three Dimensions" in Fundamental Immunology, 3rd ed. Raven Press, NY; Chap. 9, pp. 292-295.
Polyak. M.J. & Deans, J. P., "Alanine-170 and proline-172 are critical determinants for extracellular CD20 epitopes; heterogeneity in the fine specificity of CD20 monoclonal antibodies is defined by additional requirements imposed by both amino acid sequence and quaternary structure," Blood. May 1, 2002;99(9):3256-62. doi: 10.1182/blood.v99.9.3256.
Ribas, A., et al., "What does PD-L1 Positive or Negative Mean?" J Exp Med. Dec. 12, 2016; 213(13):2835-2840. doi: 10.1084/jem.20161462. Epub Nov. 30, 2016.
Rudikoff, S. et al., "Single amino acid substitution altering antigen-binding specificity," Proceedings of the National Academy of Sciences, USA, Mar. 1982, 79(6), pp. 1979-1983.

(56) References Cited

OTHER PUBLICATIONS

Schiffman, M., et al., “The Promise of Global Cervical-Cancer Prevention,” N Engl J Med. Nov. 17, 2005;353(20):2101-4. doi: 10.1056/NEJMp058171.
U.S. Appl. No. 18/425,310, filed Jan. 29, 2024.

* cited by examiner

REPLACEMENT SHEET

Note: In Part B, PD-L1 expression will be confirmed by central laboratory.
MTD = maximum tolerated dose; NSCLC = non-small cell lung carcinoma; PD-L1 = programmed death-ligand 1; RP2D = recommended Phase 2 dose; SCCHN = squamous cell carcinoma of the head and neck.

PD = progressive disease; Q2W = every 2 weeks; QW = once weekly.

NOTE: The dose level may be reduced or the dose schedule may be changed to a less frequent one if after at least 10 enrolled subjects the toxicity driven dose reductions indicate its necessity.

MTD = maximum tolerated dose; PD = progressive disease.

Number of patients treated at current dose

| Number of toxicities | 3 | 4 | 5 | 6 | 7 | 8 |
|---|---|---|---|---|---|---|
| 0 | E | E | E | E | E | E |
| 1 | S | E | E | E | E | E |
| 2 | D | D | D | S | S | E |
| 3 | DU | DU | D | D | D | S |
| 4 | | DU | DU | DU | D | D |
| 5 | | | DU | DU | DU | DU |
| 6 | | | | DU | DU | DU |
| 7 | | | | | DU | DU |
| 8 | | | | | | DU |

Figure 8

CLINICAL METHODS FOR USE OF A PD-L1-BINDING MOLECULE COMPRISING A SHIGA TOXIN EFFECTOR

CROSS-REFERENCE TO RELATED APPLICATIONS

This application claims priority to U.S. Pat. App. No. 63/126,304, filed Dec. 16, 2020, which is incorporated by reference herein in its entirety for all purposes.

TECHNICAL FIELD

The present application relates to PD-L1 binding molecules comprising a PD-L1-binding region, a Shiga toxin effector region, and a T-cell epitope, and pharmaceutical compositions thereof. The application also relates to clinical methods for use of the PD-L1 binding molecules for the treatment of cancer.

SEQUENCE LISTING

The Sequence Listing associated with this application is provided in text format in lieu of a paper copy, and is hereby incorporated by reference into the specification. The name of the text file containing the Sequence Listing is MTEM_023_01_US_SeqList_ST25.txt. The text file is about 25 kilobytes in size, was created on Dec. 16, 2021, and is being submitted electronically via EFS-Web.

BACKGROUND

Programmed death ligand 1 (PD-L1) is highly expressed in many cancers, including a variety of solid tumor malignancies, such as non-small cell lung cancer (NSCLC) and squamous cell carcinoma of the head and neck (SCCHN). PD-L1 binds to PD-1 on T-cells to inhibit T-cell activation and evade detection by the immune system. PD-L1 is therefore an attractive target for the treatment of PD-L1-expressing malignancies.

Current PD-L1 targeted therapies for the treatment of cancer show efficacy in only a small subset of patients, and many patients acquire resistance to PD-L1 targeted therapies over time. Therefore, there remains a need in the art to develop effective pharmaceutical compositions and therapeutic methods which target and kill tumor cells expressing PD-L1. In particular, there remains a need in the art for therapies using PD-L1-binding molecules which exhibit efficient and effective cellular internalization, intracellular-routing, and potent cytotoxicity toward PD-L1-expressing tumor cells for the treatment of cancer.

SUMMARY

Provided herein are PD-L1-binding molecules and pharmaceutical compositions thereof. In some embodiments, the PD-L1 binding molecules comprise a PD-L1-binding region and a Shiga toxin effector region, and optionally, a T-cell epitope. Also provided herein are clinical methods for use of the PD-L1-binding molecules and pharmaceutical compositions thereof for the treatment of subjects with cancer, e.g., NSCLC or SCCHN.

The present disclosure provides a pharmaceutical composition comprising: (i) a PD-L1 binding molecule comprising a polypeptide having the amino acid sequence of SEQ ID NO:1; and (ii) at least one pharmaceutically acceptable carrier or excipient.

In some embodiments, the concentration of the PD-L1 binding molecule is about 0.1 mg/mL to about 5 mg/mL. In some embodiments, the concentration of the PD-L1 binding molecule is about 0.25 mg/mL, about 0.5 mg/mL, about 1 mg/mL, about 2 mg/mL, about 2.5 mg/mL, or about 5.0 mg/mL. In some embodiments, the concentration of the PD-L1 binding molecule is about 0.5 mg/mL. In some embodiments, the concentration of the PD-L1 binding molecule is about 1 mg/mL.

In some embodiments, the at least one pharmaceutically acceptable carrier or excipient is selected from a co-solvent, a surfactant, a preservative, a viscosity modifier, a suspending agent, a buffer, an antioxidant, a chelating agent, a humectant, an emulsifying agent, a flocculating agent, and an isotonicity agent.

In some embodiments, the at least one pharmaceutically acceptable carrier or excipient is a buffer. In some embodiments, the buffer is a citrate buffer, a phosphate buffer, an acetate buffer, a succinate buffer, a histidine buffer, a Tris buffer, a tartrate buffer, a glycine buffer, a glutamate buffer, or a mixture thereof. In some embodiments, the buffer is a citrate buffer. In some embodiments, the buffer comprises sodium citrate at a concentration of about 5 mM to about 30 mM. In some embodiments, the buffer comprises sodium citrate at a concentration of about 20 mM.

In some embodiments, the at least one pharmaceutically acceptable carrier or excipient is an isotonicity agent. In some embodiments, the isotonicity agent is a sugar or a sugar alcohol. In some embodiments, the sugar or sugar alcohol is sorbitol, sucrose, or trehalose.

In some embodiments, the at least one pharmaceutically acceptable carrier or excipient is a surfactant. In some embodiments, the surfactant is polysorbate-20, polysorbate-80, or a combination thereof. In some embodiments, the composition comprises sorbitol and polysorbate-80. In some embodiments, the concentration of sorbitol is about 50 mM to about 300 mM. In some embodiments, the concentration of sorbitol is about 200 mM. In some embodiments, the concentration of polysorbate-80 is about 0.005% (v/v) to about 0.015% (v/v). In some embodiments, the concentration of polysorbate-80 is about 0.01% (v/v).

In some embodiments, the pharmaceutical composition comprises about 200 mM sorbitol, about 20 mM sodium citrate, and about 0.01% (v/v) polysorbate-80. In some embodiments, the pharmaceutical composition further comprises a salt selected from sodium chloride and arginine.

In some embodiments, the pharmaceutical composition has a pH of about 5.2 to about 5.8. In some embodiments, the pH is about 5.5. In some embodiments, the pH is about 5.6.

In some embodiments, the pharmaceutical composition is at least 99% (w/v) free of impurities. In some embodiments, the composition comprises no more than 1% (w/v) of impurities. In some embodiments, the impurities comprise one or more of endotoxin, bioburden, host cell protein, host cell DNA, kanamycin, triton X-100, protein L, and glucan. In some embodiments, the composition comprises endotoxin at a concentration of ≤5 EU/mL, ≤4 EU/mL, ≤3 EU/mL, ≤2 EU/mL, or ≤1 EU/mL. In some embodiments, the composition comprises endotoxin at a concentration of ≤0.5 EU/mL. In some embodiments, the composition comprises bioburden at a concentration of ≤1 CFU/mL. In some embodiments, the composition comprises host cell protein at a concentration of ≤1 ng/mL. In some embodiments, the composition comprises host cell DNA at a concentration of ≤0.1 ng/mL. In some embodiments, the composition comprises kanamycin at a concentration of ≤250 ng/mL. In some embodiments, the composition comprises kanamycin at a concentration of ≤50 ng/mL. In some embodiments, the composition comprises triton X-100 at a concentration of ≤250 ng/mL In some embodiments, the composition comprises protein L at a concentration of ≤1 ng/mL. In some embodiments, the composition comprises protein L at a concentration of ≤0.025 ng/mL. In some embodiments, the composition comprises glucan at a concentration of ≤1 ng/mL.

In some embodiments, the pharmaceutical composition is diluted with 5% dextrose in water. In some embodiments, the pharmaceutical composition is diluted with 0.9% sodium chloride in water.

In some embodiments, the pharmaceutical composition is substantially stable for at least 3 months at about −10° C. to about −25° C. In some embodiments, the pharmaceutical composition is substantially stable for at least 3 months at about 2° C. to about 8° C. In some embodiments, the pharmaceutical composition is substantially stable after two freeze/thaw cycles. In some embodiments, the pharmaceutical composition is substantially stable for at least 24 hours at room temperature.

In some embodiments, the disclosure provides a method for treating or slowing the progression of a solid tumor, the method comprising administering to a subject in need thereof an effective amount of a pharmaceutical composition of the disclosure. In some embodiments, the solid tumor expresses PD-L1.

In some embodiments, the disclosure provides a method for treating or slowing the progression of a solid tumor, the method comprising administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose of about 1 µg/kg to about 200 µg/kg of the subject's body weight. In some embodiments, the PD-L1 biding molecule is administered at a dose of about 8 µg/kg, about 10 µg/kg, about 16 µg/kg, about 20 µg/kg, about 25 µg/kg, about 30 µg/kg, about 40 µg/kg, about 50 µg/kg, or about 75 µg/kg of the subject's body weight. In some embodiments, the PD-L1 binding molecule is administered at a dose of about 30 µg/kg of the subject's body weight. In some embodiments, the PD-L1 binding molecule is administered at a dose of about 16 µg/kg of the subject's body weight. In some embodiments, the PD-L1 binding molecule is administered at a dose of about 8 µg/kg of the subject's body weight. In some embodiments, the solid tumor expresses PD-L1.

In some embodiments, the PD-L1 binding molecule is administered weekly during a first 28-day cycle, wherein the PD-L1 binding molecule is administered on days 1, 8, 15, and 22 of the first 28-day cycle. In some embodiments, the PD-L1 binding molecule is administered two times during a first 28-day cycle, wherein the PD-L1 binding molecule is administered on days 1 and 15 of the first 28-day cycle. In some embodiments, the PD-L1 binding molecule is administered three times during a first 28-day cycle, wherein the PD-L1 binding molecule is administered on days 1, 8, and 15 of the first 28-day cycle.

In some embodiments, the method further comprises administering the PD-L1 binding molecule weekly during a second 28-day cycle following the first 28-day cycle, wherein the PD-L1 binding molecule is administered on days 1, 8, 15, and 22 of the second 28-day cycle. In some embodiments, the PD-L1 binding molecule is administered two times during a second 28-day cycle following the first 28-day cycle, wherein the PD-L1 binding molecule is administered on days 1 and 15 of the second 28-day cycle. In some embodiments, the PD-L1 binding molecule is administered three times during a second 28-day cycle, wherein the PD-L1 binding molecule is administered on days 1, 8, and 15 of the second 28-day cycle. In some embodiments, the PD-L1 binding molecule is administered at a dose of about 1 µg/kg to about 200 µg/kg of the subject's body weight during the second 28-day cycle. In some embodiments, the PD-L1 binding molecule is administered at a dose of about 8 µg/kg, about 10 µg/kg, about 16 µg/kg, about 20 µg/kg, about 25 µg/kg, about 30 µg/kg, about 40 µg/kg, about 50 µg/kg, or about 75 µg/kg of the subject's body weight during the second 28-day cycle. In some embodiments, the PD-L1 binding molecule is administered at a dose of about 30 µg/kg of the subject's body weight during the second 28-day cycle. In some embodiments, the PD-L1 binding molecule is administered at a dose of about 16 µg/kg of the subject's body weight during the second 28-day cycle. In some embodiments, the PD-L1 binding molecule is administered at a dose of about 8 µg/kg of the subject's body weight during the second 28-day cycle.

In some embodiments, the method further comprises administering the PD-L1 binding molecule weekly during a third 28-day cycle following the first and second 28-day cycles, wherein the PD-L1 binding molecule is administered on days 1, 8, 15, and 22 of the third 28-day cycle. In some embodiments, the PD-L1 binding molecule is administered two times during a third 28-day cycle following the first and second 28-day cycles, wherein the PD-L1 binding molecule is administered on days 1 and 15 of the third 28-day cycle. In some embodiments, the PD-L1 binding molecule is administered three times during a third 28-day cycle following the first and second 28-day cycles, wherein the PD-L1 binding molecule is administered on days 1, 8, and 15 of the third 28-day cycle. In some embodiments, the PD-L1 binding molecule is administered at a dose of about 1 µg/kg to about 200 µg/kg of the subject's body weight during the third 28-day cycle. In some embodiments, the PD-L1 binding molecule is administered at a dose of about 8 µg/kg, about 10 µg/kg, about 16 µg/kg, about 20 µg/kg, about 25 µg/kg, about 30 µg/kg, about 40 µg/kg, about 50 µg/kg, or about 75 µg/kg of the subject's body weight during the third 28-day cycle. In some embodiments, the PD-L1 binding molecule is administered at a dose of about 30 µg/kg of the subject's body weight during the third 28-day cycle. In some embodiments, the PD-L1 binding molecule is administered at a dose of about 16 µg/kg of the subject's body weight during the third 28-day cycle. In some embodiments, the PD-L1 binding molecule is administered at a dose of about 8 µg/kg of the subject's body weight during the third 28-day cycle.

In some embodiments, the method further comprises administering the PD-L1 binding molecule for at least one additional 28-day cycle. In some embodiments, the PD-L1 binding molecule is administered at a dose of about 1 µg/kg to about 200 µg/kg of the subject's body weight during the at least one additional 28-day cycle. In some embodiments, the PD-L1 binding molecule is administered at a dose of about 8 µg/kg, about 10 µg/kg, about 16 µg/kg, about 20 µg/kg, about 25 µg/kg, about 30 µg/kg, about 40 µg/kg, about 50 µg/kg, or about 75 µg/kg of the subject's body weight during the at least one additional 28-day cycle. In some embodiments, the PD-L1 binding molecule is administered at a dose of about 30 µg/kg of the subject's body weight during the at least one additional 28-day cycle. In some embodiments, the PD-L1 binding molecule is administered at a dose of about 16 µg/kg of the subject's body weight during the at least one additional 28-day cycle. In some embodiments, the PD-L1 binding molecule is administered at a dose of about 8 μg/kg of the subject's body weight during the at least one additional 28-day cycle.

In some embodiments, the dose of the PD-L1 binding molecule administered to the subject over one or more cycles is about 5 mg to about 100 mg.

In some embodiments, the PD-L1 binding molecule is administered by intravenous infusion. In some embodiments, the intravenous infusion is over about 5 minutes to about 120 minutes. In some embodiments, the intravenous infusion is over about 30 minutes.

In some embodiments, the solid tumor is squamous cell carcinoma of the head and neck. In some embodiments, the solid tumor is non-small cell lung cancer. In some embodiments, the solid tumor is unresectable, locally advanced, or metastatic.

In some embodiments, the cancer is relapsed or refractory to treatment with at least one additional anti-cancer therapy. In some embodiments, the cancer is relapsed or refractory to treatment with at least one of ipilimumab, nivolumab, pembrolizumab, atezolizumab, durvalumab, avelumab, tremelimumab or cemiplimab. In some embodiments, the cancer is relapsed or refractory to a platinum-based therapy.

In some embodiments, the disclosure provides a method for treating or slowing the progression of non-small cell lung cancer, the method comprising administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight. In some embodiments, the PD-L1 binding molecule is administered at a dose of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the non-small cell lung cancer expresses PD-L1.

In some embodiments, the disclosure provides a method for treating or slowing the progression of squamous cell carcinoma of the head and neck, the method comprising administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight. In some embodiments, the PD-L1 binding molecule is administered at a dose in the range of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the non-small cell lung cancer expresses PD-L1.

In some embodiments, the disclosure provides a method for treating or slowing the progression of a solid tumor that expresses PD-L1, the method comprising administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight.

In some embodiments, the disclosure provides a method of treating or slowing the progression of a solid tumor that expresses PD-L1, the method comprising screening the subject for an HLA:A*02 haplotype and treating the subject that is positive for the HLA:A*02 haplotype with a PD-L1 binding molecule comprising a polypeptide having the sequence of SEQ ID NO: 1; wherein the PD-L1 binding molecule is administered at a dose in the range of about 1 μg/kg to about 200 μg/kg of the subject's body weight.

In some embodiments, the disclosure provides a method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor.

In some embodiments, the disclosure provides a method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor; and wherein prior to administration of the PD-L1 binding molecule, the subject is screened for an HLA:A*02 haplotype.

In some embodiments, the disclosure provides a method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor; and wherein prior to administration of the PD-L1 binding molecule, the subject is screened for an HLA:A*02 haplotype.

In some embodiments, the disclosure provides a method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor. In some embodiments, prior to administration of the PD-L1 binding molecule, the subject is screened for an HLA:A*02 haplotype. In some embodiments, prior to administration of the PD-L1 binding molecule, the subject is screened for CMV.

The disclosure also provides a method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, the subject is screened for CMV. In some embodiments, prior to administration of the PD-L1 binding molecule, the subject is screened for an HLA:A*02 haplotype. In some embodiments, prior to administration of the PD-L1 binding molecule, PD-L1 expression is detected on cells isolated or derived from the solid tumor.

The disclosure also provides a kit for detecting PD-L1 expression in a sample from a subject. In some embodiments, the kit comprises: (i) one or more PCR primers capable of amplifying a nucleic acid sequence encoding PD-L1; (ii) one or more antibodies that specifically bind to PD-L1; or (iii) a PD-L1 binding molecule of SEQ ID NO: 1. In some embodiments, the sample is isolated or derived from the subject's solid tumor.

The disclosure also provides a kit for detecting an HLA: A*02 haplotype in a sample from a subject. In some embodiments, the kit comprises: (i) one or more PCR primers capable of amplifying the HLA-A*02 gene or the B2M locus; or (ii) one or more antibodies capable of recognizing the HLA:A*02 haplotype. In some embodiments, the kit comprises one or more antibodies that specifically bind to the alpha-2 domain of the HLA-A alpha-chain. In some embodiments, the sample is isolated or derived from the subject's solid tumor.

The disclosure also provides a kit for screening in a sample from a subject for CMV.

The disclosure also provides a method for determining whether a subject would be responsive to treatment with the PD-L1 binding molecule of SEQ ID NO: 1, the method comprising using a kit to detect PD-L1 expression in a sample from the subject. In some embodiments, detection of PD-L1 expression in the sample from the subject indicates that the subject would be responsive to treatment with the PD-L1 binding molecule of SEQ ID NO: 1.

The disclosure also provides a method for determining whether a subject would be responsive to treatment with the PD-L1 binding molecule of SEQ ID NO: 1, the method comprising using a kit to detect an HLA:A*02 haplotype in a sample from a subject. In some embodiments, detection of the HLA:A*02 haplotype in the sample from the subject indicates that the subject would be responsive to treatment with the PD-L1 binding molecule of SEQ ID NO: 1.

The disclosure also provides a method for determining whether a subject would be responsive to treatment with the PD-L1 binding molecule of SEQ ID NO: 1, the method comprising using a kit to detect CMV in a sample from a subject.

These and other features, aspects and advantages of the present invention will become better understood with regard to the following description, appended claims, examples and accompanying figures.

BRIEF DESCRIPTION OF THE DRAWINGS

FIG. 8 shows a schema of the dose-escalation/de-escalation strategy for Part A of the study.

FIG. 9A shows absolute number of cells (cells/μl) in the samples, and FIG. 9B shows percent change compared to predose levels (i.e., before Cycle 1 (C1)). This data is summarized in FIG. 9C.

DETAILED DESCRIPTION

Definitions

Figure 1A:
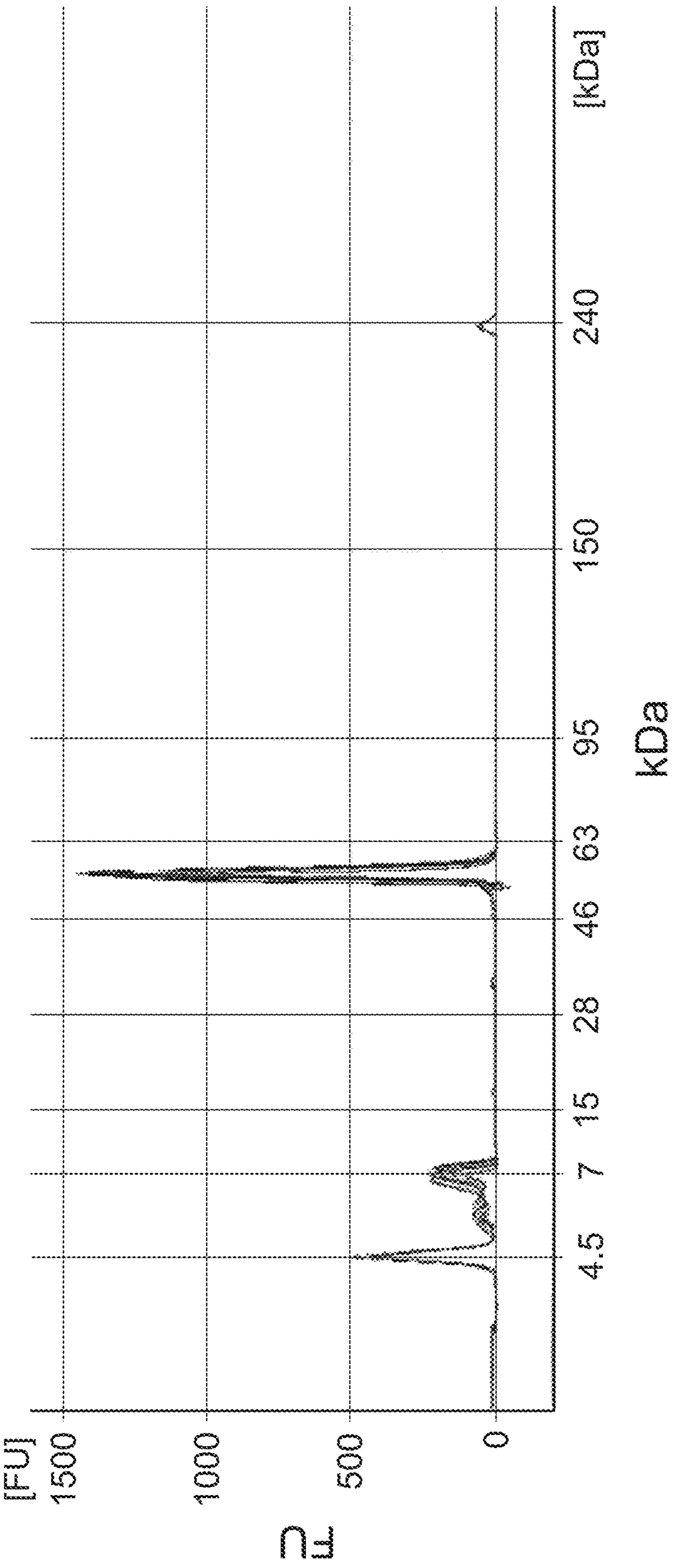
FIG. 1A shows a capillary gel electrophoresis (CGE) electropherogram for the 116297 drug substance under reducing denaturing conditions.

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope described herein to those skilled in the art.

In order that the present invention is more readily understood, certain terms are defined below. Additional definitions may be found within the detailed description described herein.

As used in the specification and the appended claims, the terms "a," "an" and "the" include both singular and the plural referents unless the context clearly dictates otherwise.

The term "about" when immediately preceding a numerical value means ± up to 20% of the numerical value. In some embodiments, "about" a numerical value means ± up to 20%, ± up to 19%, ± up to 18%, ± up to 17%, ± up to 16%, ± up to 15%, ± up to 14%, ± up to 13%, ± up to 12%, ± up to 11%, ± up to 10%, ± up to 9%, ± up to 8%, ± up to 7%, ± up to 6%, ± up to 5%, ±up to 4%, ± up to 3%, ± up to 2%, ± up to 1%, ± up to less than 1%, or any other value or range of values therein, of the numerical value.

The term "polynucleotide" or "nucleic acid" refers to a polymer of nucleotide monomers covalently bonded in a chain. Exemplary nucleic acids include DNA and RNA.

The term "amino acid" refers to structural units (monomers) that make up a protein, polypeptide, or peptide. The term "polypeptide" or "protein" includes any polymer of amino acids or amino acid residues. A "peptide" is a small polypeptide of sizes less than about 15 to 20 amino acid residues. The term "amino acid sequence" refers to a series of amino acids or amino acid residues.

Methods for determining sequence similarity or identity between two or more nucleic acid sequences or two or more amino acid sequences are known in the art. Sequence similarity or identity may be determined using standard techniques, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection. Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). An exemplary BLAST program is the WU-BLAST-2 program which was obtained from Altschul et al., Methods in Enzymology, 266, 460-480 (1996); blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity. Further, an additional algorithm is gapped BLAST as reported by Altschul et al, (1997) Nucleic Acids Res. 25, 3389-3402. Unless indicated otherwise, calculation of percent identity is performed in the instant disclosure using the BLAST algorithm available at the world wide web address: blast.ncbi.nlm.nih.gov/Blast.cgi.

The term "monomeric" or "monomer" refers to a PD-L1-binding molecule comprising one single, continuous polypeptide.

The term "multimeric" refers to a PD-L1-binding molecule comprising two or more polypeptides associated or linked together. Multimeric PD-L1 molecules may be dimers, trimers, tetramers, and higher order structures.

As used herein, the phrases "PD-L1-expressing cell", "PD-L1 positive cell", or "PD-L1+ cell" encompasses any cell that expresses PD-L1 on the extracellular surface of the cell, e.g., a PD-L1 molecule comprising a transmembrane domain.

The phrase "derived from" refers an amino acid sequence originally found in a protein or polypeptide, which comprises additions, deletions, truncations, rearrangements, or other alterations relative to the original sequence as long as the overall function and structure are substantially conserved.

The term "heavy chain variable ($V_H$) domain" or "light chain variable ($V_L$) domain" respectively refer to any antibody $V_H$ or $V_L$ domain (e.g., a human VH or VL domain) as well as any derivative thereof retaining at least qualitative antigen binding ability of the corresponding native antibody. A $V_H$ or $V_L$ domain consists of a "framework" region interrupted by three complementarity determining regions ("CDRs"). The framework regions serve to align the CDRs for specific binding to an epitope of an antigen, e.g., PD-L1. From amino to carboxy terminus, both $V_H$ and $V_L$ domains comprise the following framework (FR) and CDR regions: FR1, CDR1, FR2, CDR2, FR3, CDR3, and FR4.

The "complementary-determining region" or "CDR" of a $V_H$ or $V_L$ domain binds to at least one epitope of the antigen of interest (e.g., a PD-L1 molecule). An antigen-binding fragment of the PD-L1-binding region (e.g., an anti-PD-L1 scFv) may comprise 1, 2, 3, 4, 5, or all 6 CDRs of a $V_H$ and $V_L$ sequence from antibodies that specifically bind PD-L1.

The term single chain variable fragment "scFv" refers to a PD-L1-binding region comprising a $V_H$ domain and a $V_L$ domain, wherein the $V_H$ domain and $V_L$ domain are linked by a peptide linker which allows the two domains to associate to form an antigen-binding site.

The term "embedded" refers to the replacement of one or more amino acids within a polypeptide region (e.g., a Shiga toxin effector region) with different amino acids, resulting in a polypeptide sequence sharing the same total number of amino acids as the native polypeptide region. For example, in some embodiments, a T-cell epitope is embedded into a Shiga toxin effector region.

The term "inserted" refers to the insertion of one or more amino acids within a polypeptide region (e.g., a Shiga toxin effector region), resulting in a polypeptide sequence with an increased number of amino acids as compared to the native polypeptide region. For example, in some embodiments, a T-cell epitope is inserted into a Shiga toxin effector region.

As used herein, "de-immunized" refers to a PD-L1-binding molecule with reduced antigenicity and/or immunogenicity after administration to a subject as compared to a "parental" PD-L1-binding molecule from which it was derived, such as, e.g., a wild-type Shiga toxin effector region (e.g., SLT-1A) or a PD-L1-binding molecule comprising the aforementioned.

As used herein, the terms "treat," "treating," or "treatment", and grammatical variants thereof, have the same meaning as commonly understood by those of ordinary skill in the art. In some embodiments, these terms may refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease or condition.

As used herein, the terms "prevent," "preventing," "prevention" and grammatical variants thereof refer to an approach for preventing the development of, or altering the pathology of, a condition or disease. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

The term "solid tumor" refers to an abnormal mass of tissue resulting from abnormal growth or division of cells. Solid tumors may be benign (not cancerous) or malignant (cancerous). Examples of solid tumors include, but are not limited to, sarcomas, carcinomas, and lymphomas. In some embodiments, the solid tumor is PD-L1 positive. In some embodiments, the solid tumor is small-cell lung cancer or squamous cell carcinoma of the head and neck.

The term "IC50" or "$IC_{50}$" refers to the half-maximal inhibitory concentration as measured using in an in vitro ribosome function assay or cell killing and/or survival assay. The term "CD50" or "$CD_{50}$" is refers to the half-maximal cytotoxicity concentration in an in vitro cell killing and/or survival assay. A "drug" or "drug substance" refers to an active ingredient to be administered to a subject for the treatment of a disease such as cancer. In some embodiments, the drug or drug substance is a PD-L1-binding molecule. An active ingredient refers to a biologically active substance (e.g., a compound, a protein or a polypeptide, a peptide, a nucleic acid) that provides a pharmacological, biological, or therapeutic effect when administered to a subject.

The term "drug product" refers to a formulated dosage form such as a tablet, capsule, or solution, that contains a drug substance in association with one or more pharmaceutically acceptable excipients or carriers. The term "drug product", as used herein, is synonymous with the terms "medicament" or "pharmaceutical composition". In some embodiments, the drug product comprises a PD-L1-binding molecule in a citrate buffer comprising one or more pharmaceutically acceptable carriers or excipients.

As used herein, an "effective amount" is an amount effective for treating and/or preventing a disease, disorder, or condition as disclosed herein. In some embodiments, an effective amount is an amount or dose of a composition (e.g. a pharmaceutical composition, compound, or agent) that produces at least one desired therapeutic effect in a subject, such as preventing or treating a target condition or beneficially alleviating a symptom associated with the condition. The most desirable effective amount is an amount that will produce a desired efficacy of a particular treatment selected by one of skill in the art for a given subject in need thereof. This amount will vary depending upon a variety of factors understood by the skilled worker, including but not limited to the characteristics of the composition (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration.

The term "tolerated" refers to the absence of adverse effects in a subject or to the presence of tolerable adverse effects (e.g., mild side effects).

The term "half-life" or "T½" refers to the time taken for half the initial dose of PD-L1-binding molecule administered to be eliminated from the body.

The phrase "pharmaceutically acceptable carrier" refers to any material, composition, or vehicle that is physiologically acceptable, i.e., compatible buffer, solvents, dispersion media, coatings, antimicrobial agents, isotonic, absorption delaying agents, solid or liquid filler, excipients, encapsulating material, and the like. The phrase "pharmaceutically acceptable excipient" means an excipient that is useful in preparing a pharmaceutical composition that is generally safe, non-toxic and neither biologically nor otherwise undesirable, and includes an excipient, that is acceptable human pharmaceutical use as well veterinary use. Additional examples of pharmaceutically acceptable carriers and excipients are shown in Table 2.

The term "pharmaceutically acceptable salt" refers to a pharmaceutically acceptable salt derived from a variety of organic and inorganic counter ions well-known in the art.

The term "stable" or "substantially stable" refers to the extent the PD-L1-binding molecule retains, throughout its period of storage and use, the same properties and characteristics that it possessed at the time of its manufacture. A stable composition may have one or more of the following types of stability: chemical (e.g., pH), physical (e.g., aggregation), microbiological, therapeutic (e.g., cytotoxicity or target cell delivery), and/or toxicological. Drug stability assessment generally involves testing the drug substance or drug product using a stability-indicating method in order to determine shelf life. Stability-indicating methods are well-recognized by those skilled in the art.

As used herein, the term "buffer" or "buffering agent" refers to one or more components that when added to an aqueous solution is able to protect the solution against variations in pH when adding acid or alkali, or upon dilution with a solvent. A non-limiting list of buffers that may be used in the compositions described herein includes citrate, phosphate, acetate, succinate, histidine, Tris, tartrate, glycine, and glutamate buffers.

The term "impurity" refers to an undesirable or unwanted constituent present in a pharmaceutical composition. An impurity as used herein may be a product-related impurity or a process-related impurity.

The term "bioburden" refers to the number of pathogens with which a pharmaceutical composition is contaminated. The degree of bioburden may be measured by counting the number of colony-forming units (CFUs). A CFU is a measure of viable bacterial or fungal numbers, and may be reported as CFU/mL (colony-forming units per milliliter) for liquids, and CFU/g (colony-forming units per gram) for solids.

The terms "patient" and "subject" are used interchangeably to refer to any organism, commonly vertebrates such as humans and animals, which present symptoms, signs, and/or indications of at least one disease, disorder, or condition. These terms include, but are not limited to, mammals such as primates, livestock animals (e.g. cattle, horses, pigs, sheep, goats), companion animals (e.g. cats, dogs) and laboratory animals (e.g. mice, rabbits, rats).

PD-L1-Binding Molecules and Pharmaceutical Compositions Thereof

The PD-L1-binding molecules described herein comprise (i) a PD-L1-binding region; (ii) a Shiga toxin effector region; and (iii) a T cell epitope. In some embodiments, the PD-L1-binding molecule is a homodimer comprising two identical monomers, wherein each monomer comprises (i) a PD-L1-binding region; (ii) a Shiga toxin effector region; and (iii) a T cell epitope.

PD-L1-Binding Region:

In some embodiments, the PD-L1-binding molecule comprises a PD-L1-binding region. As used herein, the term "PD-L1-binding region" refers to a polypeptide capable of specifically binding a PD-L1 molecule with high affinity.

In some embodiments, the PD-L1-binding molecule comprises a PD-L1-binding region which is an scFv comprising a $V_H$ domain and a $V_L$ domain. In some embodiments, the anti-PD-L1 scFv comprises a linker which connects the $V_H$ domain and the $V_L$ domain.

In some embodiments, the anti-PD-L1 scFv specifically binds to human-PD-L1 or an isoform or variant thereof. In some embodiments, the anti-PD-L1 scFv specifically binds to human PD-L1 present on the surface of a cell membrane, such as, e.g., PD-L1 expressing cell or PD-L1 positive cell. In some embodiments, the anti-PD-L1 scFv specifically binds to a human PD-L1-positive tumor cell.

In some embodiments, the anti-PD-L1 scFv has a dissociation constant of $10^{-5}$ to $10^{-12}$ moles per liter. For example, in some embodiments, the anti-PD-L1 scFv has a dissociation constant of about 500 nM, about 400 nM, about 300 nM, about 200 nM, about 100 nM, about 75 nM, about 50 nM, about 25 nM, or about 10 nM. In some embodiments, the anti-PD-L1 scFv has a dissociation constant of less than 200 nM.

In some embodiments, the PD-L1-binding region is an anti-PD-L1 scFv comprising an amino acid sequence with at least 90%, at least 95%, at least 96%, at least 97%, at least 98%, or at least 99% identity to SEQ ID NO: 2. In some embodiments, the PD-L1-binding region is an anti-PD-L1 scFv comprising the amino acid sequence of SEQ ID NO: 2. In some embodiments, the PD-L1-binding region is an anti-PD-L1 scFv comprising the amino acid sequence of SEQ ID NO: 2 with one or more mutations relative thereto. For example, in some embodiments, the PD-L1-binding region may comprise 1, 2, 3, 4, 5, 6, 7, 8, 9, 10, or more mutations relative to SEQ ID NO: 2. In some embodiments, the PD-L1-binding region is an anti-PD-L1 scFv comprising the amino acid sequence of SEQ ID NO: 2 with 1-5, 5-10, 11-15, 15-20, 10-25, 25-30, or more than 30 mutations.

In some embodiments, the $V_H$ domain of the anti-PD-L1 scFv comprises an amino acid sequence with at least 90%, at least 95%, at least 96%, at least 97%, at least 98%, or at least 99% identity to SEQ ID NO: 3. In some embodiments, the $V_H$ domain of the anti-PD-L1 scFv comprises the amino acid sequence of SEQ ID NO: 3. In some embodiments, the $V_H$ domain of the anti-PD-L1 scFv comprises the amino acid sequence of SEQ ID NO: 3 with one or more mutations relative thereto. For example, in some embodiments, the $V_H$ domain comprises 1, 2, 3, 4, 5, 6, 7, 8, 9, 10, or more mutations relative to SEQ ID NO: 3. In some embodiments, the $V_H$ domain of anti-PD-L1 scFv comprises the amino acid sequence of SEQ ID NO: 3 with 1-5, 5-10, 11-15, 15-20, 10-25, 25-30, or more than 30 mutations.

In some embodiments, the $V_L$ domain of the anti-PD-L1 scFv comprises an amino acid sequence with at least 90%, at least 95%, at least 96%, at least 97%, at least 98%, or at least 99% identity to SEQ ID NO: 4. In some embodiments, the $V_L$ domain of the anti-PD-L1 scFv comprises the amino acid sequence of SEQ ID NO: 4. In some embodiments, the $V_L$ domain of the anti-PD-L1 scFv comprises the amino acid sequence of SEQ ID NO: 4 with one or more mutations relative thereto. For example, in some embodiments, the $V_L$ domain comprises 1, 2, 3, 4, 5, 6, 7, 8, 9 or 10 mutations relative to SEQ ID NO: 4. In some embodiments, the $V_L$ domain of the anti-PD-L1 scFv comprises the amino acid sequence of SEQ ID NO: 4 with 1-5, 5-10, 11-15, 15-20, 10-25, 25-30, or more than 30 mutations.

In some embodiments, the PD-L1-binding region is an scFv comprising: a) a $V_H$ domain comprising (i) an HCDR1 comprising or consisting of the amino acid sequence of SEQ ID NO: 5; (ii) an HCDR2 comprising or consisting of the amino acid sequence of SEQ ID NO: 6; and (iii) an HCDR3 comprising or consisting of the amino acid sequence of SEQ ID NO:7; and b) a $V_L$ domain comprising (i) an LCDR1 comprising or consisting of the amino acid sequence of SEQ ID NO:8; (ii) an LCDR2 comprising or consisting of the amino acid sequence of SEQ ID NO:9; and (iii) an LCDR3 comprising or consisting of the amino acid sequence of SEQ ID NO:10.

In some embodiments, the $V_H$ domain of the anti-PD-L1 scFv comprises an amino acid sequence with at least 90%, at least 95%, at least 96%, at least 97%, at least 98%, or at least 99% identity to SEQ ID NO: 3; and (i) an HCDR1 comprising or consisting of the amino acid sequence of SEQ ID NO: 5; (ii) an HCDR2 comprising or consisting of the amino acid sequence of SEQ ID NO: 6; and (iii) an HCDR3 comprising or consisting of the amino acid sequence of SEQ ID NO:7. In some embodiments, the $V_H$ domain of the anti-PD-L1 scFv comprises the amino acid sequence of SEQ ID NO: 3; and (i) an HCDR1 comprising or consisting of the amino acid sequence of SEQ ID NO: 5; (ii) an HCDR2 comprising or consisting of the amino acid sequence of SEQ ID NO: 6; and (iii) an HCDR3 comprising or consisting of the amino acid sequence of SEQ ID NO:7. In some embodiments, the $V_H$ domain of the anti-PD-L1 scFv comprises the amino acid sequence of SEQ ID NO: 3 with one or more mutations relative thereto. For example, in some embodiments, the $V_H$ domain comprises 1, 2, 3, 4, 5, 6, 7, 8, 9, 10, or more mutations relative to SEQ ID NO: 3. In some embodiments, the $V_H$ domain of anti-PD-L1 scFv comprises the amino acid sequence of SEQ ID NO: 3 with 1-5, 5-10, 11-15, 15-20, 10-25, 25-30, or more than 30 mutations.

In some embodiments, the $V_L$ domain of the anti-PD-L1 scFv comprises an amino acid sequence with at least 90%, at least 95%, at least 96%, at least 97%, at least 98%, or at least 99% identity to SEQ ID NO: 4; and (i) an LCDR1 comprising or consisting of the amino acid sequence of SEQ ID NO:8; (ii) an LCDR2 comprising or consisting of the amino acid sequence of SEQ ID NO:9; and (iii) an LCDR3 comprising or consisting of the amino acid sequence of SEQ ID NO:10. In some embodiments, the $V_L$ domain of the anti-PD-L1 scFv comprises the amino acid sequence of SEQ ID NO: 4; and (i) an LCDR1 comprising or consisting of the amino acid sequence of SEQ ID NO:8; (ii) an LCDR2 comprising or consisting of the amino acid sequence of SEQ ID NO:9; and (iii) an LCDR3 comprising or consisting of the amino acid sequence of SEQ ID NO:10. In some embodiments, the $V_L$ domain of the anti-PD-L1 scFv comprises the amino acid sequence of SEQ ID NO: 4 with one or more mutations relative thereto. For example, in some embodiments, the $V_L$ domain comprises 1, 2, 3, 4, 5, 6, 7, 8, 9 or 10 mutations relative to SEQ ID NO: 4. In some embodiments, the $V_L$ domain of the anti-PD-L1 scFv comprises the amino acid sequence of SEQ ID NO: 4 with 1-5, 5-10, 11-15, 15-20, 10-25, 25-30, or more than 30 mutations.

Shiga Toxin Effector Region:

In some embodiments, the PD-L1-binding molecule comprises a Shiga toxin effector region that is capable of exhibiting at least one Shiga toxin function. In some embodiments, the Shiga toxin effector region is an enzymatically active, de-immunized Shiga-like toxin A1 Subunit (SLT-1-A1 V1).

The term "Shiga toxin" herein refers to two families of related toxins: Shiga toxin (Stx)/Shiga-like toxin 1 (SLT-1/Stx1) and Shiga-like toxin 2 (SLT-2/Stx2). Stx is produced by *Shigella dysenteriae*, while SLT-1 and SLT-2 are derived from *Escherichia coli*. Members of the Shiga toxin family share the same overall structure and mechanism of action (Engedal N et al., Microbial Biotech 4: 32-46 (2011)). For example, Stx, SLT-1 and SLT-2 display indistinguishable enzymatic activity in cell free systems (Head S et al., J Biol Chem 266: 3617-21 (1991); Tesh V et al., Infect Immun 61: 3392-402 (1993); Brigotti Metal., Toxicon 35:1431-1437 (1997)).

Stx, SLT-1, and SLT-2 are multimeric molecules comprised of two polypeptide subunits, A and B. The B Subunit is a pentamer that binds the toxin to glycolipids on host cell membranes and enters the cell via endocytosis. Once inside the cell, the A Subunit undergoes proteolytic cleavage and the reduction of an internal disulfide bond to generate the A1 Subunit and the A2 Subunit. The Shiga toxin or Shiga-like toxin A1 Subunits (e.g., SLT-1-A1) are N-glycosidases that catalytically inactivate the 28S ribosomal RNA subunit to inhibit protein synthesis.

As described herein, the phrase "Shiga toxin effector region" refers to a polypeptide derived from a Shiga toxin A Subunit or Shiga-like toxin A Subunit of the Shiga toxin family, which exhibits at least one Shiga toxin effector function. In some embodiments, the Shiga toxin effector region of the PD-L1-binding molecule is a Shiga toxin A Subunit, such as StxA. In some embodiments, the Shiga toxin effector region of the PD-L1-binding molecule is a Shiga-like toxin A Subunit, such as SLT-1A or SLT-2A. In some embodiments, the Shiga toxin effector region of the PD-L1-binding molecule is an A1 Subunit of SLT-1 (e.g., SLT-1-A1). In some embodiments, the Shiga toxin effector region of the PD-L1-binding molecule is an enzymatically active, de-immunized Shiga-like toxin A1 Subunit of SLT-1 (e.g., SLT-1-A1 V1).

In some embodiments, the Shiga toxin effector region of the PD-L1-binding molecule has one or more Shiga toxin effector functions. Shiga toxin effector functions include, e.g., promoting cell entry, deforming lipid membranes, stimulating clathrin-mediated endocytosis, directing retrograde transport, directing subcellular routing, avoiding intracellular degradation, catalytically inactivating ribosomes, effectuating cytotoxicity, and effectuating cytostatic effects.

In some embodiments, the PD-L1-binding molecule comprises a truncated Shiga-like toxin A Subunit. For example, in some embodiments, the PD-L1-binding molecule comprises a truncated Shiga-like toxin A Subunit which is shorter than a full-length Shiga-like toxin A Subunit. In some embodiments, the truncated Shiga-like toxin A Subunit is the Shiga-like toxin A1 Subunit (e.g., SLT-1-A1). Shiga-like toxin A Subunit truncations are catalytically active, capable of enzymatically inactivating ribosomes in vitro, and cytotoxic when expressed within a cell. In some embodiments, the Shiga toxin effector region of the PD-L1-binding molecule is an enzymatically active, de-immunized Shiga-like toxin A1 Subunit of SLT-1 (e.g., SLT-1-A1 V1).

In some embodiments, the Shiga toxin effector region of the PD-L1-binding molecule exhibits ribosome inhibition activity. In some embodiments, the ribosome inhibition activity of the Shiga toxin effector region results in death of a target cell. In some embodiments, the Shiga toxin effector region of the PD-L1-binding molecule is capable of exhibiting a ribosome inhibition activity with a half-maximal inhibitory concentration ($IC_{50}$) value of less than 10,000, 5,000, 1,000, 500, or 200 picomolar.

In some embodiments, the PD-L1-binding molecule comprises a Shiga toxin effector region comprising an amino acid sequence of SEQ ID NO: 12. In some embodiments, the PD-L1-binding molecule comprises a Shiga toxin effector region comprising an amino acid sequence with one or more mutations relative to SEQ ID NO: 12. In some embodiments, the PD-L1-binding molecule comprises a Shiga toxin effector region comprising an amino acid sequence with at least 90%, at least 95%, at least 96%, at least 97%, at least 98%, or at least 99% identity to SEQ ID NO: 12. In some embodiments, the PD-L1-binding molecule comprises a Shiga toxin effector region with an amino acid sequence of SEQ ID NO: 12 with one or more mutations, such as 2, 3, 4, 5, 6, 7, 8, or 10 or more mutations. In some embodiments, the Shiga toxin effector region comprises any one of SEQ ID NO: 12 with 1-5, 5-10, 11-15, 15-20, 10-25, 25-30, or more than 30 mutations. In some embodiments, mutations in the Shiga toxin effector region render the polypeptide catalytically inactive. In some embodiments, mutations in the Shiga toxin effector region do not affect the catalytic activity of the polypeptide. In some embodiments, mutations in the Shiga toxin effector region increase the catalytic activity of the polypeptide. In some embodiments, mutations in the Shiga toxin effector region decrease the catalytic activity of the polypeptide.

In some embodiments, the Shiga toxin effector region of the PD-L1 binding molecule is de-immunized compared to a wild-type or native Shiga toxin effector region. The de-immunized, Shiga toxin effector region may comprise a disruption of at least one, putative, endogenous, epitope region in order to reduce the antigenic and/or immunogenic potential of the Shiga toxin effector region after administration of the PD-L1-binding molecule to a subject. In some embodiments, the de-immunized Shiga toxin effector region comprises a disruption of an endogenous epitope or epitope region, such as, e.g., a B-cell and/or T-cell epitope. For example, truncating the carboxy-terminus of SLT-1A to amino acids 1-251 of SEQ ID NO: 37 removes two predicted B-cell epitope regions, two predicted CD4 positive (CD4+) T-cell epitopes, and a predicted, discontinuous, B-cell epitope. Truncating the amino-terminus of SLT-1A to 75-293 of SEQ ID NO: 37 removes at least three, predicted, B-cell epitope regions and three predicted CD4+ T-cell epitopes. Truncating both amino- and carboxy-terminals of SLT-1A to 75-251 of SEQ ID NO: 37 deletes at least five, predicted, B-cell epitope regions; four, putative, CD4+ T-cell epitopes; and one, predicted, discontinuous, B-cell epitope.

In some embodiments, the de-immunized, Shiga toxin effector region comprises a disruption of at least one epitope region. In some embodiments, the de-immunized, Shiga toxin effector region comprises a disruption of at least one epitope region described in WO 2015/113005 or WO 2015/113007. Methods of de-immunizing a Shiga toxin effector region are described in WO 2015/113005, WO 2015/113007, WO 2016/196344, and WO 2018/140427, and are incorporated by reference in their entirety.

The term "disruption" as used herein with regard to an epitope region refers to the deletion of at least one amino acid residue in an epitope region, inversion of two or more amino acid residues where at least one of the inverted amino acid residues is in an epitope region, insertion of at least one amino acid into an epitope region, and a substitution of at least one amino acid residue in an epitope region. An epitope region disruption by mutation includes amino acid substitutions with non-standard amino acids and/or non-natural amino acids. Epitope regions may alternatively be disrupted by mutations comprising the modification of an amino acid by the addition of a covalently-linked chemical structure which masks at least one amino acid in an epitope region, e.g., PEGylation, small molecule adjuvants, and site-specific albumination.

In some embodiments, the PD-L1-binding molecule comprises a truncated Shiga-like toxin A Subunit with at least one mutation, e.g., deletion, insertion, inversion, or substitution, in a provided epitope region (e.g., SLT-1-A1 V1). In some embodiments, the truncated Shiga-like toxin A Subunit comprises a deletion of at least one amino acid within an epitope region. In some embodiments, the truncated Shiga-like toxin A Subunit comprises an insertion of at least one amino acid within an epitope region. In some embodiments, the truncated Shiga-like toxin A Subunit comprises an inversion of amino acids, wherein at least one inverted amino acid is within an epitope region. In some embodiments, the truncated Shiga-like toxin A Subunit comprises a mutation, such as an amino acid substitution to a non-standard amino acid or an amino acid with a chemically modified side chain. In some embodiments, the truncated Shiga-like toxin A Subunit comprises at least one amino acid substitution selected from the group consisting of: A, G, V, L, I, P, C, M, F, S, D, N, Q, H, and K.

In some embodiments, the Shiga toxin effector region of the PD-L1-binding molecule comprises a protease-cleavage resistant motif. Protease-cleavage resistant motifs increase the stability of the Shiga toxin effector region, as well as other components of the PD-L1-binding molecule, e.g., the PD-L1-binding region.

Protease-cleavage resistant motifs can be generated in the Shiga toxin effector region of the PD-L1-binding molecule by altering one or more amino acid residues in the protease-cleavage motif. An alteration to an amino acid residue in the protease-cleavage motif (e.g., a furin-cleavage motif) includes a mutation in the protease-cleavage motif, such as, e.g., a deletion, insertion, inversion, substitution, and/or carboxy-terminal truncation of the protease-cleavage motif, as well as a post-translational modification, such as, e.g., as a result of glycosylation, albumination, and the like, which involve conjugating or linking a molecule to the functional group of an amino acid residue.

Protease-cleavage motifs, e.g., furin-cleavage motifs, can be identified by the skilled worker using standard techniques. In general, a peptide or protein comprising a surface accessible, dibasic amino acid motif with two positively charged, amino acids separated by two amino acid residues can be predicted to be sensitive to furin-cleavage with cleavage occurring at the carboxy bond of the last basic amino acid in the motif. For example, furin cleaves the minimal, consensus motif R-x-x-R (SEQ ID NO: 36).

T Cell Epitopes:

In some embodiments, the PD-L1 binding molecule comprises an embedded or inserted epitope. In some embodiments, the epitope is a heterologous, T-cell epitope, such as, e.g., an epitope considered heterologous to a Shiga toxin A Subunit or Shiga-like toxin A Subunit (e.g., SLT-1A).

A T-cell epitope is an antigenic peptide represented by a linear, amino acid sequence. Commonly, T-cell epitopes are peptides of eight to eleven amino acid residues; however, certain T-cell epitopes have lengths that are smaller than eight or larger than eleven amino acids. A heterologous, T-cell epitope is an epitope not already present in a wild-type Shiga toxin A Subunit or Shiga-like toxin A Subunit; a naturally occurring Shiga toxin A Subunit or Shiga-like toxin A Subunit; and/or a native, wild-type Shiga toxin effector region.

In some embodiments, the T-cell epitope of the PD-L1-binding molecule is highly immunogenic and elicits robust immune responses in vivo when displayed complexed with a MHC class I molecule on the surface of a cell. A PD-L1-binding molecule comprising one or more highly immunogenic T-cell epitopes is referred to herein as a hyper-immunized PD-L1-binding molecule. Methods of generating hyper-immunized PD-L1-binding molecules are described in WO 2015/113005.

In some embodiments, the T-cell epitope of the PD-L1-binding molecule is bound by a TCR with a binding affinity characterized by a $K_D$ of less than 10 mM (e.g. 1-100 as calculated using the formula in Stone J et al., Immunology 126: 165-76 (2009). However, it should be noted that the binding affinity within a given range between the WIC-epitope and TCR may not correlate with antigenicity and/or immunogenicity, due to factors like MHC-peptide-TCR complex stability, WIC-peptide density and MHC-independent functions of TCR cofactors such as CD8 co-receptor.

In some embodiments, the PD-L1-binding molecule comprises a human CD8+ T-cell epitope. In some embodiments, the human CD8+ T-cell epitope is a peptide having at least seven, eight, nine, or ten amino acid residues. In some embodiments, the human CD8+ T-cell epitope comprises nine amino acid residues. In some embodiments, the human CD8+ T-cell epitope is bound by a human TCR with a binding affinity characterized by a $K_D$ less than 10 mM (e.g. 1-100 μM). In some embodiments, the human CD8+ T-cell epitope has a binding affinity to an MHC class I molecule characterized by a dissociation constant ($K_D$) of $10^4$ molar or less. In some embodiments, the MHC class I-epitope-peptide complex has a binding affinity to a TCR characterized by a dissociation constant ($K_D$) of $10^{-4}$ molar or less.

In some embodiments, the PD-L1-binding molecule comprises a CD8+ T-cell epitope derived from human cytomegalovirus (HCMV) pp65 protein (amino acids 495-503). In some embodiments, the CD8+ T-cell epitope is an HLA-A*02 MHC-I-restricted epitope. In some embodiments, the PD-L1-binding molecule comprises a CD8+ T-cell epitope comprising an amino acid sequence of NLVPMVATV (SEQ ID NO: 15). In some embodiments, the PD-L1-binding molecule comprises a CD8+ T-cell epitope that consists of the amino acid sequence NLVPMVATV (SEQ ID NO: 15). In some embodiments, the HCMV pp65 T-cell epitope is located on the N-terminus of the PD-L1-binding molecule. In some embodiments, the HCMV pp65 T-cell epitope is located on the C-terminus of the PD-L1-binding molecule.

In some embodiments, the PD-L1-binding molecule is capable of delivering a T-cell epitope (e.g., a CD8+ T-cell epitope) to a target cell (e.g., a PD-L1 positive/H2A:A2 positive cell), wherein the epitope is heterologous to Shiga toxins. The heterologous epitope may be, for example, a viral epitope such as a CMV epitope. In some embodiments, the PD-L1-binding molecule can deliver a T-cell epitope (e.g., a CD8+ T-cell epitope) to the WIC class I system of a target cell for subsequent presentation to the surface of the target cell. The delivery and presentation of a CMV CD8+ T-cell epitope may re-direct endogenous CMV-specific cytotoxic T-cells (CTLs) to the target cells (e.g., tumor cells). Delivery of a viral CD8+ T-cell epitope (antigen) to re-direct endogenous CMV-specific T-cells to a target cell is referred to herein as "Antigen seeding technology" or simply "AST".

In some embodiments, the PD-L1-binding molecule comprises a carboxy-terminal CMV antigen. In some embodiments, the PD-L1-binding molecule delivers the CMV antigen to a target cell, and the antigen stimulates cytotoxic T lymphocytes.

In some embodiments, the PD-L1-binding molecule comprises a CD8+ T-cell epitope having an amino acid sequence of VTEHDTLLY (SEQ ID NO: 16). In some embodiments, the PD-L1-binding molecule comprises a CD8+ T-cell epitope having an amino acid sequence of SIINFEKYL (SEQ ID NO: 17). In some embodiments, the PD-L1-binding molecule comprises a CD8+ T-cell epitope having an amino acid sequence of GLDRNSGNY (SEQ ID NO: 18). In some embodiments, the PD-L1-binding molecule comprises a CD8+ T-cell epitope having an amino acid sequence of GVMTRGRLK (SEQ ID NO: 19). In some embodiments, the PD-L1-binding molecule comprises a CD8+ T-cell epitope having an amino acid sequence of GILGFVFTL (SEQ ID NO: 20). In some embodiments, the molecule comprises a CD8+ T-cell epitope having an amino acid sequence of ILRGSVAHK (SEQ ID NO: 21).

In some embodiments, the Shiga toxin effector region of the PD-L1-binding molecule comprises an embedded or inserted, heterologous, T-cell epitope, such as, e.g., a human CD8+ T-cell epitope. In some embodiments, the heterologous, T-cell epitope is embedded or inserted so as to disrupt an endogenous epitope or epitope region (e.g. a B-cell epitope and/or CD4+ T-cell epitope) present in the native or wild-type Shiga toxin effector region. In some embodiments, the heterologous, T-cell epitope is coupled to the N-terminus of the Shiga toxin effector region. In some embodiments, the heterologous, T-cell epitope is coupled to the C-terminus of the Shiga toxin effector region. In some embodiments, the heterologous, T-cell epitope is embedded or inserted into the Shiga toxin effector region to generate a CD8+ T cell hyper-immunized Shiga toxin effector region, e.g., a Shiga toxin effector region that elicits robust immune responses in vivo. Methods of generating hyper-immunized Shiga toxin effector regions are described in WO 2015/113005.

A heterologous, T-cell epitope-peptide may be incorporated into the PD-L1-binding molecule via numerous methods known to the skilled worker, including, e.g., the processes of creating one or more amino acid substitutions within the PD-L1-binding molecule, fusing one or more amino acids to the PD-L1-binding molecule, inserting one or more amino acids into the PD-L1-binding molecule, linking a peptide to the PD-L1-binding molecule, or any combination thereof. The result of such a method is the generation of a modified variant of the PD-L1-binding molecule which comprises one or more embedded or inserted, heterologous, T-cell epitopes.

T-cell epitopes may be derived from a number of source molecules for use as described herein. In some embodiments, the T-cell epitopes are derived from source molecules known to be capable of eliciting a vertebrate immune response. In some embodiments, the T-cell epitopes are derived from various naturally occurring proteins foreign to vertebrates, such as, e.g., proteins of pathogenic microorganisms and non-self, cancer antigens. In some embodiments, the T-cell epitopes are derived from synthetic molecules.

In some embodiments, the PD-L1-binding molecule comprises a T-cell epitope derived from a pathogenic microorganism. Pathogenic microorganisms contain numerous proteins with known antigenic and/or immunogenic epitopes. For example, there are numerous intracellular pathogens, such as viruses, bacteria, fungi, and single-cell eukaryotes, with well-studied antigenic proteins or peptides. T-cell epitopes can be selected or identified from human viruses or other intracellular pathogens, such as, e.g., bacteria like *mycobacterium*, fungi like toxoplasmae, and protists like trypanosomes.

In some embodiments, the PD-L1-binding molecule comprises a T-cell epitope derived from a virus, e.g., a viral peptide or viral protein. For example, numerous, human T-cell epitopes have been mapped to peptides within proteins from influenza A viruses, such as peptides in the proteins HA glycoproteins FE17, S139/1, CH65, C05, hemagglutinin 1 (HA1), hemagglutinin 2 (HA2), nonstructural protein 1 and 2 (NS1 and NS 2), matrix protein 1 and 2 (M1 and M2), nucleoprotein (NP), neuraminidase (NA)), and many of these peptides have been shown to elicit human immune responses, such as by using an ex vivo assay. Similarly, numerous, human T-cell epitopes have been mapped to peptide components of proteins from human cytomegaloviruses (HCMV), such as peptides in the proteins pp65 (UL83), UL128-131, immediate-early 1 (IE-1; UL123), glycoprotein B, tegument proteins, and many of these peptides have been shown to elicit human immune responses, such as by using ex vivo assays.

In some embodiments, the PD-L1-binding molecule comprises a T-cell epitope derived from a human cancer antigen. There are many antigenic T-cell epitopes identified or predicted to occur in human cancer or tumor cells. For example, T-cell epitopes have been predicted in human proteins commonly mutated or overexpressed in neoplastic cells, such as, e.g., ALK, CEA, N-acetylglucosaminyl-transferase V (GnT-V), HCA587, PD-L1/neu, MAGE, Melan-A/MART-1, MUC-1, p53, and TRAG-3. In addition, synthetic variants of T-cell epitopes from human cancer cells have been created.

In some embodiments, the PD-L1-binding molecule comprises multiple, immunogenic, T-cell epitopes for MHC class I presentation. In some embodiments, the Shiga toxin effector region of the PD-L1-binding molecule comprises multiple, immunogenic, T-cell epitopes for MHC class I presentation. In some embodiments, the PD-L1-binding molecule comprises at least one, at least two, at least three, at least four, at least five, or at least six T-cell epitopes for MHC class I presentation.

Linkers Connecting Components of the PD-L1-Binding Molecule:

The structural components or regions of the PD-L1-binding molecule, such as, e.g., the PD-L1-binding region and the Shiga toxin effector region, may be connected directly or indirectly via one or more linkers.

As used herein, the term "linker" refers to a domain linker that joins two protein domains together. For example, a "binding region linker" may be used to link a Shiga toxin effector region with a PD-L1-binding region, and an "scFv linker" may be used to link the $V_H$ and the $V_L$ in an scFv. A "cleavable spacer" is a type of linker that contains a cleavage site for one or more proteases. Linkers may be selected based on flexibility, rigidity, and/or cleavability. Generally, there are a number of suitable linkers that can be used, including proteinaceous (e.g., single amino acids, peptides, or polypeptides) and non-proteinaceous (e.g., chemical linkers), generated by recombinant techniques that allows for recombinant attachment of the two domains with sufficient length and flexibility to allow each domain to retain its biological function.

Proteinaceous linkers comprise one or more amino acids, peptides, and/or polypeptides. Flexible proteinaceous linkers are often greater than twelve amino acid residues long and rich in small, non-polar amino acid residues; polar amino acid residues; and/or hydrophilic amino acid residues, such as, e.g., glycines, serines, and threonines. Flexible proteinaceous linkers may be chosen to increase the spatial separation between components and/or to allow for intramolecular interactions between components. In some embodiments, the linker peptide can predominantly include the following amino acid residues: Gly, Ser, Ala, or Thr. The linker peptide should have a length that is adequate to link two molecules in such a way that they assume the correct conformation relative to one another so that they retain the desired activity. In some embodiments, the linker is a flexible proteinaceous linker. In some embodiments, the linker is a rigid proteinaceous linker. In some embodiments, the linker is from about 1 to about 50 amino acids in length. In some embodiments, the linker is from about 1 to about 30 amino acids in length. In some embodiments, the linker is from about 1 to about 20 amino acids in length. In some embodiments, the linker is from about 5 to about 10 amino acids in length. For example, various "GS" linkers are well-known to the skilled artisan and are composed of multiple glycines and/or one or more serines, sometimes in repeating units, such as, e.g., (GxS)n, (SxG)n, (GGGGS)n, and (G)n, in which x is 1 to 6 and n is 1 to 30 (See, e.g., WO 96/06641). Non-limiting examples of flexible proteinaceous linkers include GKSSGSGSESKS (SEQ ID NO: 22), EGKSSGSGSESKEF (SEQ ID NO: 23), GSTSGSGKSSEGKG (SEQ ID NO: 24), GSTSGSGKSSEGSGSTKG (SEQ ID NO: 25), GSTSGSGKPGSGEGSTKG (SEQ ID NO: 26), SRSSG (SEQ ID NO: 27), SGSSC (SEQ ID NO: 28), GSTSGSGKPGSGEGS (SEQ ID NO: 29), and EFPKPSTPPGSSGGAP (SEQ ID NO: 30).

In some embodiments, the PD-L1-binding molecule comprises a linker which connects a $V_H$ domain and a $V_L$ domain of the PD-L1-binding region (e.g., the PD-L1 scFv). In some embodiments, the scFv linker is a proteinaceous linker comprising glycine-serine repeats. In some embodiments, the scFv linker is comprised of about 5 to about 35 amino acids, for instance, about 5 to about 15 amino acids. In some embodiments, the scFv linker is comprised of 5 amino acids. Suitable scFv linkers include: GGS, GGGS (SEQ ID NO: 31), GGGGS (SEQ ID NO: 11), GGGGSGGG (SEQ ID NO: 32), GGSGGGG (SEQ ID NO: 33), GSTSGGGSGGGSGGGGSS (SEQ ID NO: 34), and GSTSGSGKPGSSEGSTKG (SEQ ID NO: 35). In some embodiments, the PD-L1-binding molecule comprises an scFv linker comprising the amino acid sequence of SEQ ID NO: 11.

In some embodiments, the Shiga toxin effector region and PD-L1-binding region are linked via a binding region linker. In some embodiments, the binding region linker is a proteinaceous linker comprising about 5 amino acids to about 25 amino acids. In some embodiments, the binding region linker is a proteinaceous linker comprising about 10 amino acids to about 20 amino acids. In some embodiments, the binding region linker is a proteinaceous linker comprising 16 amino acids. In some embodiments, the PD-L1-binding molecule comprises binding region linker comprising an amino acid sequence with at least 80%, at least 85%, or at least 90% identity to EFPKPSTPPGSSGGAP (SEQ ID NO: 13). In some embodiments, the binding region linker comprises the amino acid sequence of EFPKPSTPPGSSGGAP (SEQ ID NO: 13).

Suitable linkers may be chosen to allow for in vivo separation of components, such as, e.g., due to cleavage and/or environment-specific instability. In vivo cleavable proteinaceous linkers are capable of unlinking by proteolytic processing and/or reducing environments often at a specific site within an organism or inside a certain cell type. In vivo cleavable proteinaceous linkers often comprise protease sensitive motifs and/or disulfide bonds formed by one or more cysteine pairs. In vivo cleavable proteinaceous linkers may be designed to be sensitive to proteases that exist only at certain locations in an organism, compartments within a cell, and/or become active only under certain physiological or pathological conditions (such as, e.g., involving proteases with abnormally high levels, proteases overexpressed at certain disease sites, and proteases specifically expressed by a pathogenic microorganism).

In some embodiments, a linker may be used which comprises one or more protease sensitive sites to provide for cleavage by a protease present within a target cell.

Suitable linkers may include pH sensitive linkers. For example, certain suitable linkers may be chosen for their instability in lower pH environments to provide for dissociation inside a subcellular compartment of a target cell. For example, linkers that comprise one or more trityl groups, derivatized trityl groups, bismaleimideothoxy propane groups, adipic acid dihydrazide groups, and/or acid labile transferrin groups, may provide for release of components of the PD-L 1-binding molecules as described herein, e.g. a polypeptide component, in environments with specific pH ranges. Certain linkers may be chosen which are cleaved in pH ranges corresponding to physiological pH differences between tissues, such as, e.g., the pH of tumor tissue is lower than in healthy tissues, as described in U.S. Pat. No. 5,612,474.

In some embodiments, the PD-L1-binding molecule comprises a cleavable spacer linker. In some embodiments, the cleavable spacer linker comprises from about 2 amino acids to about 20 amino acids. In some embodiments, the cleavable spacer linker comprises from about 3 amino acids to about 10 amino acids. In some embodiments, the cleavable spacer linker comprises 3, 4, 5, 6, 7, 8, 9, or 10 amino acids. In some embodiments, the PD-L1-binding molecule comprises a cleavable spacer linker comprising the amino acid sequence of HHAA (SEQ ID NO: 14).

Exemplary PD-L1-Binding Molecules:

In some embodiments, the PD-L1-binding molecule comprises: (i) a Shiga toxin effector region; (ii) a PD-L1-binding region; and (iii) a T-cell epitope. In some embodiments, the PD-L1-binding molecule comprises from amino to carboxy terminus: (i) a Shiga toxin effector region; (ii) a PD-L1-binding region; and (iii) a T-cell epitope.

In some embodiments, the PD-L1-binding molecule comprises from amino to carboxy terminus: (i) an enzymatically active de-immunized Shiga-like toxin-1-A1 Subunit (SLT-1-A1 V1); (ii) a murine anti-PD-L1 scFv; and (iii) an HLA-A*02 immunodominant MHC-I restricted T-cell epitope derived from the human cytomegalovirus (HCMV) pp65 protein (amino acids 495-503). In some embodiments, the PD-L1-binding molecule is produced as a single unglycosylated polypeptide chain of 514 amino acids (SEQ ID NO: 1) with a molecular weight of 55.8 kDa. In some embodiments, the PD-L1-binding molecule comprises two intra-chain disulfide bonds at C290-C362 and C418-C482. In some embodiments, the PD-L1-binding molecule forms a non-covalent dimer with a molecular weight of 112 kD.

In some embodiments, the PD-L1-binding molecule comprises one or more intra-chain disulfide bonds. In some embodiments, the PD-L1-binding molecule comprises one, two, three, four, five, or six intra-chain disulfide bonds. In some embodiments, the PD-L1-binding molecule comprises two intra-chain disulfide bonds. In some embodiments, the PD-L1-binding molecule comprises an intra-chain disulfide bond at C290-C362 and/or C418-C482. In some embodiments, the PD-L1-binding molecule does not comprise any intra-chain disulfide bonds.

In some embodiments, the PD-L1-binding molecule comprises a single polypeptide with a molecular mass of about 45 kDa to about 65 kDa. In some embodiments, the PD-L1-binding molecule comprises a single polypeptide with a molecular mass of about 45 kDa to about 65 kDa, about 50 kDa to about 65 kDa, about 55 kDa to about 65 kDa, or about 60 kDa to about 65 kDa. In some embodiments, the PD-L1-binding molecule comprises a single polypeptide with a molecular mass of about 45 kDa to about 60 kDa, about 45 kDa to about 55 kDa, or about 45 kDa to about 50 kDa. In some embodiments, the PD-L1-binding molecule comprises a single polypeptide with a molecular mass of about 45 kDa, about 46 kDa, about 47 kDa, about 48 kDa, about 49 kDa, about 50 kDa, about 51 kDa, about 52 kDa, about 53 kDa, about 54 kDa, about 55 kDa, about 56 kDa, about 57 kDa, about 58 kDa, about 59 kDa, about 60 kDa, about 61 kDa, about 62 kDa, about 63 kDa, about 64 kDa, or about 65 kDa. In some embodiments, the PD-L1-binding molecule comprises a single polypeptide with a molecular mass of 55.8 kDa.

In some embodiments, the PD-L1-binding molecule comprises two identical, non-covalently linked polypeptides each having a molecular mass of about 100 kDa to about 120 kDa. In some embodiments, the PD-L1-binding molecule comprises two identical, non-covalently linked polypeptides each having a molecular mass of about 100 kDa to about 120 kDa, about 105 kDa to about 120 kDa, about 110 kDa to about 120 kDa, or about 115 kDa to about 120 kDa. In some embodiments, the PD-L1-binding molecule comprises two identical, non-covalently linked polypeptides each having a molecular mass of about 100 kDa to about 115 kDa, about 100 kDa to about 110 kDa, or about 100 kDa to about 105 kDa. In some embodiments, the PD-L1-binding molecule comprises two identical, non-covalently linked polypeptides each having a molecular mass of about 105 kDa, about 106 kDa, about 107 kDa, about 108 kDa, about 109 kDa, about 110 kDa, about 111 kDa, about 112 kDa, about 113 kDa, about 114 kDa, or about 115 kDa. In some embodiments, the PD-L1-binding molecule comprises two identical, non-covalently linked polypeptides each having a molecular mass of about 112 kDa.

In some embodiments, the PD-L1-binding molecule comprises an amino acid sequence with at least 90%, at least 95%, at least 96%, at least 97%, at least 98%, or at least 99% identity to SEQ ID NO: 1. In some embodiments, the PD-L1-binding molecule comprises an amino acid sequence of SEQ ID NO: 1. In some embodiments, the PD-L1-binding molecule comprises an amino acid sequence of SEQ ID NO: 1 with one or more mutations, such as 2, 3, 4, 5, 6, 7, 8, or 10, or more mutations. In some embodiments, the PD-L1-binding molecule comprises an amino acid sequence of SEQ ID NO: 1 with 1-5, 5-10, 11-5, 15-20, 10-25, 25-30, or more than 30 mutations.

For the PD-L1-binding molecules described herein, the specific order or orientation of the different components (e.g., the PD-L1-binding region or Shiga toxin effector region) is not fixed in relation to each other or the entire binding molecule unless specifically noted. The components of the PD-L1-binding molecule may be arranged in any order provided that the desired activities of the PD-L1-binding region and Shiga toxin effector region are not eliminated. Desired activities include providing the PD-L1-binding molecule with the ability to, e.g., bind PD-L1-expressing cells; rapidly induce cellular internalization; cause efficient internalization; intracellularly route to a desired subcellular compartment(s); cause cytostasis; cause cytotoxicity; selectively kill PD-L1-expressing cells; deliver exogenous materials into the interior of a cell; diagnosis a disease, disorder, or condition; and/or treat a disease, disorder, or condition in a subject in need thereof.

In some embodiments, the PD-L1-binding molecules are multimeric, being comprised of two or more PD-L1-binding molecules, such as, e.g., homodimers, homotrimers, and homotetramers, and the like. For example, two or more monovalent PD-L1-binding polypeptides may be combined to form a multivalent PD-L1-binding molecule.

The association or linkage between polypeptides of a multimeric PD-L1-binding molecule may include 1) one or more non-covalent interactions; 2) one or more post-translational, covalent interactions; 3) one or more, covalent chemical conjugations; and/or 4) one or more covalent interactions resulting in a single molecule comprising a non-linear polypeptide, such as, e.g., a branched or cyclic polypeptide structure.

In some embodiments, the PD-L1-binding molecule comprises one or more covalent bonds to stabilize the homodimeric or multimeric PD-L1-binding molecule (See e.g. Glockshuber R et al., *Biochemistry* 29: 1362-7 (1990)). In some embodiments, the PD-L1-binding molecule is stabilized using disulfide bridge(s) and/or by adding or removing cysteine residue(s) at certain positions to control the position(s) of certain disulfide bridges.

In some embodiments, the PD-L1-binding molecule comprises one or more chemical linkers to stabilize the homodimeric or multimeric PD-L1-binding molecule.

In some embodiments, the PD-L1-binding molecule comprises two or more (e.g., three, four, five, six, seven, or eight) polypeptides. In some embodiments, each of polypeptides comprises the sequence of SEQ ID NO: 1.

In some embodiments, the PD-L1-binding molecule is a homodimer comprising two identical polypeptides. In some embodiments, the PD-L1-binding molecule is a homodimer comprising two identical polypeptides, wherein each polypeptide comprises the amino acid sequence of SEQ ID NO: 1. In some embodiments, the two identical polypeptides are non-covalently linked to each other, for example, via the PD-L1-binding region.

In some embodiments, the homodimeric PD-L1-binding molecule exhibits properties which are more favorable than the properties of a monomeric PD-L1-binding molecule. For example, in some embodiments, a PD-L1 binding molecule in dimeric form may more efficiently deliver an antigenic epitope (i.e., a CD8+ T-cell epitope) to a target cell than a PD-L1 molecule in monomeric form.

In some embodiments, the PD-L1-binding molecule comprises an additional exogenous material. An "additional exogenous material" as used herein refers to one or more atoms or molecules that can be transported to the interior of a cell by a binding molecule. In some embodiments, an additional exogenous material is any material transported into the interior of a cell by a binding molecule, whether or not it is typically present in the native target cell or in a native Shiga toxin. In some embodiments, an additional exogenous material is a material that is not generally present in Shiga toxins and/or native target cells. Non-limiting examples of additional exogenous materials are radionuclides, peptides, detection promoting agents, proteins, small molecule chemotherapeutic agents, and polynucleotides.

Exemplary PD-L1-binding molecules and components thereof (e.g., the Shiga toxin effector region, anti-PD-L1-binding region, and linkers) are provided in Table 1 below.

TABLE 1

Illustrative PD-L1-Binding Molecules and Components Thereof

| Name | Amino Acid Sequence | SEQ ID NO. |
|---|---|---|
| PD-L1 Binding Molecule (116297) | MKEFTLDFSTAKTYV<br>DSLNVIRSAIGTPLQ<br>TISSGGTSLLMIDSG<br>IGDNLFAVDILGFDF<br>TLGRFNNLRLIVERN<br>NLYVTGFVNRTNNVF<br>YRFADFSHVTFPGTT<br>AVTLSADSSYTTLQR<br>VAGISRTGMQINRHS<br>LTTSYLDLMSHSGTS<br>LTQSVARAMLRFVTV<br>TAEALRFRQIQRGFR<br>TTLDDLSGASYVMTA<br>EDVDLTLNWGRLSSV<br>LPDYHGQDSVRVGRI<br>SFGSINAILGSVALI<br>LNSHHHASAVAAEFP<br>KPSTPPGSSGGAPEV<br>QLQQSGPELVKPGAS<br>VKISCKTSGYTFTEY | 1 |

TABLE 1-continued

Illustrative PD-L1-Binding Molecules and Components Thereof

| Name | Amino Acid Sequence | SEQ ID NO. |
|---|---|---|
| | TMHWVKQRHGKSLEW<br>IGGINPNNGGTWYNQ<br>KFKGKATLTVDKSSS<br>TAYMELRSLTSEDSA<br>VYFCARPYYYGSRED<br>YFDYWGQGTTLTVSS<br>GGGGSDIQMTQSPSS<br>LSASVGDRVTITCSA<br>SSSVSYMYWYQQKPR<br>SSPKPWIYLTSNLAS<br>GVPARFSGSGSGTSY<br>SLTISSMEAEDAATY<br>YCQQWSSNPPTFGGG<br>TKLELKHHAANLVPM<br>VATV | |
| anti-PD-L1 scFv (116297) | EVQLQQSGPELVKPG<br>ASVKISCKTSGYTFT<br>EYTMHWVKQRHGKSL<br>EWIGGINPNNGGTWY<br>NQKFKGKATLTVDKS<br>SSTAYMELRSLTSED<br>SAVYFCARPYYYGSR<br>EDYFDYWGQGTTLTV<br>SSGGGGSDIQMTQSP<br>SSLSASVGDRVTITC<br>SASSSVSYMYWYQQK<br>PRSSPKPWIYLTSNL<br>ASGVPARFSGSGSGT<br>SYSLTISSMEAEDAA<br>TYYCQQWSSNPPTFG<br>GGTKLELK | 2 |
| VH domain (116297) | EVQLQQSGPELVKPG<br>ASVKISCKTSGYTFT<br>EYTMHWVKQRHGKSL<br>EWIGGINPNNGGTWY<br>NQKFKGKATLTVDKS<br>SSTAYMELRSLTSED<br>SAVYFCARPYYYGSR<br>EDYFDYWGQGTTLTV<br>SS | o |
| VL domain (116297) | DIQMTQSPSSLSASV<br>GDRVTITCSASSSVS<br>YMYWYQQKPRSSPKP<br>WIYLTSNLASGVPAR<br>FSGSGSGTSYSLTIS<br>SMEAEDAATYYCQQW<br>SSNPPTFGGGTKLEL<br>K | 4 |
| HCDR1 (116297) | EYTMH | 5 |
| HCDR2 (116297) | GINPNNGGTWYNQKF<br>K | 6 |
| HCDR3 (116297) | PYYYGSREDYFDY | 7 |
| LCDR1 (116297) | SASSSVSYMY | 8 |
| LCDR2 (116297) | LTSNLAS | 9 |
| LCDR3 (116297) | QQWSSNPPT | 10 |

TABLE 1-continued

Illustrative PD-L1-Binding Molecules and Components Thereof

| Name | Amino Acid Sequence | SEQ ID NO. |
|---|---|---|
| scFv linker (116297) | GGGGS | 11 |
| Shiga Toxin | KEFTLDFSTAKTYVD SLNVIRSAIGTPLQT ISSGGTSLLMIDS | 12 |
| effector region, | GIGDNLFAVDILGFD FTLGRFNNLRLIVER NNLYVTGFVNRTN | |
| SLT-1-A1 V1 | NVFYRFADFSHVTFP GTTAVTLSADSSYTT LQRVAGISRTGMQ | |
| (116297) | INRHSLTTSYLDLMS HSGTSLTQSVARAML RFVTVTAEALRFRQI QRGFRTTLDDLSGAS YVMTAEDVDLTLNWG RLSSVLPDYHGQDSV RVGRISFGSINAILG SVALILNSHHHASAV AA | |
| Binding domain linker (116297) | EFPKPSTPPGSSGGA P | 13 |
| Cleavable Spacer (116297) | HHAA | 14 |
| T cell epitope (116297) | NLVPMVATV | 15 |
| T cell epitope | VTEHDTLLY | 16 |
| T cell epitope | SIINFEKYL | 17 |
| T cell epitope | GLDRNSGNY | 18 |
| T cell epitope | GVMTRGRLK | 19 |
| T cell epitope | GILGFVFTL | 20 |
| T cell epitope | ILRGSVAHK | 21 |
| Linker | GKSSGSGSESKS | 22 |
| Linker | EGKSSGSGSESKEF | 23 |
| Linker | GSTSGSGKSSEGKG | 24 |
| Linker | GSTSGSGKSSEGSGS TKG | 25 |
| Linker | GSTSGSGKPGSGEGS TKG | 26 |
| Linker | SRSSG | 27 |
| Linker | SGSSC | 28 |
| Linker | GSTSGSGKPGSGEGS | 29 |
| Linker | EFPKPSTPPGSSGGA P | 30 |

TABLE 1-continued

Illustrative PD-L1-Binding Molecules and Components Thereof

| Name | Amino Acid Sequence | SEQ ID NO. |
|---|---|---|
| Linker | GGGS | 31 |
| Linker | GGGGSGGG | 32 |
| Linker | GGSGGGG | 33 |
| Linker | GSTSGGGSGGGSGGG GSS | 34 |
| Linker | GSTSGSGKPGSSEGS TKG | 35 |
| Furin cleavage motif | R-x-x-R | 36 |
| SLT-1A (Full length) | KEFTLDFSTAKTYVD SLNVIRSAIGTPLQT ISSGGTSLLMIDSGS GDNLFAVDVRGIDPE EGRFNNLRLIVERNN LYVTGFVNRTNNVFY RFADFSHVTFPGTTA VTLSGDSSYTTLQRV AGISRTGMQINRHSL TTSYLDLMSHSGTSL TQSVARAMLRFVTVT AEALRFRQIQRGFRT TLDDLSGRSYVMTAE DVDLTLNWGRLSSVL PDYHGQDSVRVGRIS FGSINAILGSVALIL NCHHHASRVARMASD EFPSMCPADGRVRGI THNKILWDSSTLGAI LMRRTISS | 37 |
| StxA (Full length) | KEFTLDFSTAKTYVD SLNVIRSAIGTPLQT ISSGGTSLLMIDSGT GDNLFAVDVRGIDPE EGRFNNLRLIVERNN LYVTGFVNRTNNVFY RFADFSHVTFPGTTA VTLSGDSSYTTLQRV AGISRTGMQINRHSL TTSYLDLMSHSGTSL TQSVARAMLRFVTVT AEALRFRQIQRGFRT TLDDLSGRSYVMTAE DVDLTLNWGRLSSVL PDYHGQDSVRVGRIS FGSINAILGSVALIL NCHHHASRVARMASD EFPSMCPADGRVRGI THNKILWDSSTLGAI LMRRTISS | 38 |
| SLT-2A (Full length) | DEFTVDFSSQKSYVD SLNSIRSAISTPLGN ISQGGVSVSVINHVL GGNYISLNVRGLDPY SERFNHLRLIMERNN LYVAGFINTETNIFY RFSDFSHISVPDVIT VSMTTDSSYSSLQRI ADLERTGMQIGRHSL VGSYLDLMEFRGRSM TRASSRAMLRFVTVI AEALRFRQIQRGFRP ALSEASPLYTMTAQD VDLTLNWGRISNVLP EYRGEEGVRIGRISF | 39 |

TABLE 1-continued

| Illustrative PD-L1-Binding Molecules and Components Thereof | | |
|---|---|---|
| Name | Amino Acid Sequence | SEQ ID NO. |
| | NSLSAILGSVAVILN CHSTGSYSVRSVSQK QKTECQIVGDRAAIK VNNVLWEANTIAALL NRKPQDLTEPNQ | |

Pharmaceutical Compositions

In some embodiments, the PD-L1-binding molecule may be formulated as a pharmaceutical composition for administration to a subject in need thereof (e.g., a subject with cancer or a solid tumor). In some embodiments, the pharmaceutical composition comprises a PD-L1-binding molecule comprising a polypeptide with the amino acid sequence of SEQ ID NO: 1.

In some embodiments, the pharmaceutical composition comprises a PD-L1-binding molecule at a concentration of about 0.1 mg/mL to about 100 mg/mL. In some embodiments, the concentration of the PD-L1-binding molecule is about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, about 2.0 mg/mL, about 2.5 mg/mL, about 3.0 mg/mL, about 3.5 mg/mL, about 4.0 mg/mL, about 4.5 mg/mL, about 5.0 mg/mL, about 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, about 9.5 mg/mL, about 10.0 mg/mL, about 20.0 mg/mL, about 30.0 mg/mL, about 40.0 mg/mL, about 50.0 mg/mL, about 60.0 mg/mL, about 70.0 mg/mL, about 80.0 mg/mL, about 90.0 mg/mL, or about 100.0 mg/mL. In some embodiments, the concentration of the PD-L1-binding molecule in the pharmaceutical composition is about 0.5 mg/mL. In some embodiments, the concentration of the PD-L1-binding molecule in the pharmaceutical composition is about 1 mg/mL.

In some embodiments, the concentration of the PD-L1-binding molecule in the pharmaceutical composition is 0.1±0.1 mg/mL to 10±0.1 mg/mL. In some embodiments, the concentration of the PD-L1-binding molecule in the pharmaceutical composition is 0.1±0.1 mg/mL, 0.5±0.1 mg/mL. 1.0±0.1 mg/mL, 1.5±0.1 mg/mL, 2.0±0.1 mg/mL, 2.5±0.1 mg/mL, 3.0±0.1 mg/mL, 3.5±0.1 mg/mL, 4.0±0.1 mg/mL, 4.5±0.1 mg/mL, 5.0±0.1 mg/mL, 5.5±0.1 mg/mL, 6.0±0.1 mg/mL, 6.5±0.1 mg/mL, 7.0±0.1 mg/mL, 7.5±0.1 mg/mL, 8.0±0.1 mg/mL, 8.5±0.1 mg/mL, 9.0±0.1 mg/mL, 9.5±0.1 mg/mL, or 10±0.1 mg/mL. In some embodiments, the concentration of the PD-L1-binding molecule in the pharmaceutical composition is 0.5±0.1 mg/mL. In some embodiments, the concentration of the PD-L1-binding molecule in the pharmaceutical composition is 1.0±0.1 mg/mL.

In some embodiments, the pharmaceutical composition comprises at least one pharmaceutically acceptable buffer. Non-limiting examples of suitable buffers include acetate, citrate, histidine, phosphate, histidine, Tris, tartrate, glycine, glutamate, and succinate buffers. In some embodiments, the pharmaceutical composition comprises an aqueous carrier comprising a pharmaceutically acceptable buffer. In some embodiments, the pharmaceutical composition comprises a salt and/or powder, such as, e.g. a freeze-dried, lyophilized, dehydrated, and/or cryodesiccated composition comprising a pharmaceutically acceptable buffer (e.g., sodium citrate). In some embodiments, the pharmaceutical composition comprises an aqueous citrate buffer.

In some embodiments, the pharmaceutical composition comprises at least one additional pharmaceutically acceptable carrier. Pharmaceutically acceptable carriers for therapeutic use are well known in the pharmaceutical art, and are described, for example, in *Remington's Pharmaceutical Sciences* (Mack Publishing Co. (A. Gennaro, ed., 1985)). Illustrative pharmaceutically acceptable carriers include sterile aqueous solutions or dispersions and sterile powders for the preparation of sterile injectable solutions or dispersions. Examples of suitable aqueous and nonaqueous carriers that may be used in the pharmaceutical compositions described herein include water, ethanol, polyols (e.g., glycerol, propylene glycol, and polyethylene glycol), and suitable mixtures thereof, such as vegetable oils and injectable organic esters.

In some embodiments, the pharmaceutical composition comprises at least one additional pharmaceutically acceptable excipient. Non-limiting examples of a pharmaceutically acceptable excipients include arginine, arginine sulfate, citric acid, glycerol, hydrochloric acid, mannitol, methionine, polysorbate, sodium chloride, sodium citrate, sodium hydroxide, sorbitol, sucrose, trehalose, and/or water.

In some embodiments, the pharmaceutical composition comprises at least one additional pharmaceutically acceptable salt. Examples of pharmaceutically acceptable salts include, but are not limited to, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts are further described in P. Heinrich Stahl, Camille G. Wermuth (Eds.), Handbook of Pharmaceutical Salts Properties, Selection, and Use; 2002.

In some embodiments, the pharmaceutical composition comprises one or more adjuvants such as preservatives, wetting agents, emulsifying agents and dispersing agents. Preventing the presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

In some embodiments, the pharmaceutical composition comprises one or more pharmaceutically acceptable antioxidants. Illustrative pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

In some embodiments, the pharmaceutical composition comprises one or more pharmaceutically acceptable isotonic agents or tonicity-adjusting agents. Non-limiting examples of suitable isotonic agents include sugars (e.g., dextrose), sugar alcohols, sodium chloride, and the like. Further examples of suitable sugars include disaccharides like sucrose and trehalose. Illustrative, pharmaceutically acceptable sugar alcohols include glycerol, mannitol, and sorbitol. In some embodiments, the pharmaceutical composition comprises an aqueous carrier and a pharmaceutically acceptable isotonic agent.

In some embodiments, the pharmaceutical composition comprises one or more pharmaceutically acceptable surfactants and/or emulsifying agents (emulsifiers). Non-limiting examples of suitable surfactants and/or emulsifiers include polysorbates such as, e.g., polyoxyethylene (20) sorbitan monolaurate (polysorbate 20), polyoxyethylene (20) sorbitan monopalmitate (polysorbate 40), polyoxyethylene (20) sorbitan monostearate (polysorbate 60), and (polyoxyethylene (20) sorbitan monooleate (polysorbate 80).

In some embodiments, the pharmaceutical composition comprises one or more pharmaceutically acceptable preservative agents. Non-limiting examples of antibacterial and antifungal agents include paraben, chlorobutanol, and phenol sorbic acid.

In some embodiments, the pharmaceutical composition comprises one or more pharmaceutically acceptable cryoprotective agents, also referred to as cryoprotectants or cryogenic protectants. Non-limiting examples of suitable cryoprotectants include ethylene glycol, glycerol, sorbitol, sucrose, and trehalose.

In some embodiments, the pharmaceutical composition comprises a buffer, such as a citrate buffer, a histidine buffer, or a phosphate buffer. In some embodiments, concentration of the buffer is about 1 mM to about 100 mM. For example, the concentration of the buffer may be about 1 mM to about 50 mM, or about 5 mM to about 30 mM. In some embodiments, the concentration of the buffer may be about 5 mM, about 7.5 mM, about 10 mM, about 12.5 mM, about 15 mM, about 17.5 mM, about 20 mM, about 22.5 mM, about 25 mM, about 27.5 mM, or about 30 mM. In some embodiments, the concentration of the buffer may be about 20 mM.

In some embodiments, the pharmaceutical composition comprises a citrate buffer, wherein the concentration of the citrate buffer is about 1 to about 100 mM, such as about 20 mM. In some embodiments, the pharmaceutical composition comprises a histidine buffer, wherein the concentration of the histidine buffer is about 1 to about 100 mM, such as about 20 mM. In some embodiments, the pharmaceutical composition comprises a phosphate buffer, wherein the concentration of the phosphate buffer is about 1 to about 100 mM, such as about 20 mM.

In some embodiments, the pharmaceutical composition comprises an isotonicity agent. In some embodiments, the isotonicity agent is a sugar or a sugar alcohol. For example, the sugar or sugar alcohol may be sorbitol, sucrose, or trehalose.

In some embodiments, the pharmaceutical composition comprises sorbitol. In some embodiments, the pharmaceutical composition comprises sorbitol at a concentration of about 10 mM to about 500 mM or about 50 mM to about 300 mM. In some embodiments, the pharmaceutical composition comprises sorbitol at a concentration of about 50 mM, about 75 mM, about 100 mM, about 125 mM, about 150 mM, about 175 mM, about 200 mM, about 225 mM, about 250 mM, about 275 mM, or about 300 mM. In some embodiments, the pharmaceutical composition comprises sorbitol at a concentration of about 200 mM.

In some embodiments, the pharmaceutical composition comprises sucrose. In some embodiments, the pharmaceutical composition comprises sucrose at a concentration of about 10 mM to about 500 mM, or about 50 mM to about 300 mM. In some embodiments, the pharmaceutical composition comprises sucrose at a concentration of about 50 mM, about 75 mM, about 100 mM, about 125 mM, about 150 mM, about 175 mM, about 200 mM, about 225 mM, about 250 mM, about 275 mM, or about 300 mM. In some embodiments, the pharmaceutical composition comprises sucrose at a concentration of about 200 mM.

In some embodiments, the pharmaceutical composition comprises trehalose. In some embodiments, the pharmaceutical composition comprises trehalose at a concentration of about 10 mM to about 500 mM, or about 50 mM to about 300 mM. In some embodiments, the pharmaceutical composition comprises trehalose at a concentration of about 50 mM, about 75 mM, about 100 mM, about 125 mM, about 150 mM, about 175 mM, about 200 mM, about 225 mM, about 250 mM, about 275 mM, or about 300 mM. In some embodiments, the pharmaceutical composition comprises trehalose at a concentration of about 200 mM.

In some embodiments, the pharmaceutical composition comprises a surfactant. In some embodiments, the pharmaceutical composition comprises a surfactant at a concentration of about 0.0001% to about 1% (v/v), such as about 0.001% (v/v) to about 0.1% (v/v) or about 0.005% (v/v) to about 0.015% (v/v).

In some embodiments, the pharmaceutical composition comprises polysorbate-80. In some embodiments, the pharmaceutical composition comprises polysorbate-80 at a concentration of about 0.005% (v/v) to about 0.015% (v/v). For example, the pharmaceutical composition may comprise polysorbate-80 at a concentration of about 0.005%, about 0.01%, about 0.015%, about 0.02%, about 0.025%, about 0.03%, about 0.035%, about 0.04%, about 0.045%, or about 0.05% (v/v). In some embodiments, the pharmaceutical composition comprises polysorbate-80 at a concentration of about 0.01% (v/v).

In some embodiments, the pharmaceutical composition comprises one or more pharmaceutically acceptable salts. The pharmaceutically acceptable salts may be at a concentration of about 1 mM to about 500 mM, about 1 mM to about 100 mM, or about 10 to about 50 mM. In some embodiments, the pharmaceutical composition comprises sodium chloride at about 1 mM to about 100 mM, such as about 5 mM, about 10 mM, about 15 mM, about 20 mM, about 25 mM, about 40 mM, about 45 mM, about 50 mM, about 55 mM, about 60 mM, about 65 mM, about 70 mM, about 75 mM, about 80 mM, about 85 mM, about 90 mM, or about 95 mM. In some embodiments, the pharmaceutical composition comprises arginine at about 1 mM to about 100 mM, such as about 5 mM, about 10 mM, about 15 mM, about 20 mM, about 25 mM, about 40 mM, about 45 mM, about 50 mM, about 55 mM, about 60 mM, about 65 mM, about 70 mM, about 75 mM, about 80 mM, about 85 mM, about 90 mM, or about 95 mM.

Illustrative pharmaceutically acceptable carriers and/or excipients that may be used in the compositions described herein are also shown in Table 2.

TABLE 2

Illustrative pharmaceutically acceptable carriers and/or excipients

| Class of pharmaceutically acceptable carrier/excipient | Illustrative, Non-Limiting Examples |
| --- | --- |
| Co-solvents | Glycerol, propylene glycol, ethanol, low molecular weight polyethylene glycol |
| Surfactants | Anti-foaming agents (dimethicone, simethicone, ethylene glycol distearate, sorbitan tristearate), emulsifiers (polysorbate 20, polysorbate 40, polysorbate 80, polysorbate 60, polysorbate 65, propylene glycol monostearate, glyceryl monostearate, propylene glycol monolaurate, sorbitan stearate, diethylene glycol monostearate, sorbitan monooleate, Polyethylene glycol monooleate, sorbitan monolaurate, polyoxyethylene sorbitan monostearate, polyoxyethylene sorbitan tristearate), wetting agents (Diethylene glycol monolaurate, sorbitan monopalmitate, sucrose dioleate), detergents (Polyethylene glycol (400) monolaurate, polyoxyethylene sorbitan monolaurate, triethanolamine oleate, PEG-8 laurate), solubilizers (Polyoxyethylene sorbitan monooleate (Tween 80), polyoxyethylene sorbitan monopalmitate (Tween 60), sodium oleate, polyoxyethylene stearate, potassium oleate) |
| Preservatives | Antimicrobial preservatives (e.g., benzalkonium chloride, benzethonium chloride, benzyl alcohol, bronool, cetrimide, cetylpyridinium chloride, chlorhexidine, chlorbutanol, chlorocresol, chloroxylenol, cresol, ethyl alcohol, glycerine, hexeditine, imdurea, phenol, phenoxyethanol, phenylethyl alcohol, phenylmercuric nitrate, propylene glycol, thimierosal), antifungal preservatives (e.g., butyl paraben, methyl paraben, ethyl paraben, propyl paraben, benzoic acid, potassium sorbate, sodium benzoate, sodium propionate, sorbic acid) |
| Viscosity modifier / suspending agent | cellulose derivatives (e.g., methylcellulose, microcrystalline cellulose, carboxymethylcellulose, ethylcellulose, hydroxyethylcellulose, hydroxypropyl cellulose and hydroxypropyl methylcellulose etc), clays (e.g., hectorite, bentonite, aluminium and/or magnesium silicate), natural gums (e.g., acacia, guar gum, tragacanth, xanthan gum, alginates, carrageenan and locust bean gum), synthetic polymers (e.g., carbomers, polyvinyl pyrrolidone, polyvinyl alcohol and poloxamer), and miscellaneous compounds (e.g., colloidal silicon dioxide and silicates). |
| Buffers | Citrate, phosphate, acetate, succinate, histidine, Tris, tartrate, glycine, glutamate |
| Antioxidants | Alpha-tocopherol acetate, ascorbic acid, butylated hydroxytoluene (BHT), d-alpha-tocepherol, monothioglycerol, sodium bisulfite, sodium sulfite, acetone sodium bisulfite, ascorbyl palmitate, cysteine, nordihydroguaiaretic acid, sodium formaldehyde sulfoxylate, sodium thiosulfate, acetylcysteine, butylated hydroxyanisole (BHA), cysteine hydrochloride, dithiothreitol, propyl gallate, sodium metabisulfite, thiourea |
| Chelating agents | Ethylenediaminetetraacetic acid, calcium disodium edentate, edetic acid |
| Humectants | Propylene glycol, glycerol, polyethylene glycol, sorbitol |
| Emulsifying agents | Sodium lauryl sulfate, cetrimide, macrogol |
| Flocculating agents | Sodium chloride, potassium chloride, aluminum chloride, calcium salts, citrates, sulphates, potassium biphosphates |
| Isotonicity agent | Sugars (sucrose, trehalose) or sugar alcohols (e.g., mannitol, sorbitol), dextrose, glycerin, potassium chloride, sodium chloride, arginine |

In some embodiments, the pH of the pharmaceutical composition is adjusted with acids or bases, such as hydrochloric acid or sodium hydroxide, or buffers with acetate, citrate, citric acid, histidine, sodium citrate, succinate, phosphate, and the like. In some embodiments, the pH of the pharmaceutical composition is measured using a calibrated/certified pH meter. In some embodiments, the pharmaceutical composition has a pH of about 4.0 to about 8.0. In some embodiments, the pharmaceutical composition has a pH of about 5.2 to about 5.8. In some embodiments, the pharmaceutical composition has a pH of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments, the pharmaceutical composition has a pH of about 5.0. In some embodiments, the pharmaceutical composition has a pH of about 5.5. In some embodiments, the pharmaceutical composition has a pH of about 5.6. In some embodiments, the pharmaceutical composition has a pH of about 6.0.

In some embodiments, the pH in the pharmaceutical composition is adjusted with a base, e.g., sodium hydroxide. In some embodiments, the pH in the pharmaceutical composition is adjusted with an acid, e.g., hydrochloric acid.

In some embodiments, the osmolality of the pharmaceutical composition is determined using standard methods known in the art. In some embodiments, the osmolality of the pharmaceutical composition is determined by freezing point depression methodology using an osmometer. The term "osmolality" as used herein refers to the measure of solute concentration in a given amount of solvent (i.e., osmoles of solute per kilogram of solvent (Osm/kg). In some embodiments, the osmolality of the pharmaceutical composition is between about 50 mOsm/kg to about 1000 mOsm/kg. In some embodiments, the osmolality of the pharmaceutical composition is about 50 mOsm/kg, about 75 mOsm/kg, about 100 mOsm/kg, about 125 mOsm/kg, about 150 mOsm/kg, about 175 mOsm/kg, about 200 mOsm/kg, about 250 mOsm/kg, about 275 mOsm/kg, about 300 mOsm/kg, about 325 mOsm/kg, about 350 mOsm/kg, about 375 mOsm/kg, about 400 mOsm/kg, about 475 mOsm/kg, about 500 mOsm/kg, about 550 mOsm/kg, about 600 mOsm/kg, about 650 mOsm/kg, about 700 mOsm/kg, about 750 mOsm/kg, about 800 mOsm/kg, about 850 mOsm/kg, about 900 mOsm/kg, about 950 mOsm/kg, or about 1000 mOsm/kg. In some embodiments, the osmolality of the pharmaceutical composition is about 250 mOsm/kg.

In some embodiments, the pharmaceutical composition is contained in a container closure system. In some embodiments, the container closure system containing the pharmaceutical composition comprises a glass vial, a fluoropolymer coated stopper, and a flip-off cap seal.

The pharmaceutical composition can be formulated for administration systemically or locally. In some embodiments, the pharmaceutical composition may be formulated for administration orally, parenterally, sublingually, transdermally, rectally, transmucosally, topically, via inhalation, via buccal administration, intrapleurally, intravenously, intraarterially, intragastrically, nasally, intraperitoneally, subcutaneously, intramuscularly, intranasally intrathecally, and intraarticularly or combinations thereof. In some embodiments, the pharmaceutical composition is formulated for intravenous administration.

In some embodiments, the pharmaceutical composition is at least 75% (w/v) free of impurities. In some embodiments, the pharmaceutical composition described herein is at least 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8% 99.9%, or 100% (w/v) free of impurities. In some embodiments, the pharmaceutical composition is at least 98% (w/v) free of impurities. In some embodiments, the pharmaceutical composition is at least 99% (w/v) free of impurities.

In some embodiments, the pharmaceutical composition is more than 75% (w/v) free of impurities. In some embodiments, the pharmaceutical composition described herein is more than 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8% 99.9%, or 100% (w/v) free of impurities. In some embodiments, the pharmaceutical composition is more than 99% (w/v) free of impurities.

In some embodiments, the pharmaceutical composition comprises less than 25% (w/v) of endotoxin, bioburden, host cell protein, host cell DNA, kanamycin, triton X-100, protein L, and glucan. In some embodiments, the pharmaceutical composition comprises less than 25.0%, 24.0%, 23.0%, 22.0%, 21.0%, 20.0%, 19.0%, 18.0%, 17.0%, 16.0%, 15.0%, 14.0%, 13.0%, 12.0%, 11.0%, 10.0%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% (w/v) of endotoxin, bioburden, host cell protein, host cell DNA, kanamycin, triton X-100, protein L, and/or glucan. In some embodiments, the pharmaceutical composition comprises less than 1% (w/v) of endotoxin, bioburden, host cell protein, host cell DNA, kanamycin, triton X-100, protein L, and/or glucan.

In some embodiments, the pharmaceutical composition comprises not more than 25% (w/v) of endotoxin, bioburden, host cell protein, host cell DNA, kanamycin, triton X-100, protein L, and glucan. In some embodiments, the pharmaceutical composition comprises not more than 25.0%, 24.0%, 23.0%, 22.0%, 21.0%, 20.0%, 19.0%, 18.0%, 17.0%, 16.0%, 15.0%, 14.0%, 13.0%, 12.0%, 11.0%, 10.0%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% (w/v) of endotoxin, bioburden, host cell protein, host cell DNA, kanamycin, triton X-100, protein L, and/or glucan. In some embodiments, the pharmaceutical composition comprises not more than 1% (w/v) of endotoxin, bioburden, host cell protein, host cell DNA, kanamycin, triton X-100, protein L, and/or glucan.

In some embodiments, the pharmaceutical composition comprises endotoxin at a concentration of ≤10 EU/mL. In some embodiments, the pharmaceutical composition comprises endotoxin at a concentration of ≤10 EU/mL, ≤9 EU/mL, ≤8 EU/mL, ≤7 EU/mL, ≤6 EU/mL, ≤5 EU/mL, ≤4 EU/mL, ≤3 EU/mL, ≤2 EU/mL, ≤1 EU/mL, ≤0.5 EU/mL, ≤0.1 EU/mL, or ≤0.05 EU/mL. In some embodiments, the pharmaceutical composition comprises endotoxin at a concentration of ≤5 EU/mL. In some embodiments, the pharmaceutical composition comprises endotoxin at a concentration of ≤4 EU/mL. In some embodiments, the pharmaceutical composition comprises endotoxin at a concentration of ≤3 EU/mL. In some embodiments, the pharmaceutical composition comprises endotoxin at a concentration of ≤2 EU/mL. In some embodiments, the pharmaceutical composition comprises endotoxin at a concentration of ≤0.5 EU/mL.

In some embodiments, the pharmaceutical composition comprises bioburden at a concentration of ≤100 CFU/mL. In some embodiments, the pharmaceutical composition comprises bioburden at a concentration of ≤100 CFU/mL, ≤90 CFU/mL, ≤80 CFU/mL, ≤70 CFU/mL, ≤60 CFU/mL, ≤50 CFU/mL, ≤40 CFU/mL, ≤30 CFU/mL, ≤20 CFU/mL, ≤10 CFU/mL, ≤9 CFU/mL, ≤8 CFU/mL, ≤7 CFU/mL, ≤6 CFU/mL, ≤5 CFU/mL, ≤4 CFU/mL, ≤3 CFU/mL, ≤2 CFU/mL, ≤1 CFU/mL, ≤0.5 CFU/mL, or ≤0.1 CFU/mL. In some embodiments, the pharmaceutical composition comprises bioburden at a concentration of ≤1 CFU/mL. In some embodiments, the bioburden concentration in the pharmaceutical composition is a total aerobic microbial count. In some embodiments, the bioburden concentration in the pharmaceutical composition is a total yeast and mold count.

In some embodiments, the pharmaceutical composition comprises host cell protein at a concentration of ≤1000 ng/mL. In some embodiments, the pharmaceutical composition comprises host cell protein at a concentration of ≤1000 ng/mL, ≤900 ng/mL, ≤800 ng/mL, ≤700 ng/mL, ≤600 ng/mL, ≤500 ng/mL, ≤400 ng/mL, ≤300 ng/mL, ≤200 ng/mL, ≤100 ng/mL, ≤75 ng/mL, ≤50 ng/mL, ≤25 ng/mL, ≤10 ng/mL, ≤5 ng/mL, ≤1 ng/mL, ≤0.05 ng/mL, or ≤0.01 ng/mL. In some embodiments, the pharmaceutical composition comprises host cell protein at a concentration of ≤1 ng/mL.

In some embodiments, the pharmaceutical composition comprises host cell DNA at a concentration of ≤1000 ng/mL. In some embodiments, the pharmaceutical composition comprises host cell DNA at a concentration of ≤1000 ng/mL, ≤900 ng/mL, ≤800 ng/mL, ≤700 ng/mL, ≤600 ng/mL, ≤500 ng/mL, ≤400 ng/mL, ≤300 ng/mL, ≤200 ng/mL, ≤100 ng/mL, ≤50 ng/mL, ≤25 ng/mL, ≤10 ng/mL, ≤9 ng/mL, ≤8 ng/mL, ≤7 ng/mL, ≤6 ng/mL, ≤5 ng/mL, ≤4 ng/mL, ≤3 ng/mL, ≤2 ng/mL, ≤1 ng/mL, ≤0.9 ng/mL, ≤0.8 ng/mL, ≤0.7 ng/mL, ≤0.6 ng/mL, ≤0.5 ng/mL, ≤0.4 ng/mL, ≤0.3 ng/mL, ≤0.2 ng/mL, ≤0.1 ng/mL, ≤0.09 ng/mL, ≤0.08 ng/mL, ≤0.07 ng/mL, ≤0.06 ng/mL, ≤0.05 ng/mL, ≤0.04 ng/mL, ≤0.03 ng/mL, ≤0.02 ng/mL, or ≤0.01 ng/mL. In some embodiments, the pharmaceutical composition comprises host cell DNA at a concentration of ≤0.1 ng/mL.

In some embodiments, the pharmaceutical composition comprises kanamycin at a concentration of ≤10,000 ng/mL. In some embodiments, the pharmaceutical composition comprises kanamycin at a concentration of ≤10,000 ng/mL, ≤9,000 ng/mL, ≤8,000 ng/mL, ≤7,000 ng/mL, ≤6,000 ng/mL, ≤5,000 ng/mL, ≤4,000 ng/mL, ≤3,000 ng/mL, ≤2,000 ng/mL, ≤1000 ng/mL, ≤900 ng/mL, ≤800 ng/mL, ≤700 ng/mL, ≤600 ng/mL, ≤500 ng/mL, ≤400 ng/mL, ≤300 ng/mL, ≤200 ng/mL, ≤100 ng/mL, ≤50 ng/mL, ≤25 ng/mL, ≤10 ng/mL, or ≤1 ng/mL. In some embodiments, the pharmaceutical composition comprises kanamycin at a concentration of ≤250 ng/mL. In some embodiments, the pharmaceutical composition comprises kanamycin at a concentration of ≤50 ng/mL.

In some embodiments, the pharmaceutical composition comprises triton X-100 at a concentration of ≤10,000 ng/mL. In some embodiments, the pharmaceutical composition comprises triton X-100 at a concentration of ≤10,000 ng/mL, ≤9,000 ng/mL, ≤8,000 ng/mL, ≤7,000 ng/mL, ≤6,000 ng/mL, ≤5,000 ng/mL, ≤4,500 ng/mL, ≤4,000 ng/mL, ≤3,500 ng/mL, ≤3,000 ng/mL, ≤2,500 ng/mL, ≤2,000 ng/mL, ≤1,500 ng/mL, ≤1,000 ng/mL, ≤900 ng/mL, ≤800 ng/mL, ≤700 ng/mL, ≤600 ng/mL, ≤500 ng/mL, ≤400 ng/mL, ≤300 ng/mL, ≤200 ng/mL, ≤100 ng/mL, ≤50 ng/mL, ≤25 ng/mL, ≤10 ng/mL, or ≤1 ng/mL. In some embodiments, the pharmaceutical composition comprises triton X-100 at a concentration of ≤250 ng/mL.

In some embodiments, the pharmaceutical composition comprises protein L at a concentration of ≤5,000 ng/mL. In some embodiments, the pharmaceutical composition comprises protein L at a concentration of ≤5,000 ng/mL, ≤4,500 ng/mL, ≤4,000 ng/mL, ≤3,500 ng/mL, ≤3,000 ng/mL, ≤2,500 ng/mL, ≤2,000 ng/mL, ≤1,500 ng/mL, ≤1,000 ng/mL, ≤900 ng/mL, ≤800 ng/mL, ≤700 ng/mL, ≤600 ng/mL, ≤500 ng/mL, ≤400 ng/mL, ≤300 ng/mL, ≤200 ng/mL, ≤100 ng/mL, ≤75 ng/mL, ≤50 ng/mL, ≤25 ng/mL, ≤10 ng/mL, ≤5 ng/mL, ≤1 ng/mL, ≤0.5 ng/mL, ≤0.1 ng/mL, ≤0.05 ng/mL, ≤0.025 ng/mL, or ≤0.01 ng/mL. In some embodiments, the pharmaceutical composition comprises protein L at a concentration of ≤1 ng/mL. In some embodiments, the pharmaceutical composition comprises protein L at a concentration of ≤0.025 ng/mL.

In some embodiments, the pharmaceutical composition comprises glucan at a concentration of ≤1000 ng/mL. In some embodiments, the pharmaceutical composition comprises glucan at a concentration of ≤1000 ng/mL, ≤900 ng/mL, ≤800 ng/mL, ≤700 ng/mL, ≤600 ng/mL, ≤500 ng/mL, ≤400 ng/mL, ≤300 ng/mL, ≤200 ng/mL, ≤100 ng/mL, ≤75 ng/mL, 50 ng/mL, 25 ng/mL, ≤10 ng/mL, ≤9 ng/mL, ≤8 ng/mL, ≤7 ng/mL, ≤6 ng/mL, ≤5 ng/mL, ≤4 ng/mL, ≤3 ng/mL, ≤2 ng/mL, ≤1 ng/mL, ≤0.5 ng/mL, or ≤0.1 ng/mL. In some embodiments, the pharmaceutical composition comprises glucan at a concentration of ≤1 ng/mL.

In some embodiments, the pharmaceutical composition is sterile. In some embodiments, the sterility of the pharmaceutical composition is confirmed by the absence of microbial growth using standard methodology known to those skilled in the art. In some embodiments, the pharmaceutical composition comprises no detectable microbial growth.

In some embodiments, the pharmaceutical composition is a sterile aqueous solution comprised of a PD-L1-binding molecule (about 0.1 to about 1 mg/mL) formulated in an aqueous citrate buffer (about 10 mM to about 100 mM), sorbitol (about 10 mM to about 500 mM), and polysorbate-80 (about 0.0001 to about 0.1% v/v), at a pH of about 5.0 to about 6.0. In some embodiments, the pharmaceutical composition is a sterile aqueous solution comprised of a PD-L1-binding molecule (about 0.5 mg/mL) formulated in a citrate buffer (about 20 mM), sorbitol (about 200 mM), and polysorbate-80 (about 0.01% v/v), at a pH of about 5.5. In some embodiments, the PD-L1-binding molecule comprises an amino acid sequence of SEQ ID NO: 1.

In some embodiments, the pharmaceutical composition comprises visible particulates. In some embodiments, the pharmaceutical composition comprises visible particulates that are proteinaceous aggregates. In some embodiments, the pharmaceutical composition comprises visible particulates that are translucent to white, amorphous or fibrous particles. In some embodiments, the visible particulates in the pharmaceutical composition are aggregates of the PD-L1-binding molecule. In some embodiments, the visible particulates are removed from the pharmaceutical composition through filtration (e.g., passing the drug substance through a 0.2 μm polyethersulfone (PES) membrane filter).

In some embodiments, the pharmaceutical composition comprises less than about 10% aggregates. In some embodiments, the pharmaceutical composition comprises less than about 10%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% aggregates. In some embodiments, the pharmaceutical composition comprises less than about 1.5% aggregates. In some embodiments, the pharmaceutical composition comprises less than about 1.0% aggregates. In some embodiments, the pharmaceutical composition comprises less than about 0.5% aggregates.

In some embodiments, the pharmaceutical composition comprises no more than about 10% aggregates. In some embodiments, the pharmaceutical composition comprises no more than about 10%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% aggregates. In some embodiments, the pharmaceutical composition comprises no more than about 1.5% aggregates. In some embodiments, the pharmaceutical composition comprises no more than about 1.0% aggregates. In some embodiments, the pharmaceutical composition comprises no more than about 0.5% aggregates.

In some embodiments the pharmaceutical composition comprises visible particulates and the visible particulates exhibit an infrared spectra comprising absorption bands ranging from about 600 $cm^{-1}$ to about 3600 $cm^{-1}$, about 1000 $cm^{-1}$ to about 3600 $cm^{-1}$, about 1400 $cm^{-1}$ to about 3600 $cm^{-1}$, about 1800 $cm^{-1}$ to about 3600 $cm^{-1}$, about 1800 $cm^{-1}$ to about 3600 $cm^{-1}$, about 2400 $cm^{-1}$ to about 3600 $cm^{-1}$, about 2800 $cm^{-1}$ to about 3600 $cm^{-1}$, or about 3200 $cm^{-1}$ to about 3600 $cm^{-1}$. In some embodiments, the visible particulates exhibit infrared spectra comprising absorption bands of about 2500 $cm^{-1}$, about 2600 $cm^{-1}$, about 2700 $cm^{-1}$, about 2800 $cm^{-1}$, about 2900 $cm^{-1}$, about 3000 $cm^{-1}$, about 3100 $cm^{-1}$, about 3200 $cm^{-1}$, about 3300 $cm^{-1}$, about 3400 $cm^{-1}$, or about 3500 $cm^{-1}$. In some embodiments, the visible particulates exhibit an infrared spectra comprising absorption bands of about 600 $cm^{-1}$, about 700 $cm^{-1}$, about 800 $cm^{-1}$, about 900 $cm^{-1}$, about 1000 $cm^{-1}$, about 1100 $cm^{-1}$, about 1200 $cm^{-1}$, about 1300 $cm^{-1}$, about 1400 $cm^{-1}$, about 1500 $cm^{-1}$, about 1600 $cm^{-1}$, about 1700 $cm^{-1}$, or about 1800 $cm^{-1}$.

In some embodiments, the pharmaceutical composition is substantially stable for at least three months, at least four months, at least five months, at least six months, at least one year, at least two years, or at least five years at about −10° C. to about −25° C. In some embodiments, the pharmaceutical composition is substantially stable for at least three months at about −10° C. to about −25° C.

In some embodiments, the pharmaceutical composition is substantially stable after two, three, four, five, or six freeze/thaw cycles. In some embodiments, the pharmaceutical composition is substantially stable after two freeze/thaw cycles.

In some embodiments, the pharmaceutical composition is substantially stable for at least one month, at least two months, at least three months, at least four months, at least five months, at least six months, at least one year, at least two years, or at least five years at about 2° C. to about 8° C. In some embodiments, the pharmaceutical composition is substantially stable for at least 3 months at about 2° C. to about 8° C.

In some embodiments, the pharmaceutical composition is substantially stable for at least 4 hours, at least 6 hours, at least 8 hours, at least 12 hours, at least 16 hours, at least 24 hours, at least 36 hours, or at least 48 hours at room temperature. In some embodiments, the pharmaceutical composition is substantially stable for at least 24 hours at room temperature.

In some embodiments, the pharmaceutical composition comprises less than about 5% of protein-based particulates. In some embodiments, the pharmaceutical composition comprises less than 5%, 4%, 3%, 2%, 1%, 0.9%, 0.8%, 0.7%, 0.6%, 0.5%, 0.4%, 0.3%, 0.2%, 0.1%, 0.05%, or 0.01% of protein-based particulates. In some embodiments, the pharmaceutical composition comprises less than 1% of protein-based particulates.

In some embodiments, the pharmaceutical composition comprises not more than about 5% of protein-based particulates. In some embodiments, the pharmaceutical composition comprises not more than about 5%, 4%, 3%, 2%, 1%, 0.9%, 0.8%, 0.7%, 0.6%, 0.5%, 0.4%, 0.3%, 0.2%, 0.1%, 0.05%, or 0.01% of protein-based particulates. In some embodiments, the pharmaceutical composition comprises not more than about 1% of protein-based particulates.

In some embodiments, the potency of the pharmaceutical composition is about 10% to about 500% of a reference standard $IC_{50}$ value. In some embodiments, the potency of the pharmaceutical composition is about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 275%, about 300%, about 325%, about 350%, about 375%, about 400%, about 425%, about 450%, about 475%, or about 500% of a reference standard $IC_{50}$ value. In some embodiments, the potency of the pharmaceutical composition is about 50% to about 150% of a reference standard $IC_{50}$ value. In some embodiments, the potency of the pharmaceutical composition is about 120% of a reference standard $IC_{50}$ value. In some embodiments, the reference standard $IC_{50}$ value is a representative batch of the pharmaceutical composition. In some embodiments, the potency of the pharmaceutical composition is determined using a cytotoxicity assay. In some embodiments, the potency of the pharmaceutical composition is about 0.61 ng/mL.

In some embodiments, the potency of the pharmaceutical composition is about 10% to about 500% of a reference standard $CD_{50}$ value. In some embodiments, the potency of the pharmaceutical composition is about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 275%, about 300%, about 325%, about 350%, about 375%, about 400%, about 425%, about 450%, about 475%, or about 500% of a reference standard $CD_{50}$ value. In some embodiments, the potency of the pharmaceutical composition is about 50% to about 150% of a reference standard $CD_{50}$ value. In some embodiments, the potency of the pharmaceutical composition is about 120% of a reference standard $CD_{50}$ value. In some embodiments, the reference standard $CD_{50}$ value is the $CD_{50}$ value of a PD-L1-binding molecule (e.g., 116297) that is determined using a cytotoxicity assay. In some embodiments, the potency of the pharmaceutical composition is determined using a cytotoxicity assay. In some embodiments, the potency of the pharmaceutical composition is about 0.61 ng/mL.

In some embodiments, the pharmaceutical composition is diluted in about 1% to about 10% dextrose (e.g., about 5% dextrose) for intravenous administration to a subject. In some embodiments, the pharmaceutical composition is diluted in normal saline (about 0.1% to about 5% sodium chloride, such as about 0.9% sodium chloride) for intravenous administration to a subject. In some embodiments, the pharmaceutical composition is diluted with 5% dextrose or normal saline (0.9% sodium chloride) based on a subject's body weight. In some embodiments, the pharmaceutical composition is diluted 2-fold, 3-fold, 4-fold, 5-fold, 10-fold, 20-fold, 50-fold, or 100-fold in normal saline (0.9% sodium chloride). In some embodiments, the pharmaceutical composition is diluted 2-fold, 3-fold, 4-fold, 5-fold, 10-fold, 20-fold, 50-fold, or 100-fold in 5% dextrose. In some embodiments, the diluted pharmaceutical composition is stable at room temperature for up to 4 hours.

In some embodiments, the pharmaceutical composition is diluted to about 0.250 mg/mL to about 0.001 mg/mL in normal saline (0.9% sodium chloride). In some embodiments, the pharmaceutical composition is diluted to about 0.250 mg/mL, about 0.240 mg/mL, about 0.230 mg/mL, about 0.220 mg/mL, about 0.210 mg/mL, about 0.200 mg/mL, about 0.190 mg/mL, about 0.180 mg/mL, about 0.170 mg/mL, about 0.160 mg/mL, about 0.150 mg/mL, about 0.140 mg/mL, about 0.130 mg/mL, about 0.120 mg/mL, about 0.110 mg/mL, about 0.100 mg/mL, about 0.090 mg/mL, about 0.080 mg/mL, about 0.070 mg/mL, about 0.060 mg/mL, about 0.05 mg/mL, about 0.040 mg/mL, about 0.030 mg/mL, about 0.020 mg/mL, about 0.010 mg/mL, about 0.009 mg/mL, about 0.008 mg/mL, about 0.007 mg/mL, about 0.006 mg/mL, or about 0.005 mg/mL in normal saline (0.9% sodium chloride).

In some embodiments, the pharmaceutical composition is diluted to about 0.250 mg/mL to about 0.005 mg/mL in 5% dextrose. In some embodiments, the pharmaceutical composition is diluted to about 0.250 mg/mL, about 0.240 mg/mL, about 0.230 mg/mL, about 0.220 mg/mL, about 0.210 mg/mL, about 0.200 mg/mL, about 0.190 mg/mL, about 0.180 mg/mL, about 0.170 mg/mL, about 0.160 mg/mL, about 0.150 mg/mL, about 0.140 mg/mL, about 0.130 mg/mL, about 0.120 mg/mL, about 0.110 mg/mL, about 0.100 mg/mL, about 0.090 mg/mL, about 0.080 mg/mL, about 0.070 mg/mL, about 0.060 mg/mL, about 0.05 mg/mL, about 0.040 mg/mL, about 0.030 mg/mL, about 0.020 mg/mL, about 0.010 mg/mL, about 0.009 mg/mL, about 0.008 mg/mL, about 0.007 mg/mL, about 0.006 mg/mL, or about 0.005 mg/mL in 5% dextrose.

In some embodiments, the pharmaceutical composition is analyzed by liquid chromatography-mass spectrometry (LC-MS). In some embodiments, LC-MS is used to assess the identity of the pharmaceutical composition. In some embodiments, the pharmaceutical composition analyzed by LC-MS comprises a main peak. In some embodiments, the main peak is consistent with the reference standard. In some embodiments, the reference standard is a representative batch of the pharmaceutical composition.

In some embodiments, the pharmaceutical composition is analyzed by cation exchange chromatography. In some embodiments, cation exchange chromatography is used to assess the identity of the pharmaceutical composition. In some embodiments, the pharmaceutical composition analyzed by cation exchange chromatography comprises a main isoform peak, an acidic peak, and a basic peak. In some embodiments, the main isoform peak comprises about 25% to about 75% of the pharmaceutical composition. In some embodiments, the main isoform peak comprises about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% of the pharmaceutical composition. In some embodiments, the main isoform peak comprises about 50% of the pharmaceutical composition. In some embodiments, the main isoform peak comprises about 51.3% of the pharmaceutical composition. In some embodiments, the acidic peak comprises about 20% to about 70% of the pharmaceutical composition. In some embodiments, the acidic peak comprises about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% of the pharmaceutical composition. In some embodiments, the acidic peak comprises about 45% of the pharmaceutical composition. In some embodiments, the acidic peak comprises about 44.4% of the pharmaceutical composition. In some embodiments, the basic peak comprises about 0.1% to about 10% of the pharmaceutical composition. In some embodiments, the basic peak comprises 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9% or 10.0% of the pharmaceutical composition. In some embodiments, the basic peak comprises about 5% of the pharmaceutical composition. In some embodiments, the basic peak comprises about 4.34% of the pharmaceutical composition.

In some embodiments, the pharmaceutical composition is analyzed using size-exclusion high performance liquid chromatography (SE-HPLC). In some embodiments, SE-HPLC is used to assess purity of the pharmaceutical composition. In some embodiments, the pharmaceutical composition analyzed by SE-HPLC comprises a primary peak, a low molecular weight peak, and an aggregate peak. In some embodiments, the primary peak is a 116297 homodimer comprising about 80% to about 100% of the pharmaceutical composition. In some embodiments, the primary peak is a 116297 homodimer comprising about 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8% 99.9%, or 100% of the pharmaceutical composition. In some embodiments, the primary peak is a 116297 homodimer comprising more than 80% of the pharmaceutical composition. In some embodiments, the primary peak is a 116297 homodimer comprising about 98.2% of the pharmaceutical composition. In some embodiments, the low molecular weight peak comprises less than 20% of the pharmaceutical composition. In some embodiments, the low molecular weight peak comprises less than 20.0%, 19.0%, 18.0%, 17.0%, 16.0%, 15.0%, 14.0%, 13.0%, 12.0%, 11.0%, 10.0%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of the pharmaceutical composition. In some embodiments, the low molecular weight peak comprises about 0.6% of the pharmaceutical composition. In some embodiments, the aggregate peak comprises less than 20% of the pharmaceutical composition. In some embodiments, the aggregate peak comprises less than 20.0%, 19.0%, 18.0%, 17.0%, 16.0%, 15.0%, 14.0%, 13.0%, 12.0%, 11.0%, 10.0%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of the pharmaceutical composition. In some embodiments, the aggregate peak comprises about 0.5% of the pharmaceutical composition. In some embodiments, the aggregate peak comprises about 0.6% of the pharmaceutical composition.

In some embodiments, the pharmaceutical composition is analyzed by capillary gel electrophoresis. In some embodiments, capillary gel electrophoresis is used to assess purity of the pharmaceutical composition. In some embodiments, the pharmaceutical composition analyzed by capillary gel electrophoresis comprises a primary peak. In some embodiments, the primary peak comprises about 80% to about 100% of the pharmaceutical composition. In some embodiments, the primary peak comprises about 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8% 99.9%, or 100% of the pharmaceutical composition. In some embodiments, the primary peak comprises more than 75% of the pharmaceutical composition. In some embodiments, the primary peak comprises more than 80% of the pharmaceutical composition.

In some embodiments, the pharmaceutical composition is analyzed by cation exchange chromatography. In some embodiments, cation exchange chromatography is used to assess the identity of the pharmaceutical composition. In some embodiments, the pharmaceutical composition analyzed by cation exchange chromatography comprises a main isoform peak, an acidic peak, and a basic peak. In some embodiments, the main isoform peak comprises about 25% to about 75% of the pharmaceutical composition. In some embodiments, the main isoform peak comprises about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75% of the pharmaceutical composition. In some embodiments, the main isoform peak comprises about 50% of the pharmaceutical composition. In some embodiments, the main isoform peak comprises about 51.3% of the pharmaceutical composition. In some embodiments, the acidic peak comprises about 20% to about 70% of the pharmaceutical composition. In some embodiments, the acidic peak comprises about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% of the pharmaceutical composition. In some embodiments, the acidic peak comprises about 45% of the pharmaceutical composition. In some embodiments, the acidic peak comprises about 44.4% of the pharmaceutical composition. In some embodiments, the basic peak comprises about 0.1% to about 10% of the pharmaceutical composition. In some embodiments, the basic peak comprises 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9% or 10.0% of the pharmaceutical composition. In some embodiments, the basic peak comprises about 5% of the pharmaceutical composition. In some embodiments, the basic peak comprises about 4.34% of the pharmaceutical composition.

In some embodiments, the pharmaceutical composition is analyzed using size-exclusion high performance liquid chromatography (SE-HPLC). In some embodiments, SE-HPLC is used to assess purity of the pharmaceutical composition. In some embodiments, the pharmaceutical composition analyzed by SE-HPLC comprises a primary peak, a low molecular weight peak, and an aggregate peak. In some embodiments, the primary peak is a 116297 homodimer comprising about 80% to about 100% of the pharmaceutical composition. In some embodiments, the primary peak is a 116297 homodimer comprising about 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8% 99.9%, or 100% of the pharmaceutical composition. In some embodiments, the primary peak is a 116297 homodimer comprising more than 80% of the pharmaceutical composition. In some embodiments, the primary peak is a 116297 homodimer comprising about 98.2% of the pharmaceutical composition. In some embodiments, the low molecular weight peak comprises less than 20% of the pharmaceutical composition. In some embodiments, the low molecular weight peak comprises less than 20.0%, 19.0%, 18.0%, 17.0%, 16.0%, 15.0%, 14.0%, 13.0%, 12.0%, 11.0%, 10.0%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of the pharmaceutical composition. In some embodiments, the low molecular weight peak comprises about 0.6% of the pharmaceutical composition. In some embodiments, the aggregate peak comprises less than 20% of the pharmaceutical composition. In some embodiments, the aggregate peak comprises less than 20.0%, 19.0%, 18.0%, 17.0%, 16.0%, 15.0%, 14.0%, 13.0%, 12.0%, 11.0%, 10.0%, 9.0%, 8.0%, 7.0%, 6.0%, 5.0%, 4.9%, 4.8%, 4.7%, 4.6%, 4.5%, 4.4%, 4.3%, 4.2%, 4.1%, 4.0%, 3.9%, 3.8%, 3.7%, 3.6%, 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1% of the pharmaceutical composition. In some embodiments, the aggregate peak comprises about 0.5% of the pharmaceutical composition. In some embodiments, the aggregate peak comprises about 0.6% of the pharmaceutical composition.

In some embodiments, capillary gel electrophoresis is used to assess purity of the pharmaceutical composition. In some embodiments, the pharmaceutical composition analyzed by capillary gel electrophoresis comprises a primary peak. In some embodiments, the primary peak comprises about 80% to about 100% of the pharmaceutical composition. In some embodiments, the primary peak comprises about 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8% 99.9%, or 100% of the pharmaceutical composition. In some embodiments, the primary peak comprises more than 75% of the pharmaceutical composition. In some embodiments, the primary peak comprises more than 80% of the pharmaceutical composition.

General Functions of the PD-L1-Binding Molecules and Pharmaceutical Compositions Thereof The PD-L1-binding molecules described herein directly or indirectly kill target cells (e.g., PD-L1 positive tumor cells) for the treatment of cancer such as non-small cell lung cancer or squamous cell carcinoma of the head and neck.

In some embodiments, the PD-L1 binding molecule binds extracellular PD-L1 expressed on the cell membrane of a particular cell type (e.g., a PD-L1 positive tumor cell) and enters the target cell. Once internalized within a target cell, in some embodiments, the PD-L1-binding molecule kills the target cell via the action(s) of the Shiga toxin effector region. For example, once internalized within a target cell, the PD-L1-binding molecule is capable of routing an enzymatically active, cytotoxic, Shiga toxin effector region into the cytosol of the target cell, which directly kills the target cell. In another example, once internalized within a target cell, in some embodiments, the PD-L1 binding molecule delivers a CD8+ T-cell epitope to the MHC class I presentation pathway, leading to cell-surface presentation of the T-cell epitope complexed with a MHC class I molecule, and indirectly kills the target cell through CTL-mediated cytotoxicity.

In some embodiments, the PD-L1-binding molecule directly kills a target cell. In some embodiments, the PD-L1-binding molecule directly kills a target cell due to the presence of one or more Shiga toxin effector regions. In some embodiments, the Shiga toxin effector region of the PD-L1-binding molecule comprises an enzymatically active Shiga toxin region capable of directly killing a target cell once routed to the cytosol of the target cell.

In some embodiments, the PD-L1-binding molecule delivers a T-cell epitope, which is associated with the PD-L1-binding molecule, to an MHC class I molecule of a target cell. Delivery of an exogenous, T-cell epitope to the MHC class I molecule of a target cell can be used to induce the target cell to present the T-cell epitope in association with MHC class I molecules on the cell surface, which subsequently leads to the activation of CD8+ effector T-cells to attack and kill the target cell. Thus, targeted delivery of a T-cell epitope for antigen presentation is used herein as a mechanism for activating T-cell responses against the target cell (e.g., a tumor cell).

The presentation of an immunogenic T-cell epitope the MEW class I targets the presenting cell for killing by CTL-mediated lysis and also triggers immune stimulation in the local microenvironment, e.g., recruiting additional immune cells to the tumor microenvironment.

Methods for Use of the PD-L1-Binding Molecules and Pharmaceutical Compositions Thereof The PD-L1-binding molecules described herein can be used in the prevention and/or treatment of diseases, disorders, and conditions. In some embodiments, the PD-L1-binding molecules and pharmaceutical compositions thereof can be used to treat or slow the progression of solid tumor malignancies, such as non-small cell lung cancer or squamous cell carcinoma of the head and neck.

The effective amount of the pharmaceutical composition described herein will depend on the route of administration and the subject being treated. The effective amount and the method of administration can be tailored to achieve optimal efficacy, and may depend on such factors as weight, diet, and concurrent medication, as well as other factors well-known to those skilled in the art. The dosage sizes and dosing regimen most appropriate for human use may be guided by results obtained from clinical trials. In some embodiments, the effective amount is determined by conventional means by starting with a low dose and then increasing the dosage while monitoring the effects.

In some embodiments, a method for treating or slowing the progression of a solid tumor comprises administering to a subject in need thereof an effective amount of a PD-L1-binding molecule, wherein the PD-L1 binding molecule comprises a polypeptide having the sequence of SEQ ID NO: 1. In some embodiments, the PD-L1-binding molecule is a homodimer comprising two identical polypeptides, wherein each polypeptide comprises the amino acid sequence of SEQ ID NO: 1.

In some embodiments, the PD-L1-binding molecule is administered to the subject on multiple occasions. In some embodiments, the PD-L1-binding molecule is administered to the subject once per week, twice per week, three times per week, four times per week, five times per week, six times per week, seven times per week, once per month, twice per month, three times per month, four times per month, once every two months, once every three months, once every six months, or once per year. In some embodiments, the PD-L1-binding molecule is administered once per week, wherein the dose of the PD-L1-binding molecule is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight.

In some embodiments, the PD-L1-binding molecule is administered weekly during a first 28-day cycle, wherein the PD-L1-binding molecule is administered on days 1, 8, 15, and 22 of the first 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule weekly during a second 28-day cycle following the first 28-day cycle, wherein the PD-L1-binding molecule is administered on days 1, 8, 15, and 22 of the second 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule weekly during a third 28-day cycle following the first and second 28-day cycles, wherein the PD-L1-binding molecule is administered on days 1, 8, 15, and 22 of the third 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule weekly during a fourth 28-day cycle following the first, second, and third 28-day cycles, wherein the PD-L1-binding molecule is administered on days 1, 8, 15, and 22 of the fourth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule weekly during a fifth 28-day cycle following the first, second, third, and fourth 28-day cycles, wherein the PD-L1-binding molecule is administered on days 1, 8, 15, and 22 of the fifth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule weekly during a sixth 28-day cycle following the first, second, third, fourth, and fifth 28-day cycles, wherein the PD-L1-binding molecule is administered on days 1, 8, 15, and 22 of the sixth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule weekly for at least one additional 28-day cycle following the first, second, third, fourth, fifth, or sixth 28-day cycle, wherein the PD-L1-binding molecule is administered on days 1, 8, 15, and 22 of the at least one additional 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight.

In some embodiments, the PD-L1-binding molecule is administered weekly during a first 28-day cycle, wherein the PD-L1-binding molecule is administered on days 1, 8, 15, and 22 of the first 28-day cycle, and wherein each dose is in an amount of about 30 μg/kg of the subject's body weight. In some embodiments, the method further comprises administering the PD-L1-binding molecule weekly during a second 28-day cycle following the first 28-day cycle, wherein the PD-L1-binding molecule is administered on days 1, 8, 15, and 22 of the second 28-day cycle, and wherein each dose is in an amount of about 30 μg/kg of the subject's body weight. In some embodiments, the method further comprises administering the PD-L1-binding molecule weekly during a third 28-day cycle following the first and second 28-day cycles, wherein the PD-L1-binding molecule is administered on days 1, 8, 15, and 22 of the third 28-day cycle, and wherein each dose is in an amount of about 30 μg/kg of the subject's body weight. In some embodiments, the method further comprises administering the PD-L1-binding molecule weekly during a fourth 28-day cycle following the first, second, and third 28-day cycles, wherein the PD-L1-binding molecule is administered on days 1, 8, 15, and 22 of the fourth 28-day cycle, and wherein each dose is in an amount of about 30 μg/kg of the subject's body weight. In some embodiments, the method further comprises administering the PD-L1-binding molecule weekly during a fifth 28-day cycle following the first, second, third, and fourth 28-day cycles, wherein the PD-L1-binding molecule is administered on days 1, 8, 15, and 22 of the fifth 28-day cycle, and wherein each dose is in an amount of about 30 μg/kg of the subject's body weight. In some embodiments, the method further comprises administering the PD-L1-binding molecule weekly during a sixth 28-day cycle following the first, second, third, fourth, and fifth 28-day cycles, wherein the PD-L1-binding molecule is administered on days 1, 8, 15, and 22 of the sixth 28-day cycle, and wherein each dose is in an amount of about 30 μg/kg of the subject's body weight. In some embodiments, the method further comprises administering the PD-L1-binding molecule weekly for at least one additional 28-day cycle following the first, second, third, fourth, fifth, or sixth 28-day cycle, wherein the PD-L1-binding molecule is administered on days 1, 8, 15, and 22 of the at least one additional 28-day cycle, and wherein each dose is in an amount of about 30 μg/kg of the subject's body weight.

In some embodiments, the PD-L1-binding molecule is administered weekly during a first 28-day cycle, wherein the PD-L1-binding molecule is administered on days 1, 8, 15, and 22 of the first 28-day cycle, and wherein each dose is in an amount of about 16 μg/kg of the subject's body weight. In some embodiments, the method further comprises administering the PD-L1-binding molecule weekly during a second 28-day cycle following the first 28-day cycle, wherein the PD-L1-binding molecule is administered on days 1, 8, 15, and 22 of the second 28-day cycle, and wherein each dose is in an amount of about 16 μg/kg of the subject's body weight. In some embodiments, the method further comprises administering the PD-L1-binding molecule weekly during a third 28-day cycle following the first and second 28-day cycles, wherein the PD-L1-binding molecule is administered on days 1, 8, 15, and 22 of the third 28-day cycle, and wherein each dose is in an amount of about 16 μg/kg of the subject's body weight. In some embodiments, the method further comprises administering the PD-L1-binding molecule weekly during a fourth 28-day cycle following the first, second, and third 28-day cycles, wherein the PD-L1-binding molecule is administered on days 1, 8, 15, and 22 of the fourth 28-day cycle, and wherein each dose is in an amount of about 16 μg/kg of the subject's body weight. In some embodiments, the method further comprises administering the PD-L1-binding molecule weekly during a fifth 28-day cycle following the first, second, third, and fourth 28-day cycles, wherein the PD-L1-binding molecule is administered on days 1, 8, 15, and 22 of the fifth 28-day cycle, and wherein each dose is in an amount of about 16 μg/kg of the subject's body weight. In some embodiments, the method further comprises administering the PD-L1-binding molecule weekly during a sixth 28-day cycle following the first, second, third, fourth, and fifth 28-day cycles, wherein the PD-L1-binding molecule is administered on days 1, 8, 15, and 22 of the sixth 28-day cycle, and wherein each dose is in an amount of about 16 μg/kg of the subject's body weight. In some embodiments, the method further comprises administering the PD-L1-binding molecule weekly for at least one additional 28-day cycle following the first, second, third, fourth, fifth, or sixth 28-day cycle, wherein the PD-L1-binding molecule is administered on days 1, 8, 15, and 22 of the at least one additional 28-day cycle, and wherein each dose is in an amount of about 16 μg/kg of the subject's body weight.

In some embodiments, the PD-L1-binding molecule is administered weekly during a first 28-day cycle, wherein the PD-L1-binding molecule is administered on days 1, 8, 15, and 22 of the first 28-day cycle, and wherein each dose is in an amount of about 8 μg/kg of the subject's body weight. In some embodiments, the method further comprises administering the PD-L1-binding molecule weekly during a second 28-day cycle following the first 28-day cycle, wherein the PD-L1-binding molecule is administered on days 1, 8, 15, and 22 of the second 28-day cycle, and wherein each dose is in an amount of about 8 μg/kg of the subject's body weight. In some embodiments, the method further comprises administering the PD-L1-binding molecule weekly during a third 28-day cycle following the first and second 28-day cycles, wherein the PD-L1-binding molecule is administered on days 1, 8, 15, and 22 of the third 28-day cycle, and wherein each dose is in an amount of about 8 μg/kg of the subject's body weight. In some embodiments, the method further comprises administering the PD-L1-binding molecule weekly during a fourth 28-day cycle following the first, second, and third 28-day cycles, wherein the PD-L1-binding molecule is administered on days 1, 8, 15, and 22 of the fourth 28-day cycle, and wherein each dose is in an amount of about 8 μg/kg of the subject's body weight. In some embodiments, the method further comprises administering the PD-L1-binding molecule weekly during a fifth 28-day cycle following the first, second, third, and fourth 28-day cycles, wherein the PD-L1-binding molecule is administered on days 1, 8, 15, and 22 of the fifth 28-day cycle, and wherein each dose is in an amount of about 8 μg/kg of the subject's body weight. In some embodiments, the method further comprises administering the PD-L1-binding molecule weekly during a sixth 28-day cycle following the first, second, third, fourth, and fifth 28-day cycles, wherein the PD-L1-binding molecule is administered on days 1, 8, 15, and 22 of the sixth 28-day cycle, and wherein each dose is in an amount of about 8 μg/kg of the subject's body weight. In some embodiments, the method further comprises administering the PD-L1-binding molecule weekly for at least one additional 28-day cycle following the first, second, third, fourth, fifth, or sixth 28-day cycle, wherein the PD-L1-binding molecule is administered on days 1, 8, 15, and 22 of the at least one additional 28-day cycle, and wherein each dose is in an amount of about 8 μg/kg of the subject's body weight.

In some embodiments, the PD-L1-binding molecule is administered two times during a first 28-day cycle, wherein the PD-L1-binding molecule is administered on days 1 and 15 of the first 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule two times during a second 28-day cycle following the first 28-day cycle, wherein the PD-L1-binding molecule is administered on days 1 and 15 of the second 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule two times during a third 28-day cycle following the first and second 28-day cycles, wherein the PD-L1-binding molecule is administered on days 1 and 15 of the third 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule two times during a fourth 28-day cycle following the first, second, and third 28-day cycles, wherein the PD-L1-binding molecule is administered on days 1 and 15 of the fourth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule two times during a fifth 28-day cycle following the first, second, third, and fourth 28-day cycles, wherein the PD-L1-binding molecule is administered on days 1 and 15 of the fifth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule two times during a sixth 28-day cycle following the first, second, third, fourth, and fifth 28-day cycles, wherein the PD-L1-binding molecule is administered on days 1 and 15 of the sixth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule two times for at least one additional 28-day cycle following the first, second, third, fourth, fifth, or sixth 28-day cycle, wherein the PD-L1-binding molecule is administered on days 1 and 15 of the at least one additional 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight.

In some embodiments, the PD-L1-binding molecule is administered three times during a first 28-day cycle, wherein the PD-L1-binding molecule is administered on days 1, 8, and 15 of the first 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule three times during a second 28-day cycle following the first 28-day cycle, wherein the PD-L1-binding molecule is administered on days 1, 8, and 15 of the second 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule three times during a third 28-day cycle following the first and second 28-day cycles, wherein the PD-L1-binding molecule is administered on days 1, 8, and 15 of the third 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule three times during a fourth 28-day cycle following the first, second, and third 28-day cycles, wherein the PD-L1-binding molecule is administered on days 1, 8, and 15 of the fourth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule three times during a fifth 28-day cycle following the first, second, third, and fourth 28-day cycles, wherein the PD-L1-binding molecule is administered on days 1, 8, and 15 of the fifth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule three times during a sixth 28-day cycle following the first, second, third, fourth, and fifth 28-day cycles, wherein the PD-L1-binding molecule is administered on days 1, 8, and 15 of the sixth 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight. In some embodiments, the method further comprises administering the PD-L1-binding molecule three times for at least one additional 28-day cycle following the first, second, third, fourth, fifth, or sixth 28-day cycle, wherein the PD-L1-binding molecule is administered on days 1, 8, and 15 of the at least one additional 28-day cycle, and wherein each dose is in an amount of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight.

In some embodiments, the PD-L1-binding molecule is administered on days 0 and day 14. In some embodiments, the method further comprises administering the PD-L1 binding molecule on days 2, 4, 7, 9, 11, 16, 18, 21, 23, and 25. In some embodiments, the PD-L1-binding molecule is administered on days 0 and day 14, wherein each dose is in an amount of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. In some embodiments, the method further comprises administering the PD-L1 binding molecule on days 2, 4, 7, 9, 11, 16, 18, 21, 23, and 25 at a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. In some embodiments, the PD-L1-binding molecule is administered on days 0 and day 14, wherein each dose is in an amount of about 6 mg/kg. In some embodiments, the method further comprises administering the PD-L1 binding molecule on days 2, 4, 7, 9, 11, 16, 18, 21, 23, and 25 at a dose of about 2 mg/kg.

In some embodiments, the dose of the PD-L1-binding molecule is increased during the course of treatment. In some embodiments, the dose of the PD-L1-binding molecule is increased once per week, twice per week, three times per week, four times per week, five times per week, once every two weeks, once every three weeks, once per month, once every two months, once every three months, once every four months, once every five months, once every six months, or once per year during the course of treatment.

In some embodiments, the dose of the PD-L1-binding molecule is increased during a first 28-day cycle. In some embodiments, the dose of the PD-L1-binding molecule is increased during a second 28-day cycle following the first 28-day cycle. In some embodiments, the dose of the PD-L1-binding molecule is increased during a third 28-day cycle following the first and second 28-day cycles. In some embodiments, the dose of the PD-L1-binding molecule is increased during an at least one additional 28-day cycle following the first, second, and third 28-day cycles.

In some embodiments, a first dose and a second dose of a PD-L1-binding molecule are administered to a subject. In some embodiments, the second dose is higher than the first dose. For example, the second dose may be greater than the first dose by about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 3-fold, about 5-fold, about 10-fold, about 25-fold, or about 50-fold higher than the first dose, or more. In another example, the second dose may be greater than the first dose by about 110%, about 125%, about 133%, about 150%, about 175%, about 200%, about 225%, about 250%, about 275%, about 300%, or more.

In some embodiments, the dose of the PD-L1-binding molecule is increased from about 10 μg/kg to about 20 μg/kg, about 25 μg/kg, about 30 μg/kg, about 35 μg/kg, about 40 μg/kg, about 45 μg/kg, about 50 μg/kg, about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, or about 250 μg/kg of the subject's body weight. In some embodiments, the dose of the PD-L1-binding molecule is increased from about 20 μg/kg to about 25 μg/kg, about 30 μg/kg, about 35 μg/kg, about 40 μg/kg, about 45 μg/kg, about 50 μg/kg, about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, about 250 μg/kg, or about 275 μg/kg of the subject's body weight. In some embodiments, the dose of the PD-L1-binding molecule is increased from about 25 μg/kg to about 30 μg/kg, about 35 μg/kg, about 40 μg/kg, about 45 μg/kg, about 50 μg/kg, about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, about 250 μg/kg, or about 275 μg/kg of the subject's body weight. In some embodiments, the dose of the PD-L1-binding molecule is increased from about 30 μg/kg to about 35 μg/kg, about 40 μg/kg, about 45 μg/kg, about 50 μg/kg, about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, about 250 μg/kg, or about 275 μg/kg of the subject's body weight. In some embodiments, the dose of the PD-L1-binding molecule is increased from about 40 μg/kg to about 45 μg/kg, about 50 μg/kg, about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, about 250 μg/kg, or about 275 μg/kg of the subject's body weight. In some embodiments, the dose of the PD-L1-binding molecule is increased from about 50 μg/kg to about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, or about 400 μg/kg of the subject's body weight. In some embodiments, the dose of the PD-L1-binding molecule is increased from about 75 μg/kg to about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, or about 500 μg/kg of the subject's body weight.

In some embodiments, the dose of the PD-L1-binding molecule is decreased during the course of treatment. In some embodiments, the dose of the PD-L1-binding molecule is decreased once per week, twice per week, three times per week, four times per week, five times per week, once every two weeks, once every three weeks, once per month, once every two months, once every three months, once every four months, once every five months, once every six months, or once per year during the course of treatment.

In some embodiments, a first dose and a second dose of a PD-L1-binding molecule are administered to a subject. In some embodiments, the second dose is lower than the first dose. For example, the second dose may be lower than the first dose by about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 3-fold, about 5-fold, about 10-fold, about 25-fold, or about 50-fold higher than the first dose, or more. In another example, the second dose may be lower than the first dose by about 10%, about 25%, about 33%, about 50%, about 75%, or more.

In some embodiments, the dose of the PD-L1-binding molecule is decreased during a first 28-day cycle. In some embodiments, the dose of the PD-L1-binding molecule is decreased during a second 28-day cycle following the first 28-day cycle. In some embodiments, the dose of the PD-L1-binding molecule is decreased during a third 28-day cycle following the first and second 28-day cycles. In some embodiments, the dose of the PD-L1-binding molecule is decreased during an at least one additional 28-day cycle following the first, second, and third 28-day cycles.

In some embodiments, the dose of the PD-L1-binding molecule is decreased from about 10 μg/kg to about 5 μg/kg, about 2.5 μg/kg, about 1 μg/kg, about 0.5 μg/kg, about 0.1 μg/kg, about 0.05 μg/kg, or about 0.01 μg/kg of the subject's body weight. In some embodiments, the dose of the PD-L1-binding molecule is decreased from about 20 μg/kg to about 15 μg/kg, about 10 μg/kg, about 5 μg/kg, about 2.5 μg/kg, about 1 μg/kg, about 0.5 μg/kg, about 0.1 μg/kg, about 0.05 μg/kg, or about 0.01 μg/kg of the subject's body weight. In some embodiments, the dose of the PD-L1-binding molecule is decreased from about 25 μg/kg to about 20 μg/kg, about 15 μg/kg, about 10 μg/kg, about 5 μg/kg, about 2.5 μg/kg, about 1 μg/kg, about 0.5 μg/kg, about 0.1 μg/kg, about 0.05 μg/kg, or about 0.01 μg/kg of the subject's body weight. In some embodiments, the dose of the PD-L1-binding molecule is decreased from about 30 μg/kg to about 25 μg/kg to about 20 μg/kg, about 15 μg/kg, about 10 μg/kg, about 5 μg/kg, about 2.5 μg/kg, about 1 μg/kg, about 0.5 μg/kg, about 0.1 μg/kg, about 0.05 μg/kg, or about 0.01 μg/kg of the subject's body weight. In some embodiments, the dose of the PD-L1-binding molecule is decreased from about 40 μg/kg to about 35 μg/kg, about 30 μg/kg, about 25 μg/kg, about 20 μg/kg, about 15 μg/kg, about 10 μg/kg, about 5 μg/kg, about 2.5 μg/kg, about 1 μg/kg, about 0.5 μg/kg, about 0.1 μg/kg, about 0.05 μg/kg, or about 0.01 μg/kg of the subject's body weight. In some embodiments, the dose of the PD-L1-binding molecule is decreased from about 50 μg/kg to about 45 μg/kg, about 40 μg/kg, about 35 μg/kg, about 30 μg/kg, about 25 μg/kg, about 20 μg/kg, about 15 μg/kg, about 10 μg/kg, about 5 μg/kg, about 1 μg/kg, about 0.5 μg/kg, about 0.1 μg/kg, about 0.05 μg/kg, or about 0.01 μg/kg of the subject's body weight. In some embodiments, the dose of the PD-L1-binding molecule is decreased from about 75 μg/kg to about 70 μg/kg, about 65 μg/kg, about 60 μg/kg, about 55 μg/kg, about 50 μg/kg, about 45 μg/kg, about 40 μg/kg, about 35 μg/kg, about 30 μg/kg, about 25 μg/kg, about 20 μg/kg, about 15 μg/kg, about 10 μg/kg, about 5 μg/kg, about 1 μg/kg, about 0.5 μg/kg, about 0.1 μg/kg, about 0.05 μg/kg, or about 0.01 μg/kg of the subject's body weight. In some embodiments, the dose of the PD-L1-binding molecule is decreased from about 16 μg/kg to about 8 μg/kg of the subject's body weight.

In some embodiments, the amount of PD-L1-binding molecule administered to the subject in a single dose is about 1 μg/kg, about 2 μg/kg, about 3 μg/kg, about 4 μg/kg, about 5 μg/kg, about 6 μg/kg, about 7 μg/kg, about 8 μg/kg, about 9 μg/kg, about 10 μg/kg, about 11 μg/kg, about 12 μg/kg, about 13 μg/kg, about 14 μg/kg, about 15 μg/kg, about 16 μg/kg, about 17 μg/kg, about 18 μg/kg, about 19 μg/kg, about 20 μg/kg, about 21 μg/kg, about 22 μg/kg, about 23 μg/kg, about 24 μg/kg, about 25 μg/kg, about 26 μg/kg, about 27 μg/kg, about 28 μg/kg, about 29 μg/kg, about 30 μg/kg, about 31 μg/kg, about 32 μg/kg, about 33 μg/kg, about 34 μg/kg, about 35 μg/kg, about 36 μg/kg, about 37 μg/kg, about 38 μg/kg, about 39 μg/kg, about 40 μg/kg, about 41 μg/kg, about 42 μg/kg, about 43 μg/kg, about 44 μg/kg, about 45 μg/kg, about 46 μg/kg, about 47 μg/kg, about 48 μg/kg, about 49 μg/kg, about 50 μg/kg, about 51 μg/kg, about 52 μg/kg, about 53 μg/kg, about 54 μg/kg, about 55 μg/kg, about 56 μg/kg, about 57 μg/kg, about 58 μg/kg, about 59 μg/kg, about 60 μg/kg, about 61 μg/kg, about 62 μg/kg, about 63 μg/kg, about 64 μg/kg, about 65 μg/kg, about 66 μg/kg, about 67 μg/kg, about 68 μg/kg, about 69 μg/kg, about 70 μg/kg, about 71 μg/kg, about 72 μg/kg, about 73 μg/kg, about 74 μg/kg, about 75 μg/kg, about 80 μg/kg, about 85 μg/kg, about 90 μg/kg, about 95 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 500 μg/kg, about 525 μg/kg, or about 550 μg/kg. In some embodiments, the amount of PD-L1-binding molecule administered to the subject in a single dose is about 30 μg/kg. In some embodiments, the amount of PD-L1-binding molecule administered to the subject in a single dose is about 16 μg/kg. In some embodiments, the amount of PD-L1-binding molecule administered to the subject in a single dose is about 8 μg/kg.

In some embodiments, the amount of PD-L1-binding molecule administered to the subject in a single dose is about 0.1 mg to about 10 mg. In some embodiments, the amount of PD-L1-binding molecule administered to the subject in a single dose is about 0.5 mg to about 10 mg. In some embodiments, the amount of PD-L1-binding molecule administered to the subject in a single dose is about 0.1 mg, about 0.2 mg, about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 3.7 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5.0 mg, about 5.1 mg, about 5.2 mg, about 5.3 mg, about 5.4 mg, about 5.5 mg, about 5.6 mg, about 5.7 mg, about 5.8 mg, about 5.9 mg, about 6.0 mg, about 6.5 mg, about 7.0 mg, about 7.5 mg, about 8.0 mg, about 8.5 mg, about 9.0 mg, about 9.5 mg, or about 10 mg.

In some embodiments, the amount of PD-L1-binding molecule administered to the subject in a single cycle (e.g., a 28-day cycle) is about 1 mg to about 100 mg. In some embodiments, the amount of PD-L1-binding molecule administered to the subject in a single cycle (e.g., a 28-day cycle) is about 1 mg to about 5 mg, about 1 mg to about 10 mg, about 1 mg to about 15 mg, about 1 mg to about 20 mg, about 5 mg to about 20 mg, about 5 mg to about 15 mg, or about 5 mg to about 10 mg. In some embodiments, the amount of the PD-L1-binding molecule administered to the subject in a single cycle (e.g., a 28-day cycle) is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg.

In some embodiments, the amount of PD-L1-binding molecule administered to the subject over one or more cycles is about 5 mg to about 1000 mg. In some embodiments, the amount of PD-L1-binding molecule administered to the subject over one or more cycles is about 5 mg to about 250 mg. In some embodiments, the amount of PD-L1-binding molecule administered to the subject over one or more cycles is about 5 mg to about 100 mg. In some embodiments, the amount of PD-L1-binding molecule administered to the subject over one or more cycles is about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1000 mg.

The PD-L1-binding molecule and pharmaceutical compositions thereof may be administered via one or more routes of administration. Routes of administration include, for example, intravenous, intramuscular, intradermal, intraperitoneal, subcutaneous, spinal, or other parenteral routes of administration, such as injection or infusion. In some embodiments, the PD-L1-binding molecule is administered by a non-parenteral route, such as a topical, epidermal or mucosal route of administration, for example, intranasally, orally, vaginally, rectally, sublingually, or topically. In some embodiments, the PD-L1-binding molecule is administered intravenously to a subject in need thereof.

In some embodiments, each dose of the PD-L1-binding molecule is an intravenous infusion that is administered over about 25 to about 75 minutes, such as about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, or about 75 minutes. In some embodiments, each dose of the PD-L1-binding molecule is an intravenous infusion that is administered over about 30 minutes.

In some embodiments, the PD-L1 binding molecule has a Cmax in the range of about 1000 to about 50,000 ng/mL. In some embodiments, the PD-L1 binding molecule has a Cmax in the range of about 1 to about 1,000 ng/mL, about 1,000 to about 3,000 ng/mL, about 2,000 to about 5,000 ng/mL, about 5000 to about 10,000 ng/mL, about 10,000 ng/mL to about 15,000 ng/mL, about 15,000 ng/mL to about 20,000 ng/mL, about 20,000 ng/mL to about 25,000 ng/mL, about 25,000 ng/mL to about 30,000 ng/mL, or about 30,000 ng/mL to about 35,000 ng/mL, or about 35,000 ng/mL to about 50,000 ng/mL. In some embodiments, the Cmax of the PD-L1-binding molecule is about 1,000, about 2,000 ng/mL, about 3,000 ng/mL, about 4,000 ng/mL, about 5,000 ng/mL, about 6,000 ng/mL, about 7,000 ng/mL, about 8,000 ng/mL, about 9,000 ng/mL, or about 10,000 ng/mL. In some embodiments, the Cmax of the PD-L1-binding molecule is about 21,000 ng/mL, about 22,000 ng/mL, about 23,000 ng/mL, about 24,000 ng/mL, about 25,000 ng/mL, about 26,000 ng/mL, about 27,000 ng/mL, about 28,000 ng/mL, about 29,000 ng/mL, or about 30,000 ng/mL. In some embodiments, the Cmax of the PD-L1-binding molecule is 2,096, 27,063, or 22,375 ng/mL.

In some embodiments, the half-life of a PD-L1-binding molecule is about 1 minute to about 1 hour, about 1 hour to about 3 hours, about 3 hours to about 5 hours, or about 5 hours to about 10 hours. In some embodiments, the half-life of a PD-L1-binding molecule is about 5 minutes, about 10 minutes, about 15 minutes, about 20 minutes, about 25 minutes, about 30 minutes, about 35 minutes, about 40 minutes, about 45 minutes, about 50 minutes, about 55 minutes, or about 60 minutes. In some embodiments, the half-life of a PD-L1 binding molecule is about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.6 hours, or about 10 hours. In some embodiments, the half-life of a PD-L1-binding molecule is about 2.8 hours, about 3.7 hours, or about 5.6 hours.

In some embodiments, the PD-L1-binding molecule is administered alone or in combination with one or more other therapeutic or diagnostic agents. In some embodiments, the one or more therapeutic or diagnostic agents are administered on the same day as the PD-L1-binding molecule. In some embodiments, the one or more therapeutic or diagnostic agents are administered at least one day after administration of the PD-L1-binding molecule. Examples of such therapeutic and diagnostic agents include cytotoxic, anti-cancer or chemotherapeutic agents (e.g., radiation or immune checkpoint inhibitors), anti-inflammatory or anti-proliferative agents, antimicrobial or antiviral agents, growth factors, cytokines, analgesics, therapeutically active small molecules or polypeptides, single chain antibodies, classical antibodies or fragments thereof, nucleic acid molecules, and other similar modulating therapeutics which may complement or otherwise be beneficial in a therapeutic treatment regimen.

The methods and compositions described herein can be used to treat a disease, disorder, or condition in a subject. In some embodiments, the PD-L1 binding molecule or pharmaceutical composition thereof is used to treat cancer. In some embodiments, the cancer is bladder cancer (e.g., urothelial carcinoma), breast cancer (e.g., HER2 positive breast cancer, triple negative breast cancer), colon cancer (e.g., colorectal cancer such as metastatic microsatellite instability-high or mismatch repair deficient colorectal cancer), endometrial cancer, esophageal cancer, fallopian tube cancer, gastrointestinal cancer (e.g., gastric cancer, biliary tract neoplasm, gastroesophageal junction cancer), glioblastoma, glioma, head and neck cancer (e.g., squamous cell carcinoma of the head and neck), kidney cancer (e.g., renal cell carcinoma), liver cancer (e.g., hepatocellular carcinoma), lung cancer (e.g., non-small cell lung cancer, small-cell lung cancer), lymphoma (e.g., diffuse large B-cell lymphoma, Hodgkin lymphoma, non-Hodgkin lymphoma, primary mediastinal large B-cell lymphoma), Merkel cell carcinoma, mesothelioma (e.g., pleural mesothelioma), myeloma (e.g., multiple myeloma), nasopharyngeal neoplasm, ovarian cancer, testicular cancer, pancreatic cancer, peritoneal neoplasm, prostate cancer, skin cancer (e.g., squamous cell carcinoma, melanoma, transitional cell carcinoma, or basal cell carcinoma), cervical cancer, uterine cancer, or urothelial cancer. In some embodiments, the PD-L1-binding molecules and pharmaceutical compositions thereof are used to treat solid tumor malignancies. In some embodiments, the PD-L1-binding molecules and pharmaceutical compositions thereof are used to treat non-small cell lung cancer. In some embodiments, the PD-L1-binding molecules and pharmaceutical compositions thereof are used to treat squamous cell cancer of the head and neck.

In some embodiments, the subject has a solid tumor malignancy. In some embodiments, the solid tumor malignancy is unresectable, locally advanced, or metastatic.

In some embodiments, the subject received at least one prior anti-cancer treatment, before administration of the PD-L1-binding molecule. In some embodiments, the subject has cancer and the cancer is relapsed or refractory to treatment with at least one additional anti-cancer therapy, such as immune checkpoint inhibitor therapy. In some embodiments, the subject is relapsed or refractory to treatment with at least one of ipilimumab, nivolumab, pembrolizumab, atexolizumab, durvalumab, avelumab, tremelimumab or cemiplimab. In some embodiments, the cancer is relapsed or refractory to treatment with platinum-based therapy.

In some embodiments, the PD-L1-binding molecule is used to treat an immune disorder. In some embodiments, the PD-L1-binding molecule is used to treat an immune disorder mediated by T cells, B cells, and/or monocytes. In some embodiments, the immune disorder is rheumatic disease, spondylitis, amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjögren's syndrome, ulcerative colitis, or vasculitis.

In some embodiments, the PD-L1-binding molecules can be used to prepare or condition a subject for bone marrow transplantation, stem cell transplantation, tissue transplantation, or organ transplantation.

In some embodiments, a method of treating or slowing the progression of a solid tumor, comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor. PD-L1 expression can be detected using standard immunohistochemistry assays known in the art, for example, the 22C3 PD-L1 IHC assay or SP263 PD-L1 IHC assay. In some embodiments, prior to administration of the PD-L1 binding molecule, the subject is further screened for an HLA:A*02 haplotype. In some embodiments, prior to administration of the PD-L1 binding molecule, the subject is further screened for CMV.

In some embodiments, the subject is heterozygous for the HLA:A*02 haplotype. In some embodiments, the subject is homozygous for the HLA:A*02 haplotype. The term "HLA" is an acronym for "human leukocyte antigen" and refers to the human major histocompatibility complex (MHC). HLA: A*02 is the most prevalent and polymorphic MHC allele family in humans. The alpha chain of HLA:A*02 is encoded by the HLA:A*02 gene and the beta chain of HLA:A*02 is encoded by the B2M locus. An "HLA haplotype" refers to a linked set of genes associated with one haploid genome, which determines the HLA of cells from an individual.

In some embodiments, the subject is screened for HLA status and checked for the HLA:A*2 haplotype prior to administration of the PD-L1-binding molecule. In some embodiments, screening the subject for an HLA:A*02 haplotype comprises analyzing one or more of the following parameters in a subject: (i) HLA:A*02 genotype; (ii) HLA: A*02 expression; (iii) tumor cells expressing HLA:A*02; (iv) tumor cells expressing PD-L1 and HLA:A*02; and/or (v) immune cells expressing PD-L1 and HLA:A*02.

In some embodiments, a method of treating or slowing the progression of a solid tumor comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor; and wherein prior to administration of the PD-L1 binding molecule, the subject is screened for an HLA:A*02 haplotype. HLA can be detected using standard assays known in the art, for example, Mayo HLA class I molecular typing test. In some embodiments, prior to administration of the PD-L1 binding molecule, PD-L1 expression is detected on cells isolated or derived from the solid tumor. In some embodiments, prior to administration of the PD-L1 binding molecule, the subject is further screened for CMV.

In some embodiments, a method of treating or slowing the progression of a solid tumor comprises screening a subject for an HLA:A*02 haplotype and subsequently treating the subject that is positive for the HLA:A*02 haplotype with a PD-L1-binding molecule. A subject that is positive for the HLA:A*02 haplotype refers to a subject that has: (i) a heterozygous or homozygous HLA:A*02 genotype; (ii) cells or tissue that express HLA:A*02 protein or mRNA; (iii) tumor cells that express PD-L1 and HLA:A*02; and/or (iv) immune cells that express PD-L1 and HLA:A*02.

In some embodiments, a method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, the subject is screened for CMV. In some embodiments, the HLA:A*02 haplotype can be detected using standard assays, for example, the Mayo CMVP test (DISI). In some embodiments, the prior to administration of the PD-L1 binding molecule, the subject is further screened for an HLA:A*02 haplotype. In some embodiments, prior to administration of the PD-L1 binding molecule, PD-L1 expression is detected on cells isolated or derived from the solid tumor.

Polynucleotides, Expression Vectors, and Host Cells

Polynucleotides that encode the PD-L1-binding molecules described herein, and components thereof (e.g., the PD-L1-binding region and Shiga toxin effector region), are encompassed within the scope of the present disclosure. Such polynucleotides are specifically disclosed to include all polynucleotides capable of encoding an illustrative protein, for example, taking into account the wobble known to be tolerated in the third position of RNA codons, yet encoding for the same amino acid as a different RNA codon.

In some embodiments, one or more polynucleotides encode the PD-L1-binding molecule or components thereof (e.g., the PD-L1-binding region and Shiga toxin effector region). In some embodiments, the one or more polynucleotides comprise a nucleic acid sequence encoding a polypeptide that is at least 50%, at least 55%, at least 60%, at least 65%, at least 70%, at least 75%, at least 80%, at least 85%, at least 90%, at least 95%, at least 99% or more, identical to a polypeptide of the PD-L1-binding molecule, or component thereof (e.g., the PD-L1-binding region and Shiga toxin effector region). Also described herein are polynucleotides comprising nucleotide sequences that hybridize under stringent conditions to a polynucleotide which encodes all or part of a PD-L1-binding molecule, or components thereof, or the antisense or complement of any such sequence.

In some embodiments, the polynucleotides encode variants of the PD-L1-binding molecule. Variant polynucleotides are produced by altering nucleic acids therein that encode one or more amino acids or deleting or inserting one or more amino acids. Such changes may cause the PD-L1-binding molecule encoded by the nucleic acid to have desired properties, such as more optimal expression by a host cell.

Polynucleotides capable of encoding the PD-L1-binding proteins described herein may be inserted into known vectors, including bacterial plasmids, viral vectors and phage vectors, using material and methods well known in the art to produce expression vectors. Such expression vectors will include the polynucleotides necessary to support production of the PD-L1-binding molecules within any host cell of choice or cell-free expression systems (e.g., pTxb1 and pIVEX2.3). The specific polynucleotides comprising expression vectors for use with specific types of host cells or cell-free expression systems are well known to one of ordinary skill in the art, can be determined using routine experimentation, or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context as described herein, an expression vector encoding a protein comprising a single polypeptide chain (e.g., an anti-PD-L1 scFv genetically recombined with a Shiga toxin effector region) includes at least an expression unit for the single polypeptide chain, whereas a protein comprising, e.g., two or more polypeptide chains (e.g., one chain comprising a $V_L$ domain and a second chain comprising a $V_H$ domain linked to a Shiga toxin effector region) includes at least two expression units, one for each of the two polypeptide chains of the protein. For expression of multi-chain proteins described herein, an expression unit for each polypeptide chain may also be separately contained on different expression vectors (e.g., expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Exemplary host cells include Chinese Hamster Ovary (CHO) cells, HEK 293 cells, BHK cells, murine NSO cells, or murine SP2/0 cells, and *E. coli* cells. Generation and isolation of host cell lines comprising a polynucleotide capable of producing a PD-L1-binding protein may be accomplished using standard techniques known in the art.

In some embodiments, an expression vector comprising a polynucleotide sequence encoding a PD-L1-binding molecule is introduced into a host cell (e.g., *E. coli*) that is capable of expressing the encoded PD-L1-binding molecule. The expressed PD-L1-binding molecule is then purified from the culture system using any one of a variety of methods known in the art (e.g., Protein A columns, affinity chromatography, size-exclusion chromatography, and the like).

Kits

Also provided herein are kits comprising at least one composition as described herein, and optionally, packaging and instructions for use. Kits may be useful for drug administration and/or diagnostic information gathering. A kit may optionally comprise at least one additional reagent (e.g., standards, markers and the like). Kits typically include a label indicating the intended use of the contents of the kit. The kit may further comprise reagents and other tools for detecting a cell type (e.g. a tumor cell) in a sample or in a subject, or for diagnosing whether a patient belongs to a group that responds to a therapeutic strategy which makes use of a compound, composition, or related method, e.g., such as a method described herein.

In some embodiments, a kit is provided that can be used to determine if a subject would be responsive to treatment with one or more of the PD-L1 binding molecules described herein. The kit may include, for example, reagents to detect PD-L1 expression in a sample from the subject, reagents to determine whether the subject has an HLA:A*02 haplotype, and/or reagents to screen the subject for CMV.

In some embodiments, the kit comprises one or more reagents to detect PD-L1 expression in a sample from the subject. In some embodiments, the sample is a solid, semi-solid, or liquid sample, such as stool, blood, urine, saliva, tears, or swab specimens of the cervix, urethra, nostril, or throat. In some embodiments, the sample may comprise cancer cells isolated or derived from the subject. In some embodiments, the sample may be a tumor sample. In some embodiments, the tumor sample may be isolated or derived from the subject's solid tumor. In some embodiments, the kit comprises PCR primers, such as PCR primers capable of amplifying a nucleic acid sequence encoding PD-L1. In some embodiments, the kit comprises one or more antibodies that specifically bind to PD-L1. In some embodiments, the kit comprises a PD-L1 binding molecule, as described herein. In some embodiments, the kit comprises a PD-L1 binding molecule of SEQ ID NO: 1. In some embodiments, the kit comprises a PD-L1 binding molecule having at least 90%, at least 95%, at least 96%, at least 97%, at least 98%, or at least 99% sequence identity to SEQ ID NO: 1. PD-L1 expression can be detected using standard immunohistochemistry assays known in the art, for example, the 22C3 PD-L1 IHC assay or SP263 PD-L1 IHC assay (Ventana).

In some embodiments, detection of PD-L1 expression in a subject sample (e.g., a tumor sample) indicates that the subject will benefit from treatment with a PD-L1 binding molecule, such as the PD-L1 binding molecule of SEQ ID NO: 1.

In some embodiments, the kit comprises one or more reagents to detect an HLA:A*02 haplotype in a sample from the subject. In some embodiments, the sample is a solid, semi-solid, or liquid sample, such as stool, blood, urine, saliva, tears, or swab specimens of the cervix, urethra, nostril, or throat. In some embodiments, the sample may comprise cancer cells isolated or derived from the subject. In some embodiments, the sample may be a tumor sample. In some embodiments, the tumor sample may be isolated or derived from the subject's solid tumor. In some embodiments, the kit comprises one or more PCR primers. The primers may be able to amplify nucleic acid sequences encoding, for example, the HLA-A*02 gene or the B2M locus. In some embodiments, the kit comprises one or more antibodies capable of recognizing the HLA:A*02 haplotype. For example, in some embodiments, the kit comprises one or more antibodies that specifically binds to the alpha-2 domain of the HLA-A alpha-chain. HLA can be detected using standard assays known in the art, for example, Mayo HLA class I molecular typing test.

In some embodiments, detection of and HLA:A*02 haplotype in a subject sample (e.g., a tumor sample) indicates that the subject will benefit from treatment with a PD-L1 binding molecule, such as the PD-L1 binding molecule of SEQ ID NO: 1.

In some embodiments, the kit comprises one or more reagents to detect CMV (cytomegalovirus) in a sample from the subject, such as reagents to detect anti-CMV antibodies. In some embodiments, the sample is a solid, semi-solid, or liquid sample, such as stool, blood, urine, saliva, tears, or swab specimens of the cervix, urethra, nostril, or throat. In some embodiments, the sample may comprise cancer cells isolated or derived from the subject. In some embodiments, the sample may be a tumor sample. In some embodiments, the tumor sample may be isolated or derived from the subject's solid tumor. In some embodiments, the kit comprises PCR primers, such as PCR primers capable of amplifying a nucleic acid sequence of CMV. In some embodiments, the kit comprises one or more antibodies that specifically bind to CMV or a Fragment or derivative thereof. CMV, or antibodies thereto, can be detected using standard assays, for example Mayo CMVP test (DISI).

In some embodiments, detection of PD-L1 expression in a subject sample (e.g., a tumor sample) indicates that the subject will benefit from treatment with a PD-L1 binding molecule, such as the PD-L1 binding molecule of SEQ ID NO: 1.

EXAMPLES

These examples are provided for purposes of illustration only and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the PD-L1-binding molecules of the present disclosure and practice the claimed methods.

Example 1. Manufacturing of a 116297 Pharmaceutical Composition

The PD-L1-binding molecule 116297 is a recombinant fusion protein comprising from N- to C-terminus: an enzymatically active de-immunized Shiga-like toxin-1-A1 Subunit (SLT-1-A1 V1); a murine scFv with affinity for human PD-L1 protein; and an HLA-A*02 immunodominant MHC-I restricted epitope derived from the human cytomegalovirus (HCMV) pp65 protein (amino acids 495-503). 116297 is produced as a single unglycosylated polypeptide chain of 514 amino acids (SEQ ID NO: 1) that forms a non-covalent dimer with the theoretical molecular weight of 112 kD.

The 116297 manufacturing process comprises cell culture (fermentation), harvest, and purification. Briefly, a bacterial host cell line (e.g. *E. coli*) is transformed with one or more expression vectors encoding the PD-L1-binding molecule 116297. 116297-expressing cells are then selected and grown to a high cell density during fermentation. The cells are harvested, and 116297 is recovered from the soluble fraction via cell lysis and clarification. Further purification of 116297 includes affinity chromatography (i.e., using a Protein L resin), filtration, mixed mode chromatography, filtration, and ultrafiltration/diafiltration (UF/DF). 116297 is then formulated as a pharmaceutical composition, and added into bulk drug substance containers. The drug product is then manufactured by dilution and aseptic fill of the formulated drug substance into drug product vials. As such, the drug product and drug substance are the same formulation, with the exception of protein concentration.

The 116297 drug product is a sterile solution containing 0.5 mg/mL 116297 formulated in an aqueous buffer comprised of sodium citrate (20 mM made up of 4.5 mg/mL sodium citrate dihydrate and 1.0 mg/mL citric acid monohydrate), 36.4 mg/mL sorbitol (200 mM), 0.107 mg/mL polysorbate 80 (0.01% v/v), qs to 1.0 mL water at pH 5.5. The 116297 drug product is provided in a glass vial with a rubber stopper and flip-off seal containing 2.2 mL of 116297 drug product to allow for withdrawal of 2.0 mL of the composition comprising 0.5 mg/mL (1.0 mg) 116297.

Characterization of the 116297 Drug Substance:

Several analytical methods were used to characterize 116297 drug substance including assays related to identity, structure, and biological activity.

Mass spectrometric analysis using electrospray ionization (LC/MS) was employed to measure intact 116297. Samples were introduced into the instrument source using a nanospray needle, and external calibration was performed with cesium iodide. Intact mass consistent with Reference Standard was used to confirm the presence of the C-terminal HCMV antigen and confirm full length protein.

Cation exchange chromatography is a form of ion exchange chromatography (IEX), which was used to separate 116297 molecules based on their net surface charge. Cation exchange chromatography, more specifically, uses a negatively charged ion exchange resin with an affinity for molecules having net positive surface charges. The sample was run on an HPLC with a UV detector for peak integration. The 116297 Reference Standard was also evaluated and compared to the test sample. To confirm identity, the retention time of the main peak must be comparable to the Reference Standard.

The quantity of 116297 was determined by absorbance at 280 nm. The drug substance concentration was calculated from A280 values utilizing the predicted molecular weight (111,628 Da) and calculated extinction coefficient (160,020 $M^{-1}$ $cm^{-1}$) for the protein homodimer. Each sample was read in triplicate, and the average absorbance was used to calculate the protein concentration. The chemical purity of 116297 was assessed by capillary gel electrophoresis performed under reducing conditions. This electrophoretic assay was based on traditional gel electrophoresis principles that have been transferred to a chip format. During chip preparation, the micro-channels were filled with a sieving polymer and fluorescence dye. Charged protein molecules were electrophoretically driven by a voltage gradient. Because of a constant mass-to-charge ratio and the presence of a sieving polymer matrix, the molecules were separated by size. Purity was determined by peak integration of the primary protein peak in comparison to other detected peaks.

Size-exclusion high performance liquid chromatograph (SE-HPLC) with peak integration was utilized to describe the dimeric, aggregate peaks, and low molecular weight (LMW) forms of 116297. Column eluate was monitored by absorbance at 280 nm. The sample's dimer purity was calculated as the sample's main peak area divided by the total peak area multiplied by 100. This peak was the primary peak of interest, which corresponds to the drug substance. The LMW reported result corresponds to the combined percent areas of peaks eluting later than the main peak, and the aggregate reported result corresponds to the combined percent areas of peaks eluting prior to the main peak.

A summary of the characterization results is provided in Table A below.

TABLE A

Summary of Characterization of the 116297 Structure

| Test | Test Batch 116297 |
|---|---|
| N-terminal Sequencing | Conforms to Theoretical |
| Molecular Weight Determination by MS | Conforms to Theoretical |
| Peptide Mapping, LC-MS | 100% sequence coverage |
| Potency Assay | IC50: 0.6072 ng/mL |
| SE-HPLC | Main Peak: 98.2%<br>LMW: 0.5%<br>Aggregate: 1.3% |

The results of the Edman degradation study confirmed that the N-terminal sequence of the 116297 engineering batch conformed to the predicted N-terminal sequence of 116297 (SEQ ID NO: 1) based on expression of the construct sequence.

Figure 1B:
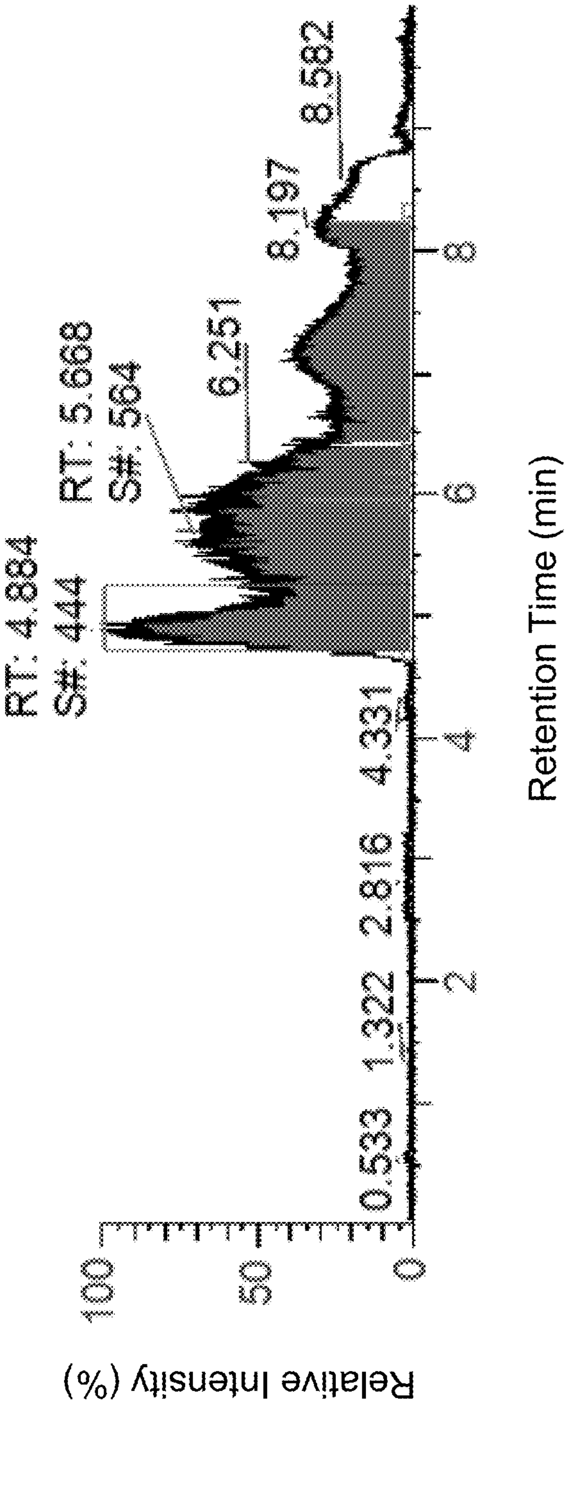
FIG. 1B shows a total ion chromatogram (TIC) for the 116297 drug substance from liquid chromatography-mass spectrometry (LC-MS) analysis.
Figure 1C:
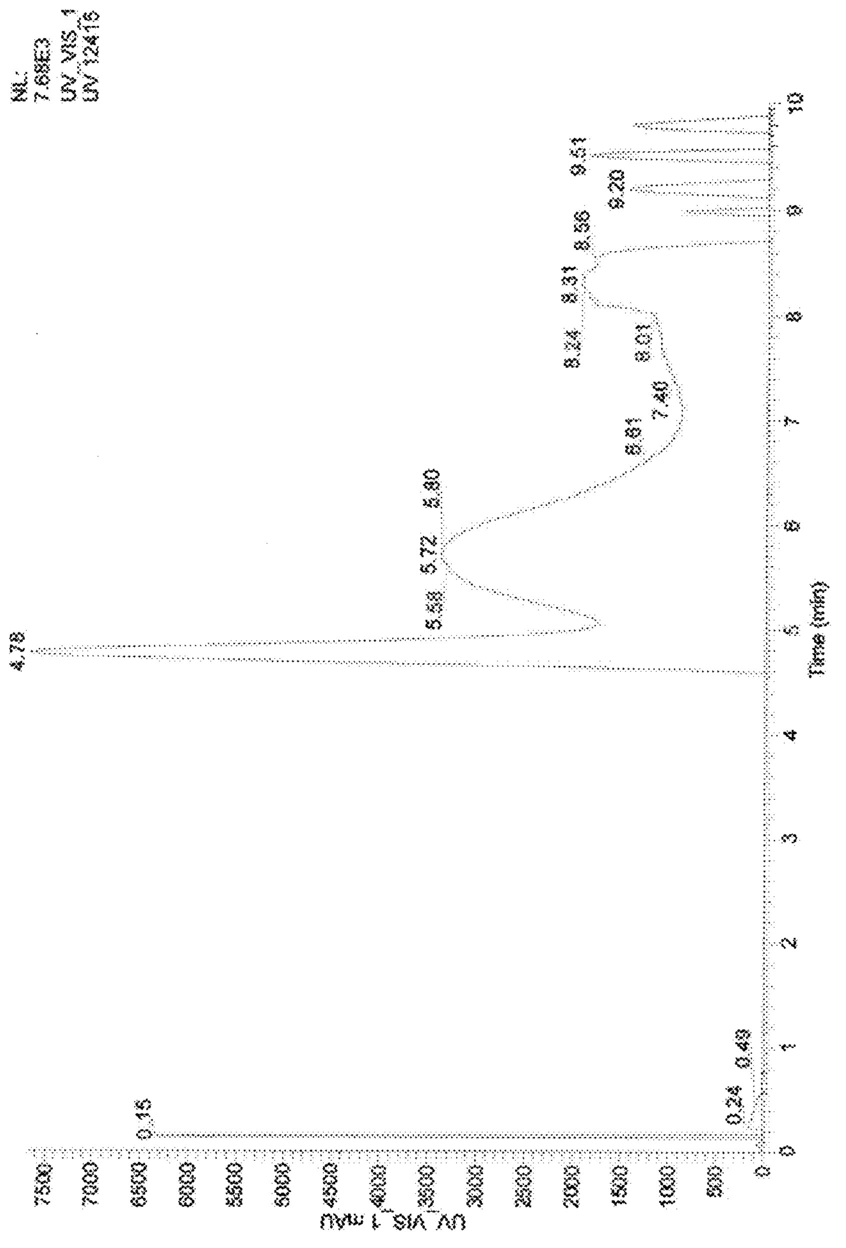
FIG. 1C shows an ultraviolet (UV) chromatogram 116297 for the drug substance from LC-MS analysis.
Figure 1D:
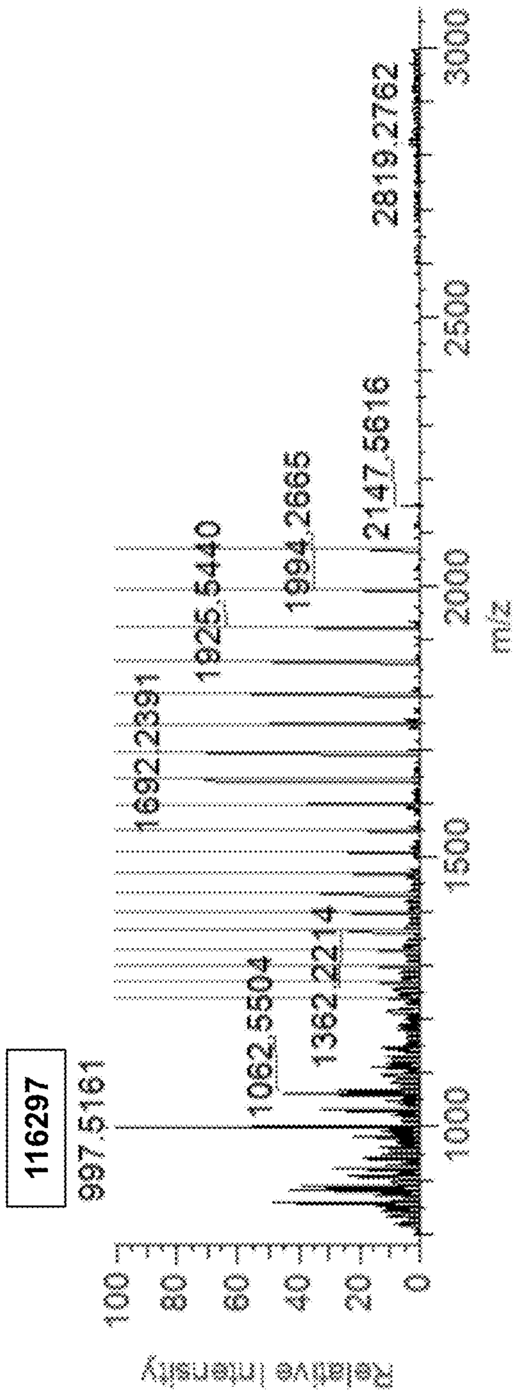
FIG. 1D shows the MS spectrum obtained from the peak eluting at about 4.8 min for 116297 drug substance in the UV chromatogram of FIG. 3C.
Figure 1E:
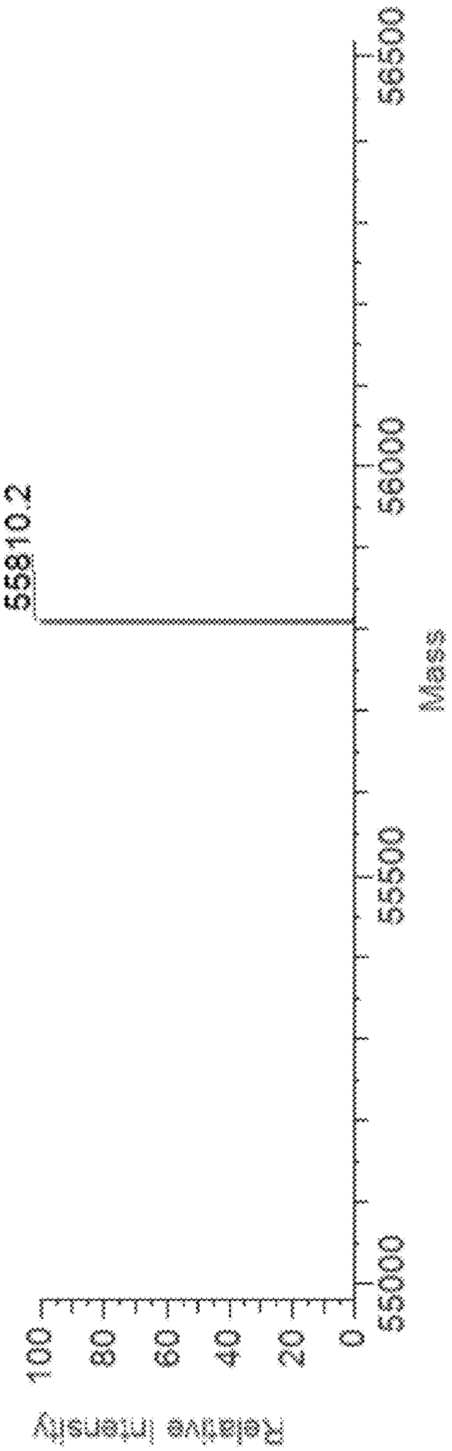
FIG. 1E shows the MS deconvolution spectra obtained from peak eluting at about 4.8 min for the 116297 drug substance in the UV chromatograph of FIG. 3C.

The theoretical mass of 116297 was calculated using the amino acid sequence (SEQ ID NO: 1), which has a calculated average mass of 55814 Da for the monomer without two intra-chain disulfide bonds. FIG. 1A shows a capillary gel electrophoresis (CGE) electropherogram for the 116297 drug substance under reducing denaturing conditions. FIG. 1B and FIG. 1C show the TIC and UV chromatograms from the LC-MS analysis, respectively, and FIG. 1D shows the MS spectrum from the peak eluting at 4.8 min. The deconvoluted mass spectrum from the protein peak is shown in FIG. 1E. Deconvolution of the multiply-charged protein ions within the m/z range of 800-2200 resulted in the presence of a major component having a molecular mass of 55810 Da, which matches the calculated molecular mass with 2 intact intra-chain disulfide bonds (55814 Da−4 Da=55810 Da).

Peptide mapping was performed by online LC-MS analyses of peptide mixtures resulting from the successive digestions of the protein sample by Trypsin and Glu-C, as well as Trypsin and Chymotrypsin. The Trypsin/Glu-C digestion followed by LC-MS analysis resulted in 100% sequence coverage. Two disulfide bridges, natively occurring in the scFv subunit, were confirmed with two different protease digestion strategies. Trypsin/Glu-C digestion was used to confirm the C290-C364 bridge and Trypsin/Chymotrypsin digestion was used to confirm the C418-C482 bridge.

Figure 1F:
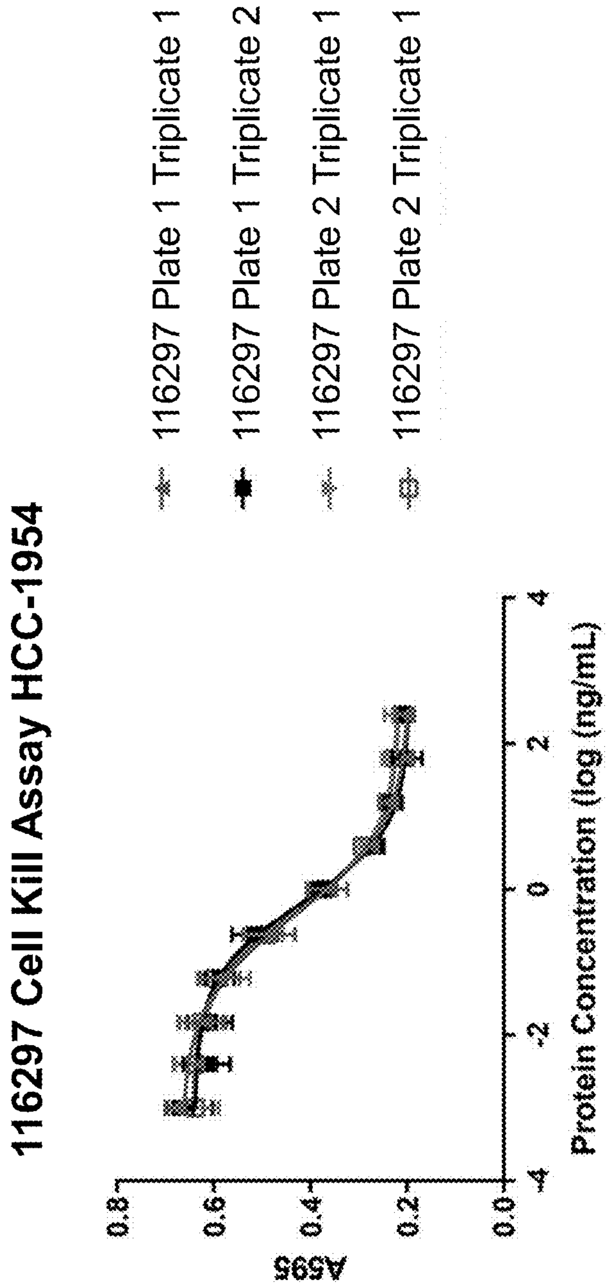
FIG. 1F shows the cytotoxicity of 116297 on HCC1954 cells.

The potency of the 116297 drug substance was measured using a cytotoxic (cell kill) assay. Cell kill was evaluated by incubating the PD-L1-expressing breast ductal cancer line, HCC-1954, with selected concentrations of 116297 and evaluating cell viability after 3 days of incubation by addition of Cell Titer Blue (Promega). The $IC_{50}$ was calculated from the dilution curve and the results were compared to a potency standard. The 116297 drug substance showed an average $IC_{50}$ value of 0.6072 ng/mL (FIG. 1F).

Figure 1G:
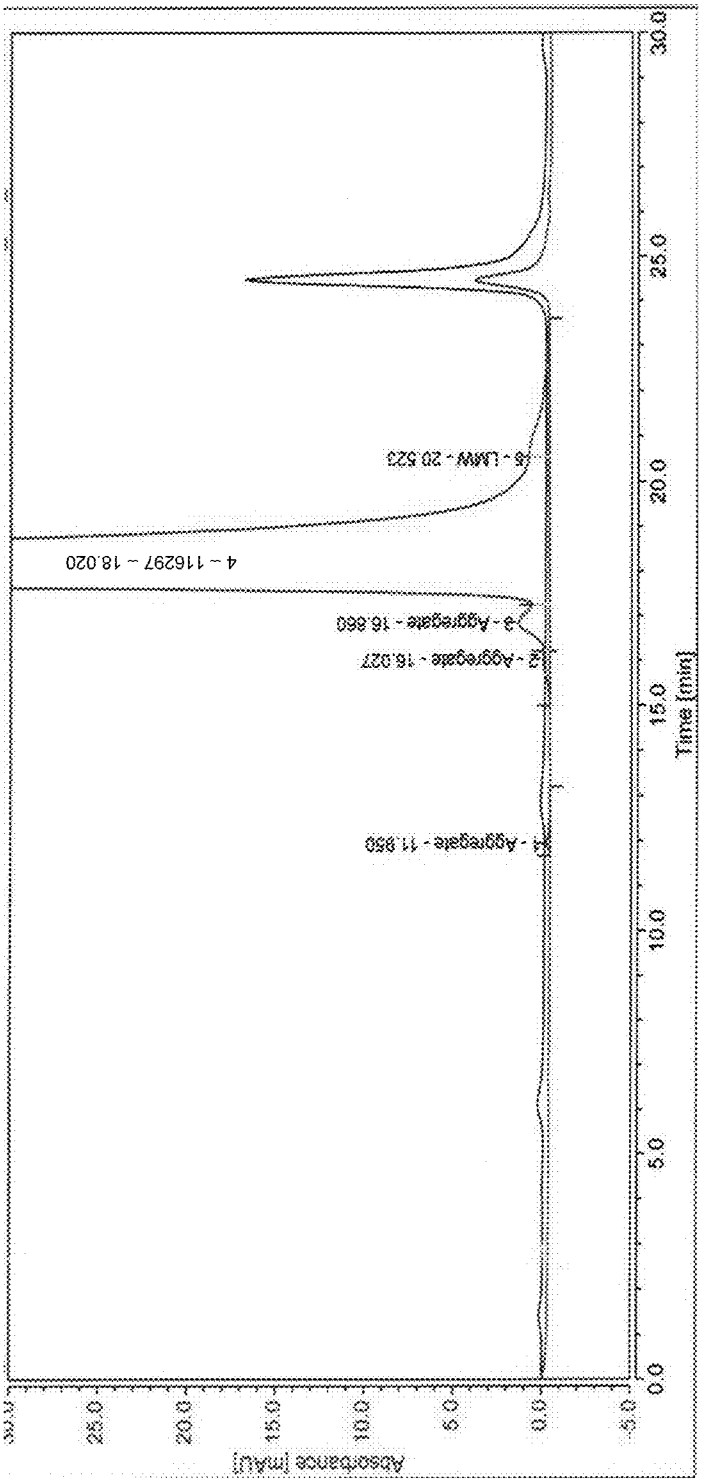
FIG. 1G shows a size-exclusion high-performance liquid chromatography (SE-HPLC) chromatogram of a pharmaceutical composition comprising 116297 (red line). The black line is the formulation buffer.

SE-HPLC was used to analyze the 116297 protein mixture under non-denaturing conditions. The monomeric, dimeric, and oligomeric species of 116297 were chromatographically resolved by SE-HPLC (FIG. 1G). The chromatogram demonstrates that under native conditions 116297 is predominantly in a homodimeric form with a peak retention time of approximately 17.4 minutes. The rise in signal at approximately 24 minutes represents a buffer peak that is expected as part of the method. The small peak at approximately 15.5 minutes is consistent with aggregated 116297, and the peak at approximately 20.5 minutes is a low molecular weight species.

Figure 1H:
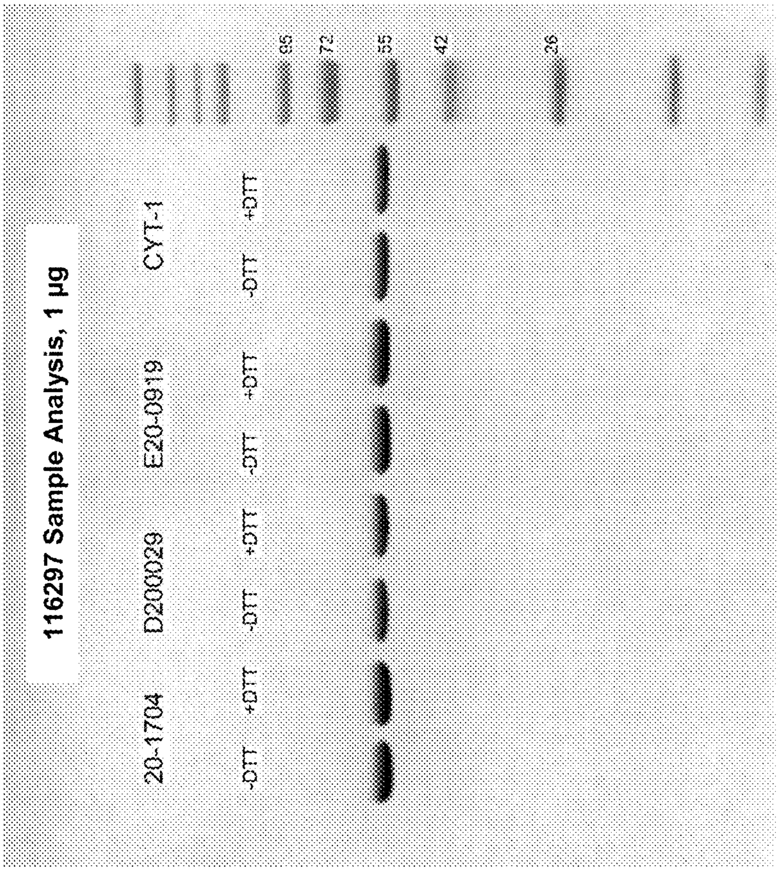
FIG. 1H shows a stained sodium dodecyl sulfate polyacrylamide gel electrophoresis (SDS-PAGE) gel of the 116297 drug substance under denaturing, non-reducing conditions.

SDS-PAGE was used to analyze the 116297 drug substance under denaturing, non-reducing conditions. A single band was observed in an SDS-PAGE gel (FIG. 1H). The gel demonstrates that under denaturing and non-reducing conditions, 116297 is predominantly a single species at an approximate MW of 56 kDa, which corresponds to a monomer of the molecule. In summary, the SDS-PAGE and SE-HPLC data demonstrate that under non-denaturing conditions the predominant species is a homodimer and the protein in solution is primarily homodimeric and linked via noncovalent interactions.

Characterization of Impurities in the 116297 Drug Substance:

The manufacturing of 116297 results in process- and product-related impurities in the final drug product. Endotoxin testing of 116297 was performed using the Limulus Amebocyte Lysate test. Bioburden testing of 116297 was performed using the number of viable aerobic bacteria present using a membrane filtration method. Host cell protein in the 116297 drug substance was measured using an ELISA kit for the detection of *E. coli* host cell protein impurities. Host cell DNA was measured using qPCR to detect *E. coli* DNA. Table B summarizes the residual levels of impurities in the manufacturing batches of the 116297 drug substance.

TABLE B

Process-Related and Product-Related Impurities for the 116297 Drug Substance

| Test | Test Batch 1 116297 | Test Batch 2 116297 |
|---|---|---|
| Residual Kanamycin | <50 ng/mL | <50 ng/mL |
| Residual Triton X-100 | <250 ng/mL | <250 ng/mL |
| Residual Protein L | <1 ng/mL | <1 ng/mL |
| Glucan | <1 ng/mL | <1 ng/mL |
| Host Cell DNA | <0.1 ng/mL | <0.1 ng/mL |
| Host Cell Protein | <1 ng/mL | <1 ng/mL |
| Bioburden | <1 CFU/mL | <1 CFU/mL |
| | <1 CFU/mL | <1 CFU/mL |
| Endotoxin | <2 EU/mL | <2 EU/mL |
| CGE[1] | 96.9% | 91.5% |
| | 98.2% | 98.4% |
| SE-HPLC[1] | 1.3% | 1.2% |
| | 0.5% | 0.5% |
| Visual Appearance | Clear, colorless solution contains white particles | Clear, colorless solution, contains white particles |

[1]Product purity is determined by CGE and SE-HPLC. SE-HPLC measures abundance of size-related variants under native conditions and CGE measures primary chemical purity under denaturing-reducing conditions. Product related impurities are monitored by these methods.

Figure 2B:
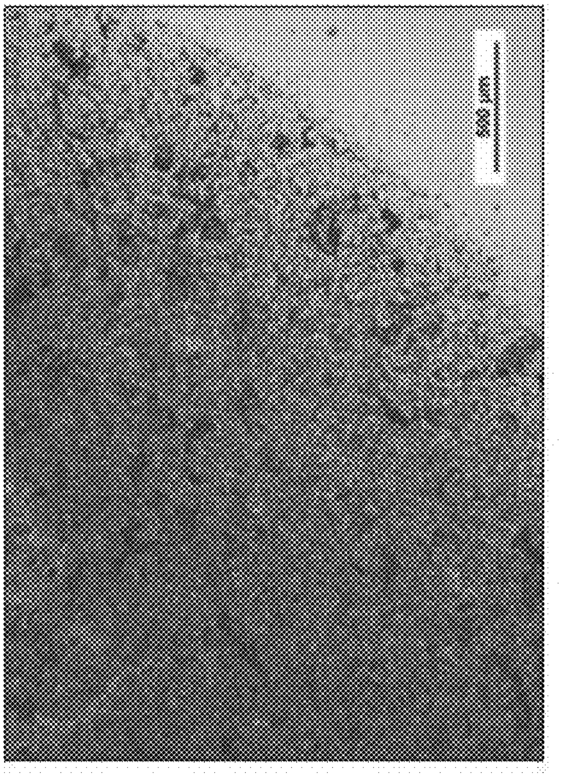
FIG. 2B shows a representative image of the filtered vial contents of the drug product particles.
Figure 2A:
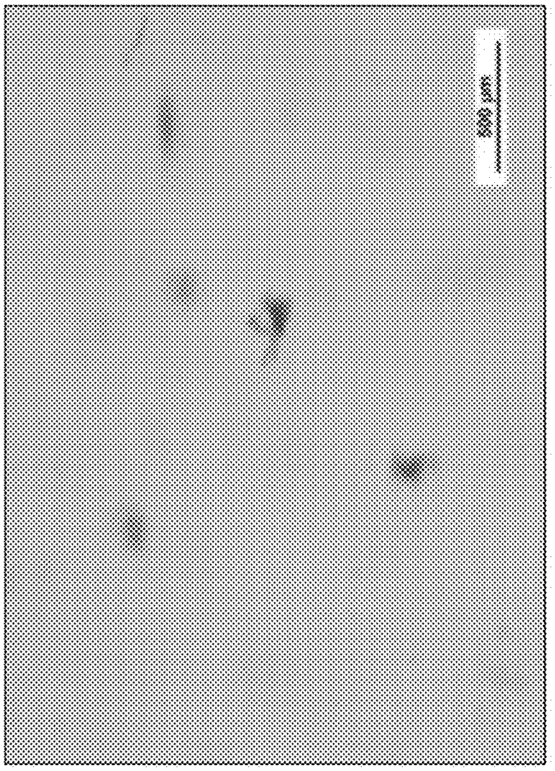
FIG. 2A shows a representative image of the particles in an unopened drug product vial.

The 116297 drug substance and drug product have been observed to contain visible particulates. The visible particulates have been characterized as translucent to white, amorphous or fibrous particles, consistent with proteinaceous aggregates. A representative image of the particles in an unopened drug product vial is shown in FIG. 2A and a representative image of the filtered vial contents of the drug product particles is shown in FIG. 2B.

Figure 2C:
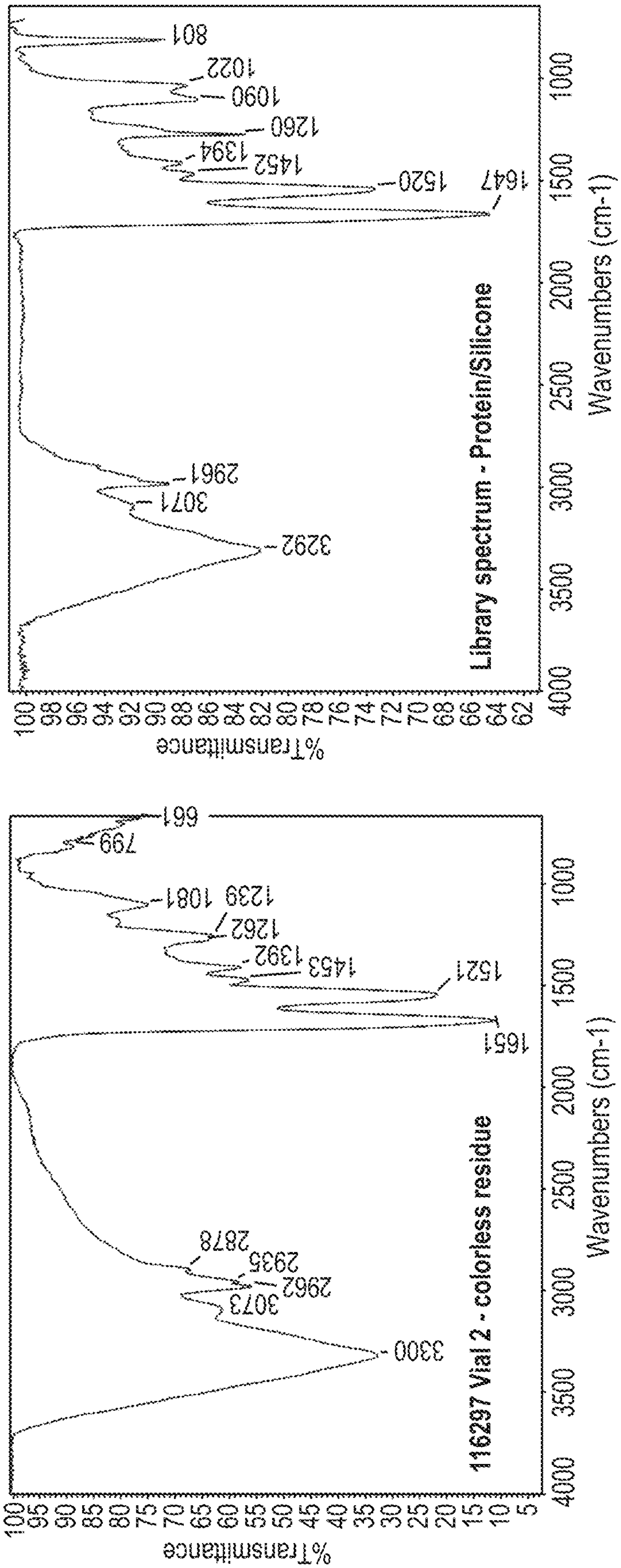
FIG. 2C shows a representative image of 116297 drug product particle infrared spectrum (left panel) and a library image of protein/silicone infrared spectrum (right panel).

The visible particulates were further characterized by infrared spectroscopy. The IR spectra of the particles were determined to be consistent with spectra for proteinaceous particles by comparison to spectra of known protein compounds using library-searching software along with spectral interpretation by the analyst (FIG. 2C). The particles from each vial were identified as protein and ranged in size from approximately 25-1250 μm. Some of the spectra had weak bands near 1260 $cm^{-1}$, generally as a shoulder on the band near 1238 $cm^{-1}$, and near 800 $cm^{-1}$ that are indicative of traces of residual silicone, which can be linked to the drug product manufacturing process.

An inline infusion study was conducted for 116297 drug product diluted in normal saline (9%) to 250 mL volume in IV bags at concentrations in the range 10 μg/mL to 100 μg/mL. The study was performed using a 0.2 μm polyethersulfone (PES) membrane inline filter. Post-filtration samples were collected during pump infusion at a rate of 100 mL/hour. The removal of particulates by inline filtration was assessed by quantification of sub-visible particles in the post-filtration samples using the HIAC Liquid Particle Counting System and comparing the results with HIAC measurements conducted on pre-filtration samples and saline. The results show removal of particles sized ≥10 μm and ≥25 μm that were present in the 116297 solution at all dosage concentrations evaluated up to 100 μg/mL, as shown in Table C below.

TABLE C

| Particle Counts for Pre- and Post-Filtration of the 116297 Solution | | | |
|---|---|---|---|
| | 116297 Dosage | Particles per 250 mL | |
| Timepoint | (μg/mL) | >10 μm | >25 μm |
| Pre-filter | 0 | 633 | 33 |
| | 10 | 5583 | 350 |
| | 30 | 23183 | 933 |
| | 100 | 66850 | 2267 |
| Post-filter | 0 | 133 | 17 |
| | 10 | 50 | 17 |
| | 30 | 233 | 0 |
| | 100 | 2567 | 33 |

Stability of the 116297 Drug Product:

A long-term and accelerated study to evaluate the stability of the 116297 drug substance at −80±10° C. and at −20±5° C. is currently ongoing. The recommended storage condition for the 116297 drug product is −20° C.±5° C.

Clinical Use of the 116297 Drug Product:

116297 is shipped frozen to clinical sites and stored frozen until thawed for use. Partially or fully thawed vials must not be refrozen. Prior to use, thawed 116297 vials with intact stoppers may be kept at room temperature (15-30° C.) for up to 4 hours, or refrigerated at 2-8° C. for up to 7 days. The thawed vial should not be inverted, or vortexed.

For each subject, the administered dose is calculated based on body weight, and the number of vials needed for a single day of dosing for a given subject are removed from the freezer.

Following removal from the freezer, the 116297 vials are thawed at room temperature (20-25° C.). 116297 is mixed by gently swirling the fully thawed vial. The 116297 drug product can be diluted according to the sample calculation show in Table D below, assuming a 100 mL bag infusion.

TABLE D

| Illustrative dilutions of the 116297 drug product | | | | | |
|---|---|---|---|---|---|
| Dose/day (μg/kg) | Body weight (kg) | Day's dose (μg) | 116297 (0.5 mg/mL) volume (mL) | Volume of NS removed from a 100 mL Bag (mL) | Number of vials (2mL/vial) |
| 10 | 70 | 700 | 1.4 | 1.4 | 1 |
| 20 | 70 | 1400 | 2.8 | 2.8 | 2 |
| 50 | 70 | 3500 | 7.0 | 7.0 | 4 |
| 100 | 70 | 7000 | 14.0 | 14.0 | 8 |

Once the 116297 vial is completely thawed and mixed, the calculated amount of 116297 should be withdrawn from the vials and diluted in an infusion bag containing 0.9% sodium chloride to the desired final concentration for infusion using sterile technique. The infusion bag contents must be administered with an infusion line containing an in-line filter and catheter.

Example 2. In Vivo Efficacy of 116297 in an NSCLC PDX Model

The ability of 116297 to limit the growth of PD-L1 positive tumors was evaluated using a PD-L1 positive patient-derived xenograft (PDX) model of human non-small cell lung cancer (NSCLC) in immunocompromised mice.

Patient-derived PD-L1 positive NSCLC tumor cells were implanted into immunodeficient mice. After tumors were established, tumor-bearing mice were administered 116297 intravenously at 6 mg/kg on Days 0 and 14, and at a maintenance dosing schedule of 2 mg/kg on Days 2, 4, 7, 9, 11, 16, 18, 21, 23 and 25. Tumor growth was monitored twice a week and the tumor volume (TV) was recorded.

Figure 3A:
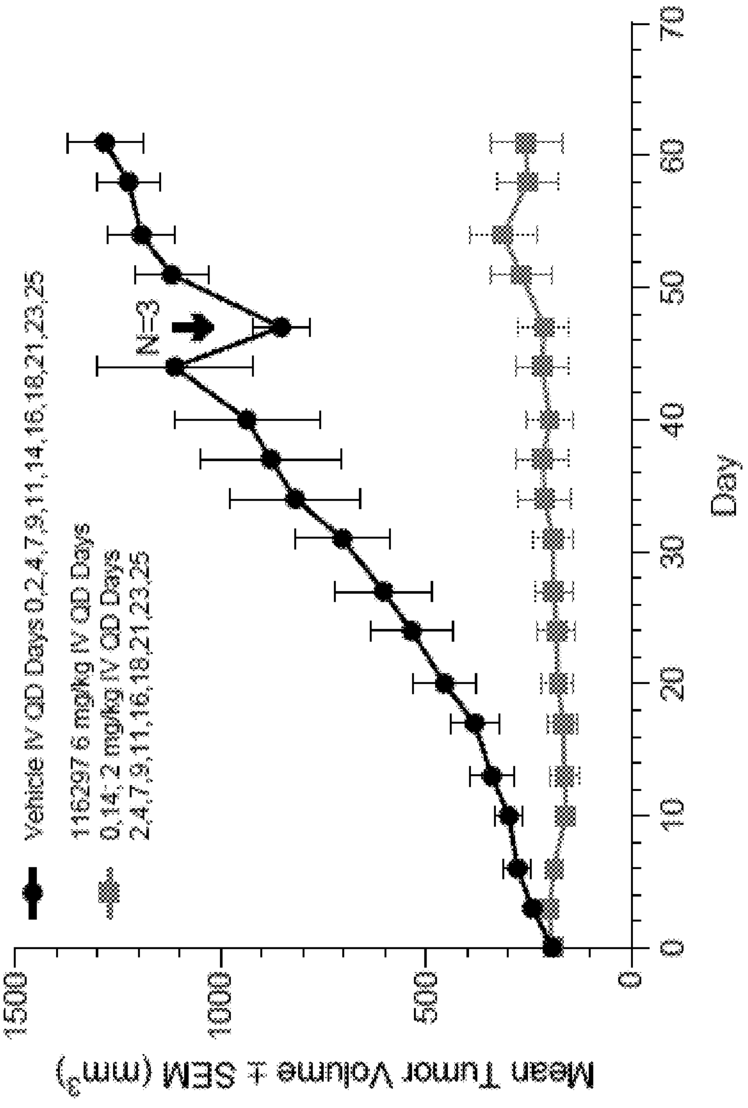
FIG. 3A shows mean tumor volume over time in a PDX model of human NSCLC, after treatment with 116297 as indicated.
Figure 3B:
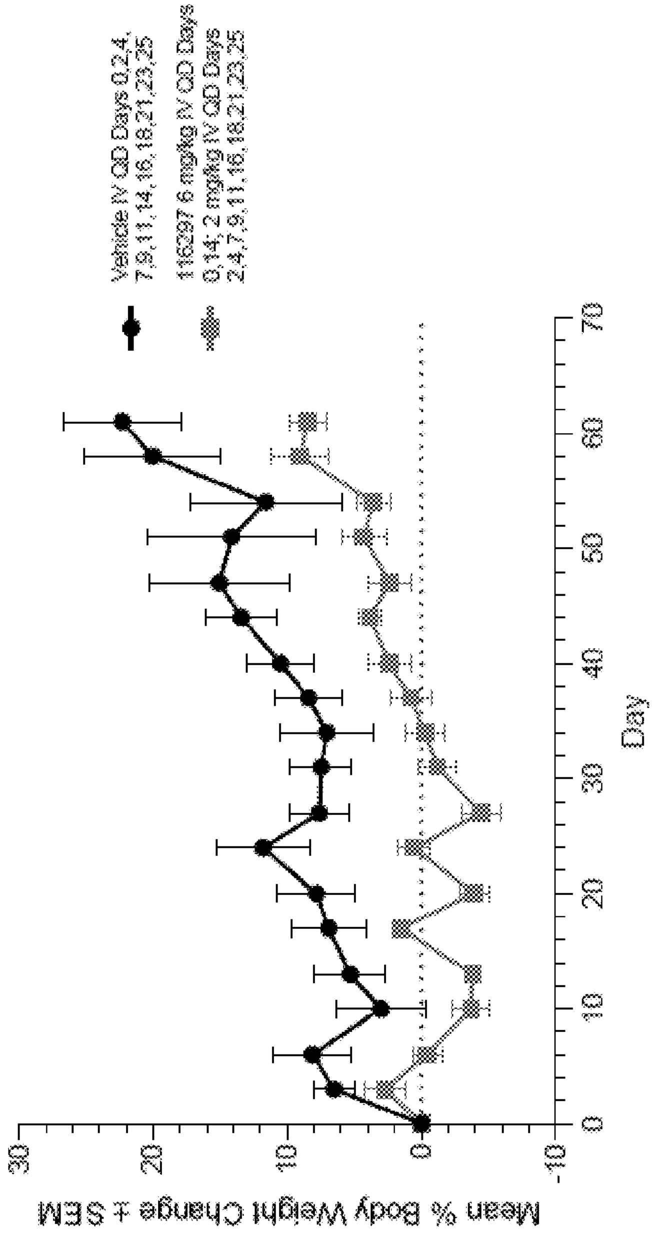
FIG. 3B shows mean body weight over time in a PDX model of human NSCLC, after treatment with 116297 as indicated. Tumor-bearing mice received intravenous treatment with 116297 at 6 mg/kg on Days 0 and 14 and at a maintenance dosing schedule of 2 mg/kg on Days 2, 4, 7, 9, 11, 16, 18, 21, 23, and 25. The vehicle control group received treatment on Days 0, 2, 4, 7, 9, 11, 14, 16, 18, 21, 23, and 25. QD refers to once daily dosing.

116297 significantly inhibited tumor growth compared to the vehicle control (FIG. 3A). Mice treated with the vehicle control had no mean body weight loss, and the 116297-treated group had only minor mean body weight losses within Days 0-34, and subsequently gained mean body weight thereafter (FIG. 3B). There was no death or moribund animal in any group, and 116297 was well-tolerated.

These data demonstrate the ability of 116297 to elicit tumor control after systemic delivery in a murine model of humanized tumorigenesis and support the potential for 116297 to provide benefit to humans with PD-L1 positive solid tumors.

Example 3. In Vivo Safety of 116297 in Non-Human Primates

The in vivo safety of the PD-L1-binding molecule 116297 was evaluated in non-human primates (NHP). A summary of the toxicology studies performed in NHP is described below.

4-Week Toxicity and Toxicokinetic Study by Intravenous Injection of 116297 in Cynomolgus Monkeys (Study 1):

116297 was administered weekly by IV bolus injection followed by a 0.5 to 1 mL saline flush via the tail vein, or another suitable vein, on Days 1, 8, 15, and 22. The experimental design included four groups: Control (treated with vehicle: 20 mM Citric acid, 2000 mM Sorbitol, pH 5.5) as well as Groups 2, 3, and 4 for the 116297 testing doses of 50, 150 and 450 μg/kg/dose, respectively (n=2/group). The first day of dosing was designated as Day 1. The study design is shown in Table E below.

TABLE E

| Study Design for the 4-Week Toxicity and Toxicokinetic Study | | | | | |
|---|---|---|---|---|---|
| Group Number | Test Material | Dose Level (μg/kg) | Dose Volume[a] (mL/kg) | Dose Concentration (μg/mL) | Dosing Days |
| 1 | Control[b] | 0 | 1 | 0 | 1, 8, 15, 22 |
| 2 | 116297 | 50 | 1 | 50 | 1, 8, 15, 22 |
| 3 | 116297 | 150 | 1 | 150 | 1, 8, 15, 22 |
| 4 | 116297 | 450 | 1 | 450 | 1, 8, 15, 22 |

[a]Based on the most recent body weight measurement
[b]Buffer C (20 mM Citric acid, 200 mM Soibitol, pH 5.5) diluted in 0.9% Sodium Chloride 116297-related clinical observation included flaking/dry skin at doses ≥150 μg/kg. No treatment-related effects were observed on food consumption and bodyweights. There were also minimal changes observed in hematology, coagulation, clinical chemistry, biomarkers and cytokine production.

Figure 4:
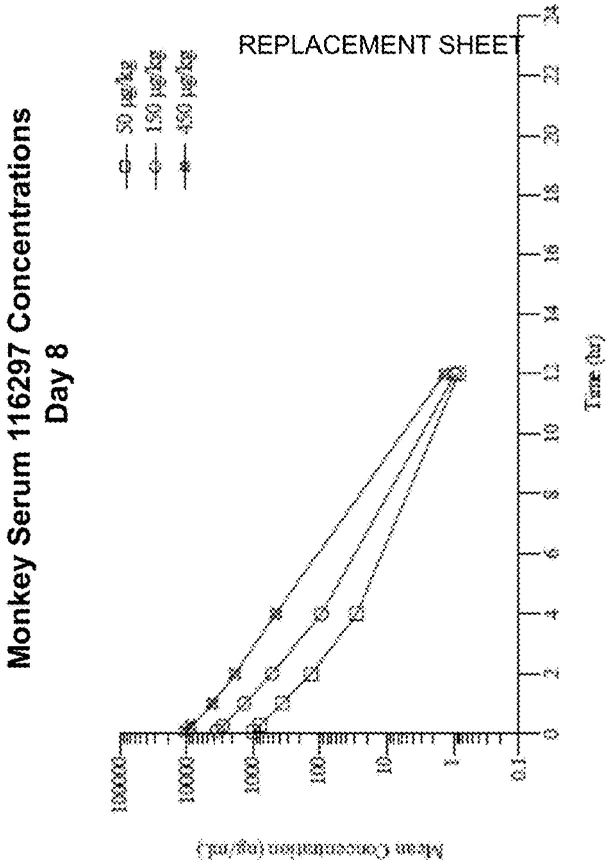
FIG. 4 shows mean serum 116297 concentrations in female cynomolgus monkeys over time following intravenous bolus injection of 116297 on Day 1 (left panel) and Day 8 (right panel).
Figure 4:
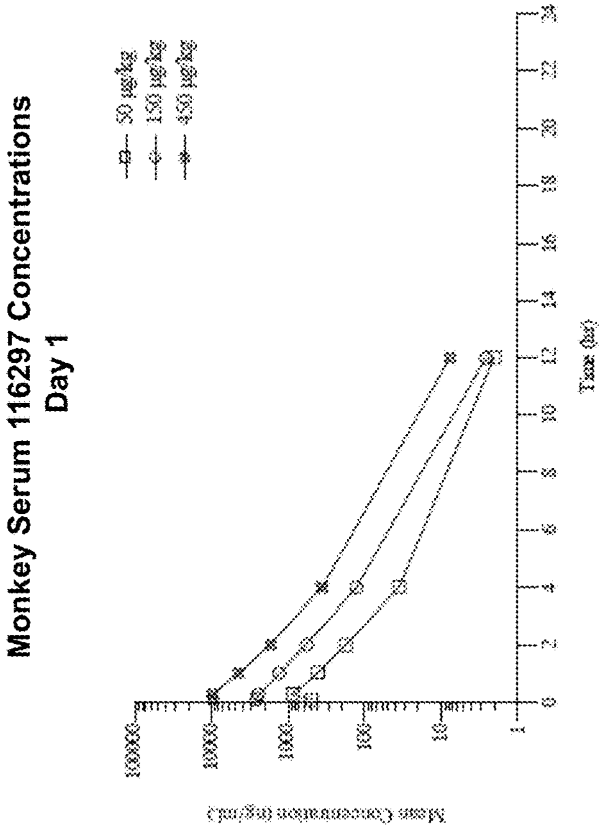

The serum concentration of 116297 increased proportionally with dose levels between 50 and 450 μg/kg on both Days 1 and 8 (FIG. 4). The individual apparent half-life values of 116297 were estimated from 1.27 to 1.72 hours on Day 1 and from 0.734 to 1.68 hours on Day 8.

All animals developed anti-drug antibodies (ADA) while receiving 116297 on Days 8, 15, 22, and 23, whereas all controls were found negative at all time points. Serum concentrations of 116297 remained similar between Days 1 and 8 despite the presence of ADA in serum samples collected on Day 8 at all dose levels (FIG. 4). The impact of antibodies against 116297 was noted on Days 15, 22, and 23 where there was no quantifiable 116297 in serum samples at all dose levels.

In summary, intravenous administration of 116297 once per week for 4 weeks was tolerated in monkeys up to 450 μg/kg. Therefore, the maximum tolerated dose for 116297 administered intravenously once per week for 4 weeks to cynomolgus monkeys was 450 μg/kg.

4-Week Toxicity and Pharmacodynamics Study by Intravenous Injection of 116297 in Cynomolgus Monkeys (Study 2):

A toxicity and pharmacodynamics study of 116297 was performed in female cynomolgus monkeys.

Female monkeys were administered a bolus intravenous injection of 116297 once a week for up to 4 weeks with doses 0, 50 and 450 μg/kg (group 1, group 2 and group 3, respectively) on Days 1, 8, 15 and 22. Two additional groups (group 4 and 5) were administered with 116297 at a different dosing schedule to understand differences in the pharmacodynamics- and exposure-related effects of 116297. The study design is shown in Table F below.

TABLE F

Study Design for the 4-Week Toxicity and Pharmacodynamics Study

| Group No. | Test Material | Dose Level (μg/kg) | Dose Volume (mL/kg)[a] | Dose Concentration (μg/mL) | Dosing Days |
|---|---|---|---|---|---|
| 1 | Control[b] | 0 | 1 | 0 | 1, 8, 15, 22 |
| 2 | 116297 | 50 | 1 | 50 | 1, 8, 15, 22 |
| 3 | 116297 | 450 | 1 | 450 | 1, 8, 15, 22 |
| 4 | 116297 | 450 | 1 | 450 | 1 |
| 5 | 116297 | 450 | 1 | 450 | 1, 15 |

[a]Based on the most recent body weight measurement

[b]Buffer C (20 mM Citric acid, 200 mM Sorbitol, pH 5.5) diluted in 0.9% Sodium Chloride All animals survived to scheduled necropsy. Clinical signs attributed to 116297 included decreased activity/loss of consciousness, dilated pupils, and vomitus, and were likely immunologic reactions secondary to the 116297 administration. Clinical signs of uncertain relationship to 116297 included reduced appetite and/or decreased fecal output.

There were minimal changes observed in hematology, coagulation, clinical chemistry, biomarkers and cytokine production.

116297-related mononuclear cell infiltration was observed in the heart (H&E and IHC) and draining (axillary) lymph nodes at all time points. Degeneration/necrosis was also observed in 116297-treated groups. The incidence and severity of immunohistochemical evaluation correlated with microscopic findings of degeneration/necrosis and mononuclear infiltration within the heart across treatment groups. There were no changes in electrocardiography, respiration rate, blood pressure, or heart rate associated with the cardiac findings.

Figure 5:
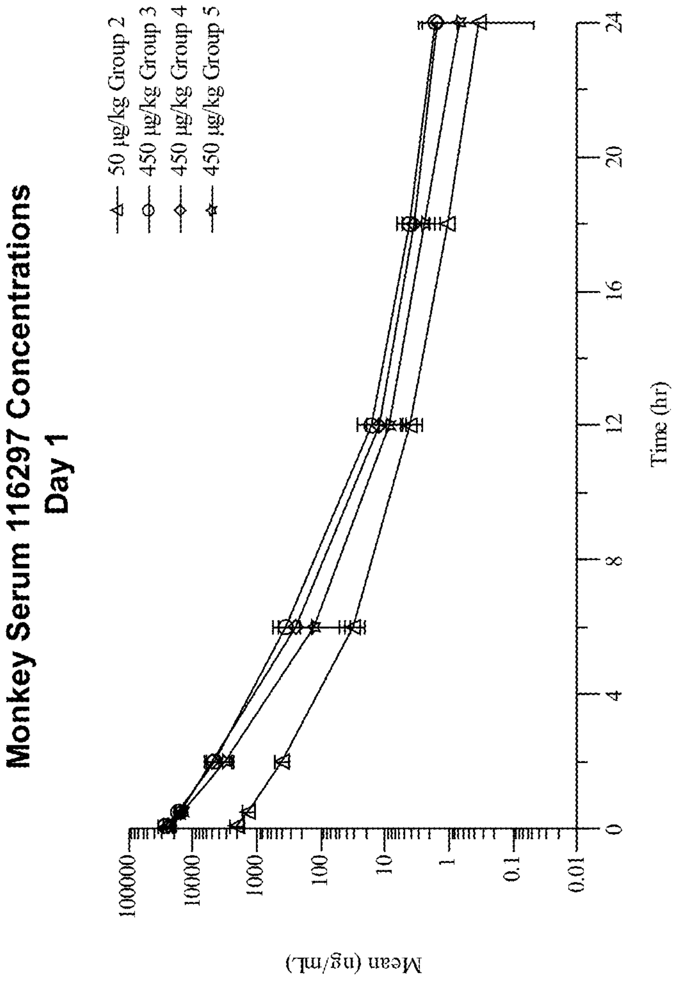
FIG. 5 shows mean serum 116297 concentrations over time in female cynomolgus monkeys following intravenous bolus injection of 116297 on Day 1.

Serum concentrations of 116297 were similar between Days 1 and Day 8 despite the presence of ADA in serum samples collected on Day 8 from Group 2 (50 μg/kg) and 3 (450 μg/kg) animals (FIG. 5). The individual apparent half-life values were estimated from 1.19 to 6.23 hours on Day 1 for all groups and from 0.197 to 0.928 hours on Day 15 for Group 5 (450 μg/kg). Serum concentrations of 116297 increased with increasing dose in an approximately dose-proportional manner between 50 and 450 μg/kg on Day 1 (FIG. 5). The impact of antibodies against 116297 was noted on Days 15 and 22 where there was a decrease in serum concentrations or no quantifiable concentrations of 116297 in all groups were observed.

In summary, administration of 4 doses of 50 μg/kg of 116297 or 1, 2, or 4 doses of 450 μg/kg of 116297 by intravenous injection was tolerated. Based on the cardiac findings that occurred in the 450 μg/kg dose group with 116297, the no-observed-adverse-effect level of 116297 was considered to be 50 μg/kg. 4-Week Study by Intravenous Injection of 116297 in Cynomolgus Monkeys (Study 3):

The toxicokinetics of 116297 was evaluated in male and female cynomolgus monkey serum following weekly IV bolus administration of 116297 at dose levels of 0, 20, 60, or 300 μg/kg on Days 1, 8, 15, and 22. The study design is presented in Table G below.

TABLE G

4-Week Study of 116297 in Monkeys

| Group No. | Test Material | Dose Level (μg/kg) | Dose Volume (mL/kg)[a] | Dose Concentration (μg/mL) |
|---|---|---|---|---|
| 1 | Control[b] | 0 | 0.5 | 0 |
| 2 | 116297 | 20 | 0.1 | 200 |
| 3 | 116297 | 60 | 0.1 | 600 |
| 4 | 116297 | 300 | 0.5 | 600 |

[a] Based on the most recent body weight measurement

[b] Buffer C (20 mM Citric acid, 200 mM Sorbitol, pH 5.5) diluted in 0.9% Sodium Chloride All animals survived to scheduled necropsy. There were no 116297-related clinical signs or effects on body weight and body weight gain, qualitative food consumption, ophthalmology, safety pharmacology parameters (electrocardiology [qualitative and quantitative evaluation], body temperature, blood pressure, and heart rate).

There were minimal changes observed in hematology, coagulation, clinical chemistry, biomarkers and cytokine production.

Adverse effects in the heart were observed at 300 μg/kg and consisted of minimal to mild degeneration/necrosis and an increased severity of mononuclear cell infiltration (mild severity vs. minimal severity in concurrent controls) at 300 μg/kg. Although the cardiac findings occurred at 300 μg/kg, there were no changes in electrocardiography, respiration rate, blood pressure, or heart rate associated with the cardiac findings.

Figure 6A:
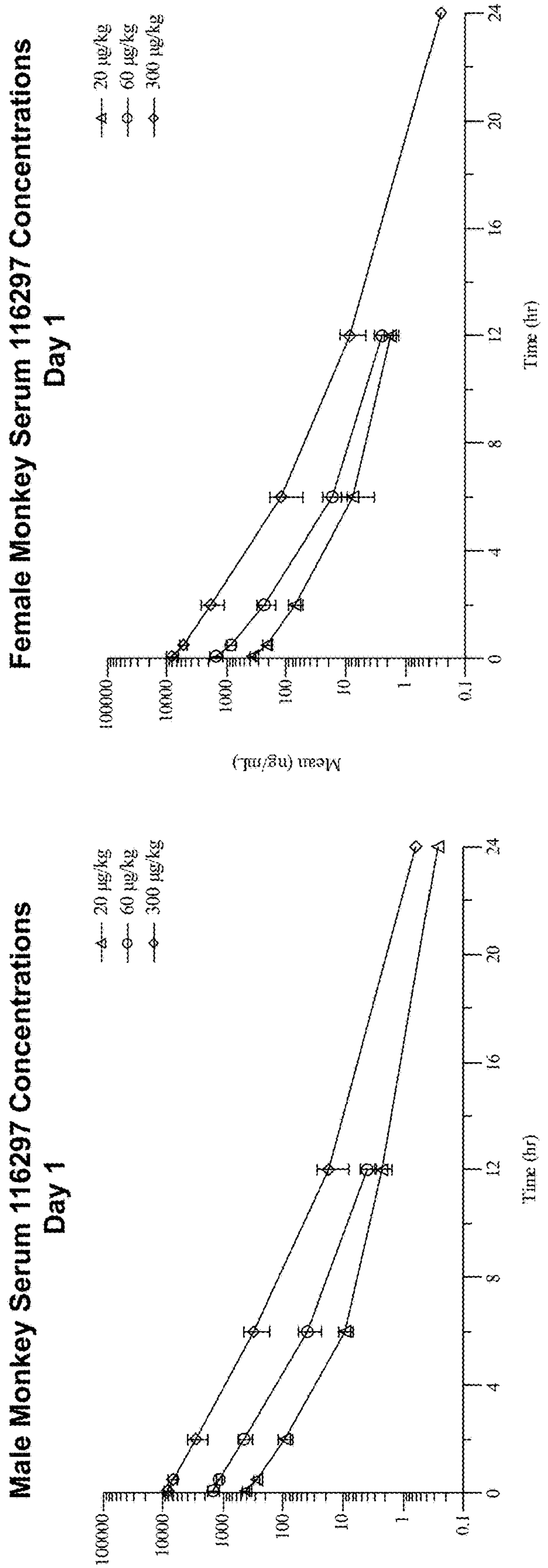
FIG. 6A shows mean serum 116297 concentrations in male (left panel) and female (right panel) cynomolgus monkeys following intravenous bolus injection of 116297 on Day 1.
Figure 6B:
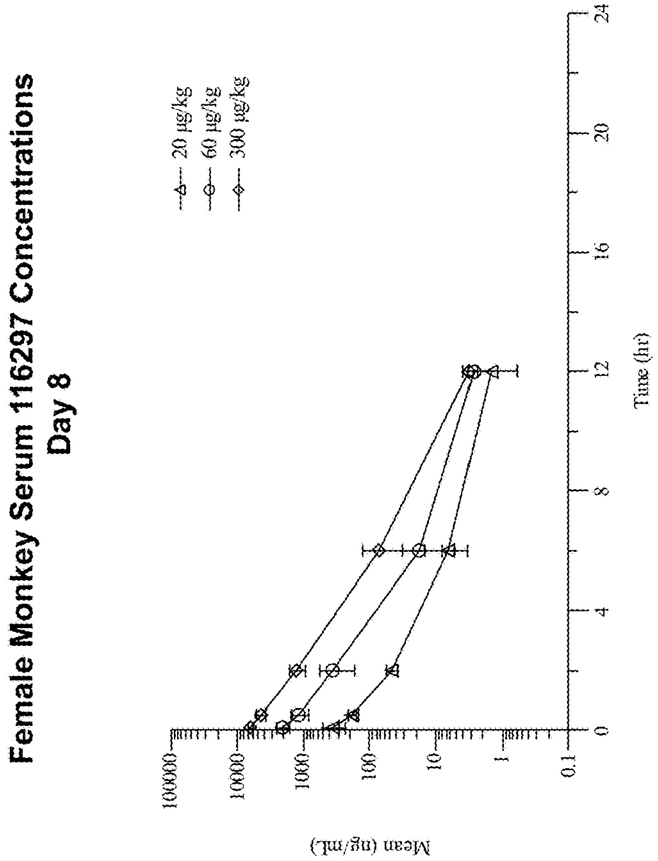
FIG. 6B shows mean serum 116297 concentrations in male (left panel) and female (right panel) cynomolgus monkeys following intravenous bolus injection of 116297 on Day 8.
Figure 6B:
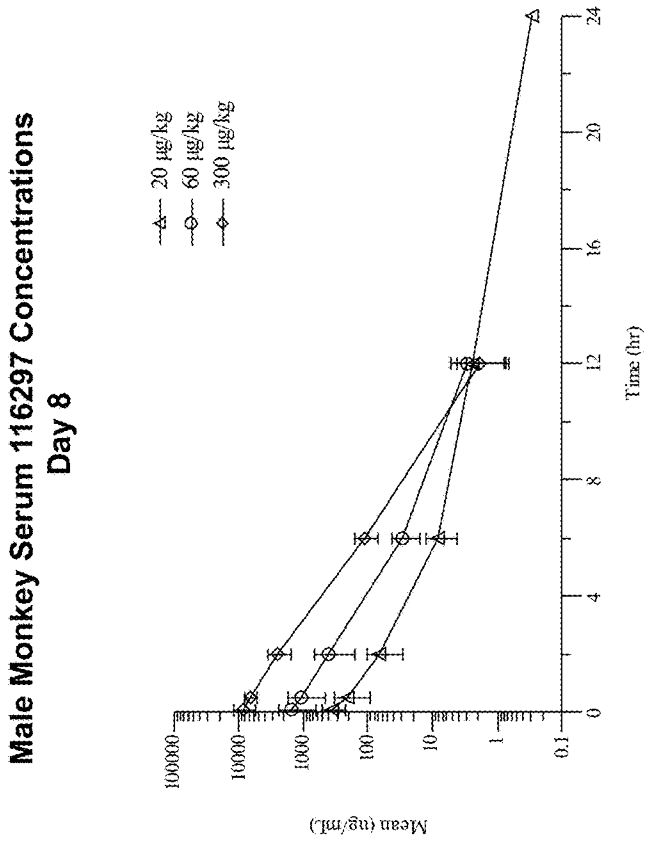

The serum concentrations of 116297 were observed up to 12 hours post-dose on Days 1 and 8 for a majority of male and female monkeys (FIG. 6A and FIG. 6B). Serum concentrations were below the lower limit of quantification for samples collected at pre-dose and post-dose on Days 15 and 22 and at 24 hours post-dose on Day 22. Most male and female monkeys developed ADA on Days 8, 15, 23, 29, and 36 (data not shown). There were no striking gender differences observed in the toxicokinetics of 116297 in cynomolgus monkeys.

In summary, administration of 116297 by intravenous injection once weekly on Days 1, 8, 15, and 22 was tolerated in monkeys at levels up to 300 μg/kg. Based on the results of this study, the no-observed-adverse-effect level (NOAEL) was 60 μg/kg and the highest non-severely toxic dose (NSTD) was 300 μg/kg.

Example 4. Phase I Study of 116297 in Humans with Solid Tumors

This Phase I study is designed to test the safety, tolerability, and efficacy of 116297 in subjects with advanced cancer (solid tumors) that express PD-L1. In Part A of the study, the primary objectives are to evaluate the safety and tolerability of 116297 and to determine the maximal tolerated dose (MTD). In Part B of the study, the primary objectives are to confirm the recommended Phase 2 dose (RP2D), and to evaluate efficacy of 116297 by using the objective response rate (ORR). The primary, secondary, and exploratory objectives and endpoints are shown in Table H below. The study will be conducted in two parts, Part A and Part B.

TABLE H

Objectives and Endpoints of the Phase I Clinical Trial

| OBJECTIVES | ENDPOINTS |
|---|---|
| Primary | |
| PART A: To evaluate the safety and tolerability of 116297 in subjects with advanced cancer (solid tumors) and determine the maximum tolerated dose (MTD). | incidence of adverse events (AEs), including dose-limiting toxicities (DLTs), inclusive of physical exam findings, laboratory abnormalities, and/or subject-reported symptoms |
| PART B: To confirm the recommended phase 2 dose (RP2D). | incidence of adverse events (AEs) |
| PART B: To evaluate efficacy of 116297 in subjects with advanced cancer by using objective response rate (ORR) | objective response using Response Evaluation Criteria in Solid Tumors (RECIST) 1 |
| Secondary (Parts A and B) | |
| To characterize the PK profile of 116297 in subjects with advanced cancer. | PK parameters:<br>maximum observed plasma concentration ($C_{max}$)<br>time of maximum observed plasma concentration ($t_{max}$)<br>the area under the concentration-time curve (AUC) from time zero to the last measurable concentration ($AUC_{0-t}$),<br>total exposure ($AUC_{0-\infty}$)<br>clearance (CL)<br>volume of distribution at steady-state ($V_{ss}$) |
| To assess additional efficacy parameters | duration of response (DOR)<br>progression-free survival (PFS)<br>overall survival (OS) |
| To evaluate the immunogenicity of 116297 in subjects with advanced cancer. | anti-drug antibodies (ADA) |
| Exploratory (Parts A and B) | |
| To evaluate the immunogenicity of 116297 in subjects with advanced cancer. | neutralizing antibodies (NAb) |
| To evaluate efficacy of 116297 in subjects with advanced cancer by using objective response rate (ORR) | objective response using immune-related RECIST (irRECIST) |
| To explore the immune response to 116297 treatment | change from baseline in peripheral blood mononuclear cells and respective T cell subsets |
| To correlate the pharmacodynamic markers of cancer under study with the , tumor response to 116297 in subjects with advanced cancer. | intensity of PD-Ll expression by immunohistochemistry staining in biopsied metastatic tumor tissue (tumor cells immune cells) and in circulating tumor and immune cells, correlating with tumor response |
| Correlate pharmacodynamic effect of CMV antigen presentation with tumor response during cycle 2 | change from baseline in tumor biopsy samples in: activated T cells to CMV antigen; comparison of T cell subsets from metastatic tumor biopsy and circulation |
| If warranted by the study results, to evaluate the exposure-response relationship for 116297 | PK, pharmacodynamic, safety, and tumor response variables |
| Pharmacodynamics | Serum cytokine levels<br>sPD-L1 |
| To assess Quality of Life with 116297 treatment | European Organization for the Research and Treatment of Cancer-quality of life questionnaire core 30 (EORTC-QLQ-C30) |

Key Inclusion Criteria for Part a of the Study Include:

(1) Subject must have histologically confirmed, unresectable, locally advanced or metastatic PD-L1-expressing solid cancer not amenable to standard treatment, standard treatment is not available, or standard treatment would not be in the subject's best interest.

(b) Any level of PD-L1 expression that is assessed using any FDA-approved PD-L1 immunohistochemistry (IHC) assay is accepted. The PD-L1 assessment should have been performed on the most recent available tissue for a site of metastatic disease (if possible).

(c) Subjects must also have evaluable or measurable disease.

Key Inclusion Criteria for Part B of the Study Include:

(1) Subject must have histologically confirmed, unresectable, locally advanced or metastatic PD-L1-expressing solid cancer not amenable to standard treatment, standard treatment is not available, or standard treatment would not be in the subject's best interest.

(a) PD-L1 expression must be assessed at screening using VENTANA SP263 PD-L1 assay on tissue from a site of metastatic disease. The VENTANA SP263 PD-L1 assay is an FDA-approved diagnostic IHC test for PD-L1 in subjects. For this purpose, recent archived tissue suitable for PD-L1 expression assessment by IHC (obtained after the last treatment and within 6 months) or fresh biopsy material can be used. The PD-L1 assessment must show at least 5% vCPS (visually estimated Combined Positive Score) for eligibility.

(b) The subject must have at least one measurable tumor lesion according to RECIST 1.1.

(c) Arm 1: Histologically confirmed recurrent or metastatic NSCLC not amenable to therapy with curative intent. Subjects with driver mutations are only eligible if they have received all appropriate targeted therapies.

(d) Arm 2: Histologically confirmed recurrent or metastatic SCCHN (oral cavity, oropharynx, hypopharynx, or larynx) not amenable to therapy with curative intent. Subjects who refuse radical resection are eligible. The tumor must be platinum resistant or the subject ineligible for platinum therapy due to hypersensitivity or concerns with ototoxicity. Squamous cell carcinoma of any other primary anatomic location in the head and neck, subjects with SCCHN of unknown primary, and subjects with skin SCC of the head and neck are not eligible for this cohort.

(e) Arm 3: Subjects with any other relapsed or refractory PD-L1 positive solid tumor who received PD-1/PD-L1 treatment. Subjects with PD-L1 positive solid tumor types, for which PD-1/PD-L1 treatment is not approved, could be enrolled at the Investigator's discretion and after discussion with the Medical Monitor.

Key Inclusion Criteria for Part a and Part B of the Study Include:

(1) Subject must have ECOG performance score of 0 to 1.

(2) Prior treatment must include a checkpoint inhibitor (i.e., PD-1 inhibitors or PD-L1 inhibitors with or without CTLA-4 inhibitors) if there is an approved checkpoint inhibitor for the specific cancer type. Subjects may also have received checkpoint inhibitors in an investigational setting. Subjects with PD-L1 positive solid tumor types, for which PD-1/PD-L1 treatment is not approved, could be enrolled at the Investigator's discretion and after discussion with the Medical Monitor.

(3) Subject must have adequate bone marrow function (administration of blood products and growth factors is not allowed within 2 weeks prior screening laboratory tests): (a) absolute neutrophil count (ANC) ≥1,500/μL; (b) platelet count ≥100,000/μL; and (c) hemoglobin ≥8.0 g/dL.

(4) Subject must have adequate renal function, based on estimated creatinine clearance (eCrCl)≥50 mL/min, calculated by the Cockcroft Gault equation. The eCrCl result ≤50 mL/min may be verified by measured creatinine clearance (mCrCl) based on the 24-hour urine collection. Subjects with mCrCl ≥50 mL/min will be eligible irrespective of the eCrCl result calculated by the Cockcroft-Gault equation.

(5) Subject must have adequate hepatic function, as determined by: (a) total bilirubin (or direct bilirubin for subjects with Gilbert's disease) <1.5×ULN; (b) AST ≤3×ULN (or ≤5×ULN if liver metastasis); and (c) ALT ≤3×ULN (or ≤5×ULN if liver metastasis).

Subject must have adequate serum albumin (albumin ≥2.5 g/dL).

Women of reproductive potential must have a negative highly sensitive pregnancy test within 72 hours before the start of treatment. Women who are postmenopausal (>1 year since last menstrual cycle) or permanently sterilized (e.g., bilateral tubal occlusion, hysterectomy, bilateral salpingectomy) may be considered as not of reproductive potential.

Subjects of reproductive potential must agree either to abstain continuously from heterosexual intercourse or use a highly effective birth control method from signing the informed consent until the short-term follow-up visit for females and until 90 days after the last dose of 116297.

Key Exclusion Criteria for Part a of the Study Include:

Subjects without available tissue from a site of metastatic disease or easily biopsiable lesion (biopsy sites of non-significant risk), or unwilling to consent to biopsy.

Key Exclusion Criteria for Part B of the Study Include:

Subjects without easily biopsiable lesions (biopsy sites of non-significant risk).

Key Exclusion Criteria for Parts A and B of the Study Include:

(1) History or current evidence of another neoplastic disease except cervical carcinoma in situ, superficial noninvasive bladder tumors, curatively treated Stage I-II non-melanoma skin cancer or any previous cancer curatively treated >2 years before the start of treatment.

(2) Active autoimmune disease currently under treatment or required systemic treatment within 2 years. Replacement therapy (e.g., thyroxine, insulin, or physiologic corticosteroid replacement therapy for adrenal or pituitary insufficiency) is allowed. Subjects who have not required systemic treatment of an auto-immune disease for at least 2 years may be enrolled if permission is provided after discussion with the Medical Monitor.

(3) Ongoing >Grade 1 immune-related toxicity caused by prior CPI therapy (i.e., PD-1 inhibitors, PD-L1 inhibitors, or CTLA-4 inhibitors). Subjects with stable endocrinological AEs e.g., hypothyroidism, adrenal insufficiency, hypopituitarism, or diabetes mellitus, and have been on a stable dose for at least 2 weeks before screening are eligible.

(4) Evidence of active noninfectious ≥Grade 2 pneumonitis or current evidence of ≥Grade 3 other underlying pulmonary disease.

(5) Received any of the following PD-L1 inhibitors within the following time periods prior to the first dose of 116297: (a) atezolizumab: 12 months; (b) durvalumab: 7 months; and/or (c) avelumab: 2 months.

(6) Any concurrent cancer treatment, apart from local treatment of non-target lesions for palliative intent (e.g., local surgery or radiotherapy).

(7) Prior radiation therapy within 4 weeks before the start of study treatment. A lesion in a previously irradiated area can only be considered target lesion if there has been radiographical disease progression since the end of radiation therapy.

(8) Received approved or investigational treatment for the disease under study (except PD-L1 inhibitors where the exclusion criterion described above applies) within 4 weeks before the start of treatment. For small molecules (MW<0.9 kDa), the washout is 5 half-lives or at least 2 weeks.

(9) Subjects that have had allogeneic tissue or solid organ transplantation.

(10) Current evidence of new or growing central nervous system (CNS) metastases during screening. Subjects with known asymptomatic CNS metastases will be eligible if they meet the following criteria: (a) Received radiotherapy or another appropriate therapy for CNS metastases; and (b) Have stable CNS disease on the computed tomography (CT) or magnetic resonance imaging (MM) scan within 4 weeks before screening compared with prior neuro imaging.

(11) Major surgical procedure within 28 days prior to the study treatment.

(12) History or current evidence of significant cardiovascular disease before the start of treatment, including but not limited to, the following conditions:

(a) Angina pectoris requiring anti-anginal medication, (chest pain: CTCAE Grade ≥2).

(b) Clinically significant valvular disease.

(c) Myocardial infarction within 12 months prior to the start of treatment.

(d) Arterial thrombosis or pulmonary embolism within 3 months before the start of treatment.

(e) History of Grade ≥2 symptomatic congestive heart failure (CHF) or New York Heart Association (NYHA) criteria Class ≥II.

(f) Left ventricular ejection fraction (LVEF) <55%, assessed preferably by Echo or multiple-gated acquisition (MUGA) scan, within 28 days before starting study treatment.

(g) High-risk uncontrolled arrhythmias (i.e., atrial tachycardia with a heart rate >100/min at rest and upon repeated testing, significant ventricular arrhythmia (CTCAE Grade ≥2 [ventricular tachycardia], or higher-grade atrioventricular [AV]-block [second degree AV-block Type 2 [Mobitz 2] or third-degree AV-block]). Subjects receiving digoxin, calcium channel blockers, or beta-adrenergic blockers are eligible at the investigator's discretion after consultation with medical monitor if the dose has been stable for ≥2 weeks before the start of treatment with 116297.

(h) Any of the following within 3 months before the start of treatment: pericarditis (any CTCAE Grade), pericardial effusion (CTCAE Grade ≥2), non-malignant pleural effusion (CTCAE Grade ≥2) or malignant pleural effusion (CTCAE Grade ≥3) (subjects with pleural effusion that is manageable and stable >3 months prior to study are eligible).

(i) QTcF≥470 ms (average from 3 QTcF values on the triplicate 12-lead electrocardiogram [ECG]) at screening. In subjects with right bundle branch block, additional calculations will be performed to calculate the QT equivalent JT, and depending on the result the subject may be eligible with the agreement of the Medical Monitor.

(13) Current evidence of uncontrolled human immunodeficiency virus (HIV), hepatitis B virus (HBV), or hepatitis C virus (HCV) at screening. Serology testing is not required if seronegativity is documented in the medical history, and if there are no clinical signs suggestive of HIV or hepatitis infections, or suspected exposure. The following exceptions apply for subjects with positive viral serology:

(a) Subjects with HIV and an undetectable viral load and CD4+ T-cell (CD4+) counts ≥350 cell s/mL may be enrolled, but must be taking appropriate opportunistic infection prophylaxis, if clinically relevant.

(b) Subjects with positive HBV serology are eligible if they have an undetectable viral load and the subject will receive antiviral prophylaxis for potential HBV reactivation per institutional guidelines.

(c) Subjects with positive HCV serology are eligible if quantitative PCR for plasma HCV RNA is below the lower limit of detection. Concurrent antiviral HCV treatment per institutional guidelines is allowed.

(14) Current treatment requiring systemic steroids at doses >20 mg/day prednisone equivalent.

(15) Subjects with a history of hypersensitivity or serious toxic reactions to kanamycin or other aminoglycosides.

(16) Subjects with unintentional weight loss greater than 10% of their body weight over the preceding 2 months or less before screening.

Female subjects who are pregnant or breastfeeding.

History or evidence of any other clinically significant disorder, condition or disease (with the exception of those outlined above) that, in the opinion of the Investigator or Medical Monitor, if consulted, would pose a risk to subject safety or interfere with the study evaluation, procedures or completion.

Figure 7A:
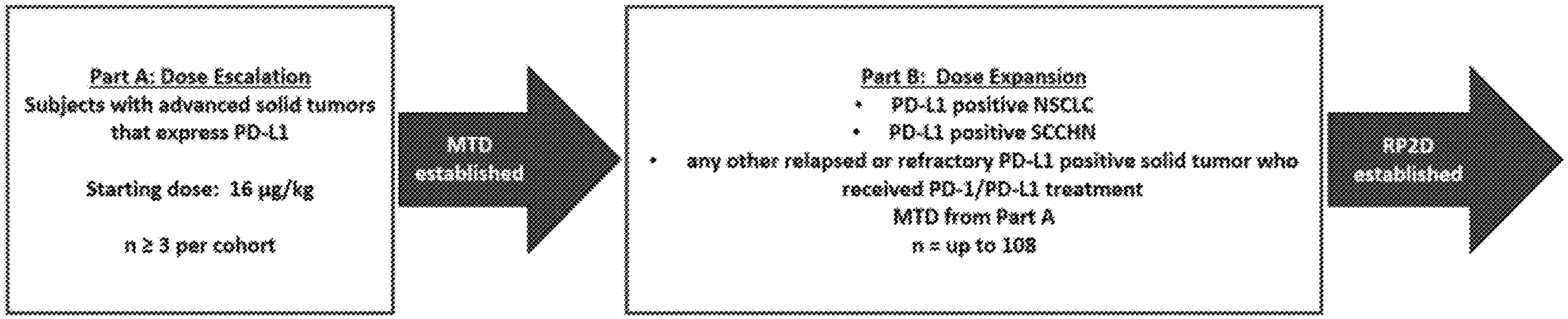
FIG. 7A shows a schema of the overall design of a Phase 1 clinical study to test the safety and efficacy of 116297, which will occur in two parts (Part A and Part B). In part A, the MTD of 116297 will be determined in subjects with advanced solid tumors. In part B, the RP2D will be established in subjects with advanced cancer. PD-L1 expression will be confirmed on tissue from a site of metastatic disease. DL: dose level; MTD: maximum tolerated dose; NSCLC: non-small cell lung carcinoma; PD-L1: programmed death-ligand 1; RP2D: recommended phase 2 dose.
Figure 7B:
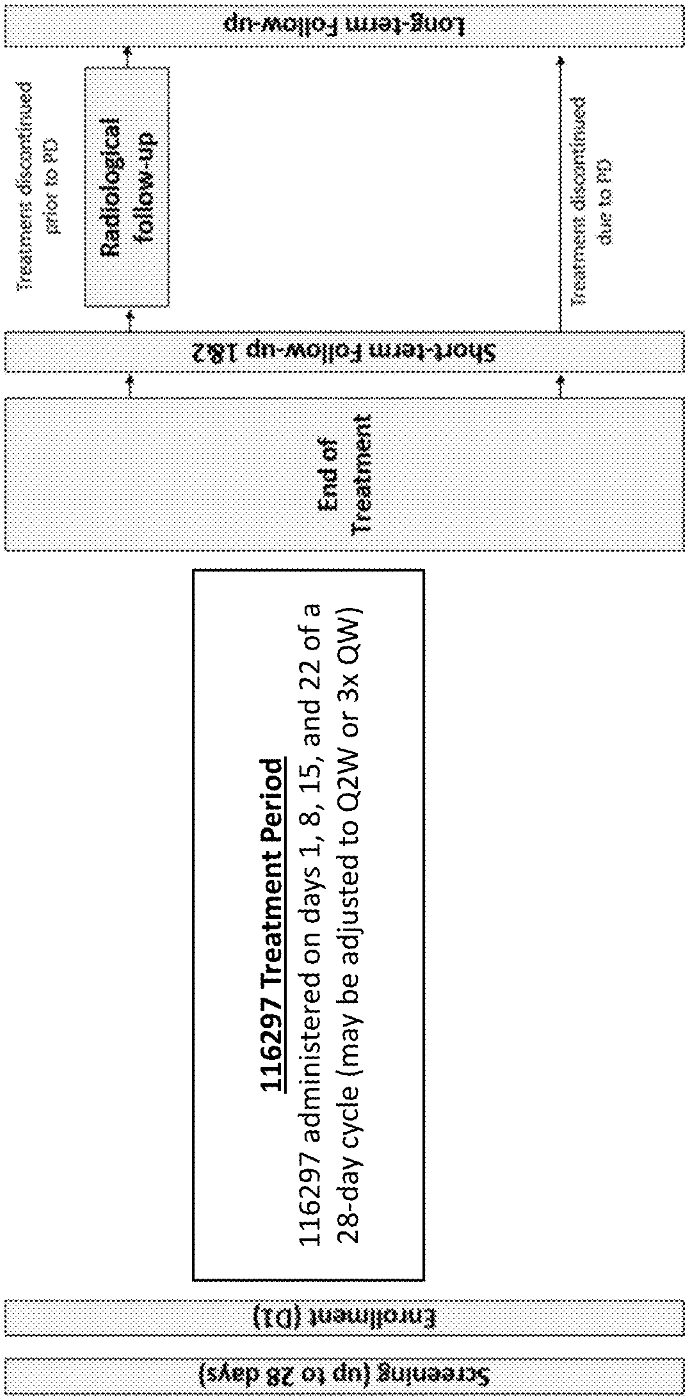
FIG. 7B shows a schema of the study design for Part A.
Figure 7C:
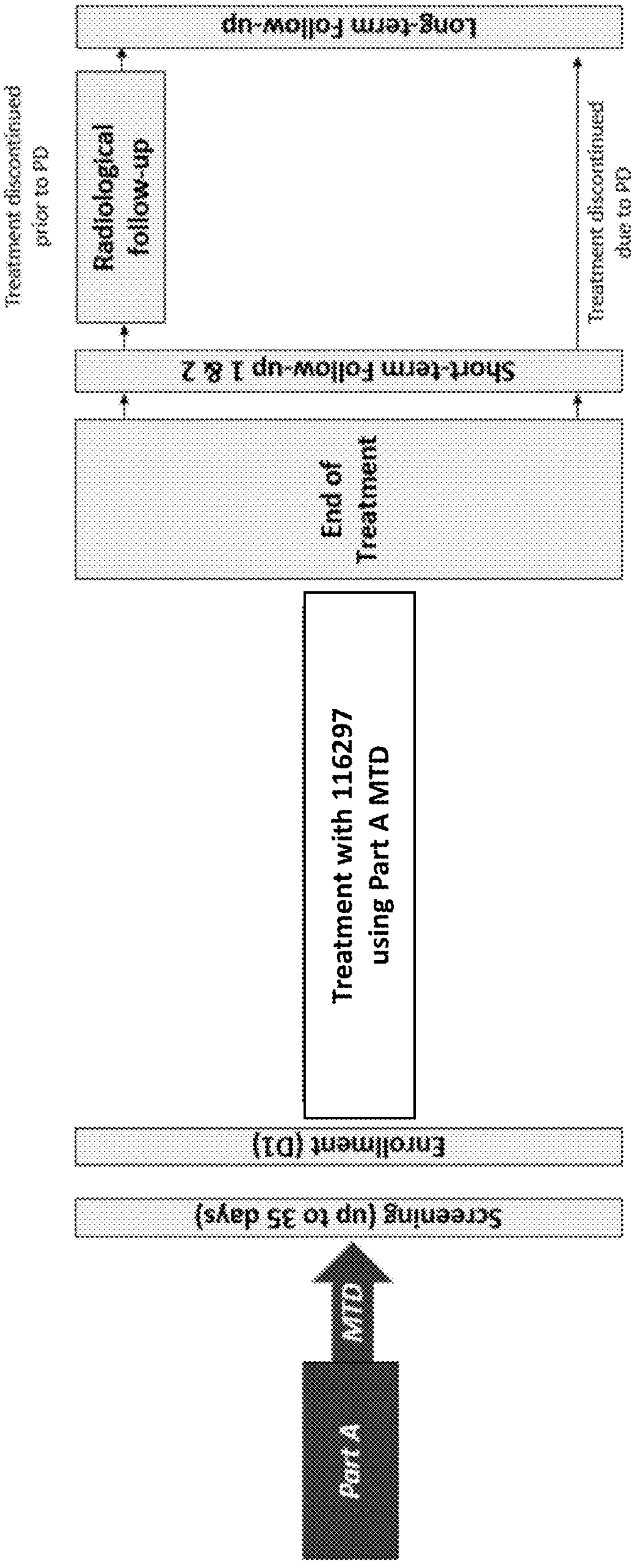
FIG. 7C shows a schema of the study design for Part B.

Overall Study Design:

This Phase I study of 116297 will be conducted in two parts: Part A (Dose Escalation) and Part B (Dose Expansion). Part A will estimate the maximum tolerated dose (MTD) and Part B will identify the dose to be studied in the phase 2 program (RP2D). The overall study design is shown in FIG. 7A and the study designs for Part A and Part B are shown in FIG. 7B and FIG. 7C, respectively.

Part a, Dose Escalation:

Part A will use a modified toxicity probability interval (mTPI-2) design to determine the MTD in subjects with advanced cancer (solid tumors). The mTPI-2 design is implemented in a fashion similar to the traditional 3+3 design, but is more flexible and possesses superior operating characteristics that are comparable to those of the more complex model-based designs, such as the continual reassessment method (CRM).

The mTPI-2 design includes the following steps: Step 1: Subjects in the first cohort are treated at dose level 1; at least 3 subjects will receive study treatment before escalating to dose level 2. Step 2: To assign a dose to the next cohort of subjects, dose escalation/de-escalation will be conducted according to FIG. 8. Note the following: (a) "De-escalate and Eliminate" refers to eliminating the current and higher doses from the trial to prevent treating any future subjects at these doses because they are overly toxic. (b) If a dose is eliminated, automatically de-escalate the dose to the next lower level. When the lowest dose is eliminated, the trial is stopped for safety. In this case, no dose can be selected as the MTD. (c) If none of the preceding actions (i.e., escalation, de-escalation or elimination) is triggered, continue to treat the new subjects at the current dose. (d) If the current dose is the lowest dose and the rule indicates dose de-escalation, treat the new subjects at the lowest dose unless the number of dose-limiting toxicities (DLTs) reaches the elimination boundary, at which point the trial is stopped for safety. (e) If the current dose is the highest dose and the rule indicates dose escalation, treat the new subjects at the highest dose.

Step 3: Repeat step 2 until the expected sample size of 24 is reached or stop the trial if the number of subjects treated at the current dose reaches 12.

Part B, Dose Expansion:

After the MTD has been determined in Part A of the study, Part B of the study will enroll additional subjects at the MTD, to further explore safety and efficacy and determine RP2D.

Study Treatment:

Subjects must be treated and observed in an area with equipment for resuscitation including assisted ventilation and emergency treatments or have access to emergency facilities through an emergency call. Adequate management and treatment of infusion related reactions (IRRs), anaphylactic reactions or other hypersensitivity events will be assured during the treatment period.

116297 is the investigational medicinal product in this study. 116297 will be supplied as a sterile aqueous solution (pH 5.5) in a 2 mL vial containing 2.0 mL of 116297 (0.5 mg/ml) in a formulation buffer comprised of sorbitol, sodium citrate, and polysorbate 20.

Vials of 116297 are shipped and stored frozen until thawed for use. 116297 is stable at room temperature for up to 24 hours.

116297 is diluted in normal saline for intravenous (IV) administration. All doses should be administered over 30 minutes (±5 min) through an IV line.

116297 will be administered over 30 minutes (±5 min) intravenous (IV) infusion on days 1, 8, 15, and 22, of a 28-day cycle. 116297 doses may be administered within a 2-day window if appropriate.

The dose of 116297 will be calculated based on the subject's baseline body weight. The body weight will be measured before the first dose of 116297 in each cycle. If the body weight has changed by ≥10% from the baseline value (pre-dose on cycle 1 day 1), this will require re-calculation of the dose.

The starting dose of 116297 is 16 μg/kg of the subject's baseline body weight. This dose may be reduced, for example to 8 μg/kg of the subject's baseline body weight after the first cycle.

Dose reductions of 116297 are allowed for treatment-related toxicities.

The first 2 subjects in each Cohort will receive their cycle 1, day 1 dose at least 2 days apart. The following subjects in each cohort may be enrolled concurrently. In each cohort, evaluable subjects will be assessed for DLTs through cycle 1. Dose escalation, dose de-escalation, or enrollment of additional subjects into the same dose cohort will be determined once all subjects are available for assessment in Cohort 1.

Dose escalation between cohorts will be performed: (1) If ≤33% (i.e., 0 of 3 or ≤1 of 6) of subjects experiences a DLT: 1.33(×) mcg/kg QW of a 28-day cycle. (2) If no DLT occurred and if at least 1 patient experiences a Grade 2 116297-related non-DLT: 1.5(×) mcg/kg QW of a 28-day cycle. (3) If no DLT occurred and if no subjects experience a Grade ≥2 116297-related non-DLT (i.e., if no 116297-related AEs occur or if all 116297-related AEs are Grade 1): 2(×) mcg/kg QW of a 28-day cycle.

Lower dose increases (i.e., 25% increase) of 116297 may be considered based on the frequency and severity of non-DLT AEs.

Following 25% or 33% dose escalations of 116297, a higher dose escalation increment (i.e., 50%) may be re-instituted if no Grade ≥3 116297-related non-DLT AEs occur in 2 consecutive cohorts.

Dose de-escalation will be performed between cohorts as follows: (1) DLTs occurring during week 1 or between dosing weeks 2 and 3: dose is reduced with the same schedule (QWK×4). (2) DLTs occur during week 2: dose schedule is modified to QOWK. (3) DLTs occur between weeks 3 and 4: dose schedule is modified to QWK×3. (4) DLTs do not clearly fit into a pattern: dose level and/or schedule change will be decided by the Safety Committee.

Subjects will be monitored in the clinic after infusion for a minimum of 6 hours during the first cycle and for at least 3 hours beyond the first cycle. All subjects will be evaluated for adverse events (AEs) prior to each infusion during all cycles of 116297 treatment.

A minimum of 5 days but no more than 14 days should elapse between cycles. If greater than 14 days or fewer than 5 days elapse, the investigator must consult with the medical monitor before initiating the next cycle of treatment.

116297 will be administered until disease progression, unacceptable toxicity, death, withdrawal of consent, or another reason for withdrawal. For subjects with clinical benefit (confirmed complete response (CR), partial response (PR) for at least 12 weeks, or stable disease (SD) for at least 24 weeks), the treatment can be temporarily suspended and resumed if it is in the subject's best interest. However, the subject needs to attend the scheduled imaging assessments during the drug holiday.

General Study Periods:

Part A: Screening procedures will be performed within 28 days before the start of treatment on Cycle 1 Day 1 (C1D1), except safety labs which must be within 14 days before treatment start and the radiographical disease assessment which may be performed within 6 weeks before C1D1.

Part B: Screening procedures will be performed within 35 days before the start of treatment, except for the radiographical disease assessment which may be performed within 6 weeks before C1D1. The first assessment performed is the biopsy, all the other screening assessments can only be done if the PD-L1 positive result is received. Safety labs must be within 14 days before treatment start, other assessments (including echo) within 28 days.

After all eligibility criteria have been fulfilled, the subject may start treatment.

The treatment period begins on C1D1 when the first dose of 116297 is administered to a subject. Treatment with 116297 will continue until death, disease progression, unacceptable toxicity, withdrawal of consent, or another reason for withdrawal, or until study discontinuation.

An End of Treatment (EoT) visit will be performed at the end of the treatment period. The EoT visit should occur within 14 days after the last dose of 116297, and before start of new therapy except for subjects who withdrew consent and objected to further data collection, or were lost to follow up. The EoT visit should be performed during the clinic visit. EoT visit may be performed by telephone call if a subject cannot attend a clinic visit or has started a new anticancer treatment.

The Short-Term Follow-up visits (STFU 1 and 2) for safety assessment should occur 30 days (±7 days) and 90 days (±7 days) after the last dose of 116297, except for subjects who withdrew consent and objected to further data collection, started new anticancer therapy or another investigational drug, or were lost to follow-up. The STFU visits can be done via a clinic visit (recommended) or via a telephone call (if subject cannot attend a clinic visit or has started a new anticancer therapy). In such instances, missed assessments (e.g., laboratory assessments, physical examination) are not considered deviations.

The Long-term Follow-up (LTFU) visits should occur every 3 months (±30 days) after the STFU visit 2 for up to 24 months. Subjects who discontinue the study treatment for radiographical disease progression will be followed only for overall survival (OS). Subjects who discontinue the study treatment for reasons other than radiographical disease progression, will be followed for progression-free survival (PFS) and OS. The LTFU visits will be performed via a telephone call to collect information about death (if any), tumor status (relapsed or not), and the start of any new anticancer therapy or any other investigational drug since the last study visit/phone call. Subjects with CR, PR, or SD should also be followed for radiology assessment until PD, death, or new anticancer treatment. Radiology data can be obtained from existing medical records if assessments were performed as SOC between LTFU visits.

Assessments:

Radiological assessment of all anatomic regions involved with the underlying cancer will be performed. The original schedule needs to be maintained even if there is a delay is dosing. At each tumor assessment visit, all images will be interpreted by a radiologist according to RECIST 1.1 and irRECIST. In Part A of the study, radiological assessment of tumor response will be performed locally and in Part B of the study, radiological assessment will be performed centrally.

Complete response and partial response should be confirmed by repeated radiologic evaluation between 4 weeks to 8 weeks after the initial response assessment. For subjects treated beyond progression, radiologic evaluation must be repeated in 4 to 8 weeks from initial scan showing progression.

Subjects will complete The European Organization for Research and Treatment of Cancer Quality of Life Questionnaire (EORTC QLQ-C30) to assess the quality of life in cancer subjects across tumor types. It is a self-reporting 30-item generic instrument which assesses 5 functional domains (physical, role, emotional, cognitive, social), 9 symptom scales (fatigue, nausea and vomiting, pain, dyspnea, insomnia, appetite loss, constipation, diarrhea, financial difficulties), and a global health status/quality of life scale (Aaronson et al, 1993). The recall period is the past week. The QLQ-C30 will take approximately 9 minutes to complete.

Subjects will undergo safety assessments throughout the study. Safety assessments will include physical measurements (height, weight, BMI), a complete or abbreviated physical examination, vital signs (blood pressure, respiratory rate, heart rate, and body temperature), left ventricular ejection fraction, electrocardiograms, local laboratory assessments (viral serology and urinalysis), and clinical laboratory assessments (e.g., pregnancy test, chemistry, thyroid function, hematology, coagulation, HbA1c).

Blood samples will be collected prior to, during, and at specified times following 116297 infusion for determination of free 116297 drug concentrations in serum, which will be used for the assessment of the repeat-dose pharmacokinetics (PK) of 116297. The following PK parameters will be evaluated in plasma after IV administration, if calculable: maximum observed plasma concentration (Cmax), time of maximum observed plasma concentration (Tmax), area under the concentration versus time curve (AUC) from time zero to the last measurable concentration (AUCO-t), interpolated AUC to infinity (AUCO-∞), AUC over a dosing interval (AUCtau), total body clearance (CL), volume of distribution at steady-state (Vss), volume of distribution during terminal phase (Vz), and accumulation ratios compared to Day 1 dosing (R). Dose-proportionality will be assessed based on dose-normalized Cmax and AUC values.

Peripheral blood will be collected at various timepoints and B cells, T cells, NK cells, and CD14+ monocyte will be assessed by flow cytometry to determine effect on immune cells with high PD-L1 expression. Serum cytokines (IL-6, IL-8 and others), CRP, troponin, and soluble PD-L1 levels will be monitored during treatment.

Tumor tissue biopsy after treatment is mandatory in Part B, and will be stained for PD-L1 tissue expression, and CD4/CD8/CD14/CD16 immune cell expression.

Blood samples will be screened for anti-drug antibodies (ADAs) that bind 116297. All ADA-positive samples will have the titer reported and screened for neutralizing antibodies (NAb), reported as positive or negative. Other analyses may be performed, such as verifying the stability of antibodies to 116297.

Adverse Events:

The incidence of adverse events (AEs), including dose-limiting toxicities (DLTs), inclusive of physical exam findings, laboratory abnormalities, and/or subject-reported symptoms will be monitored throughout the study (Part A and Part B).

Example 5. Treatment of a Subject Having the HLA-A*02 Haplotype

As part of the Phase I study described in Example 4, one subject heterozygous for HLA-A*02 haplotype (and testing positive for anti-CMV IgG antibodies) was treated with 116297. The subject was dosed weekly at a level of 16 μg/kg during cycle 1, and this dose was reduced to 8 μg/kg starting in cycle 2. Blood samples were obtained periodically for analysis.

Figure 9A:
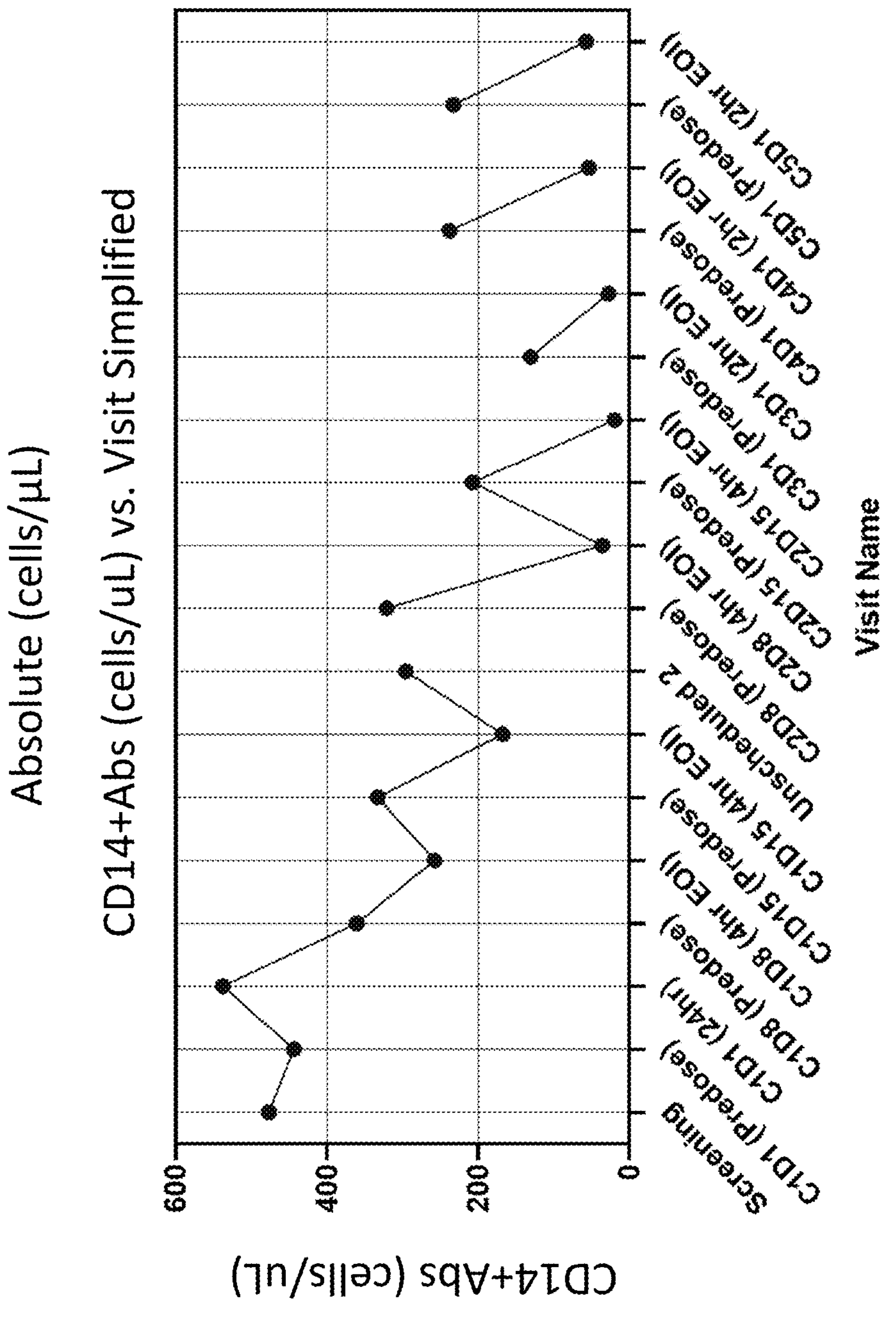
FIGS. 9A-9C show levels of CD14+ monocytes in blood samples obtained from a HLA-A2 CMV+ subject after treatment with 116297, over the course of 5 months of treatment.
Figure 9B:
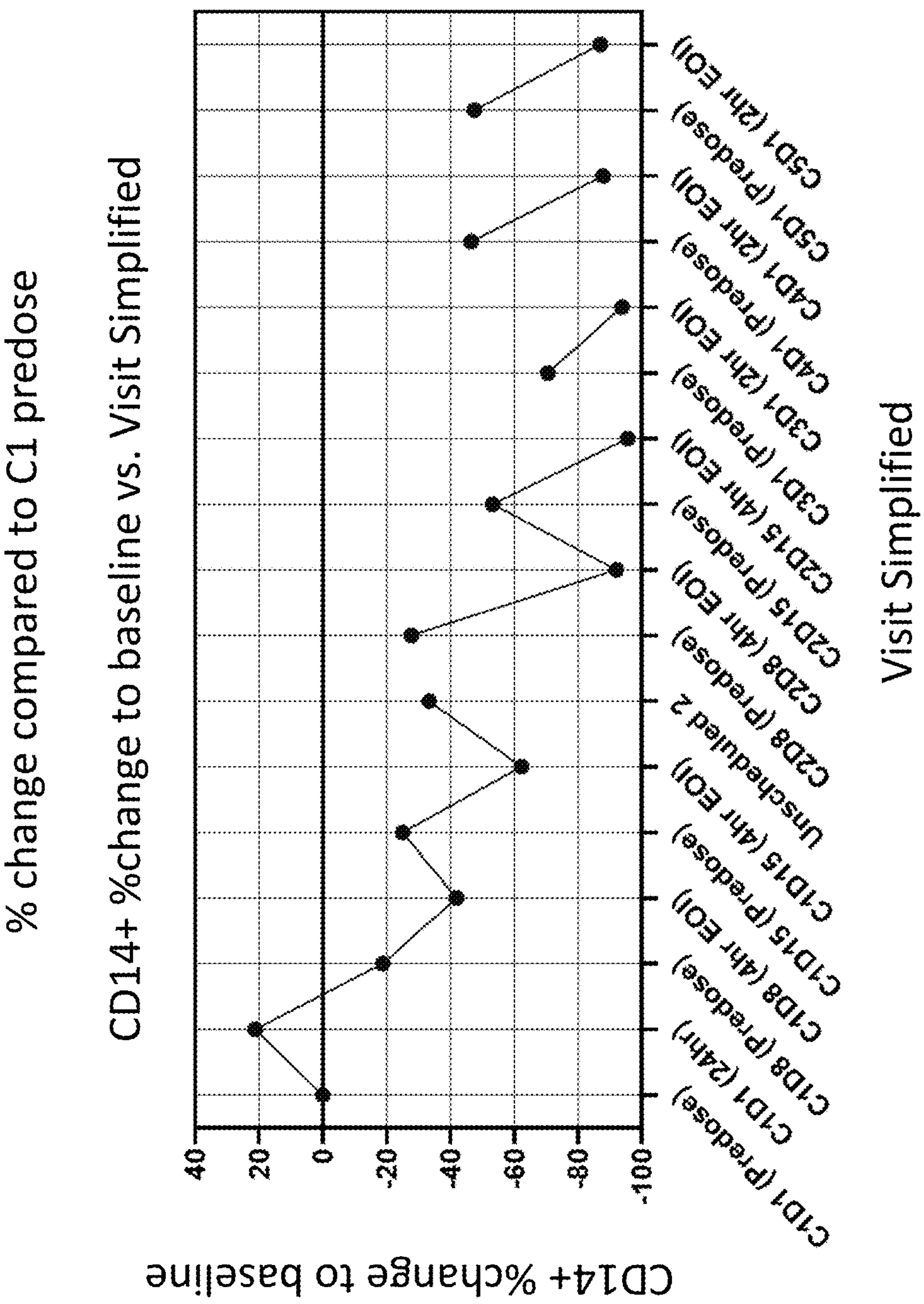
Figure 9C:
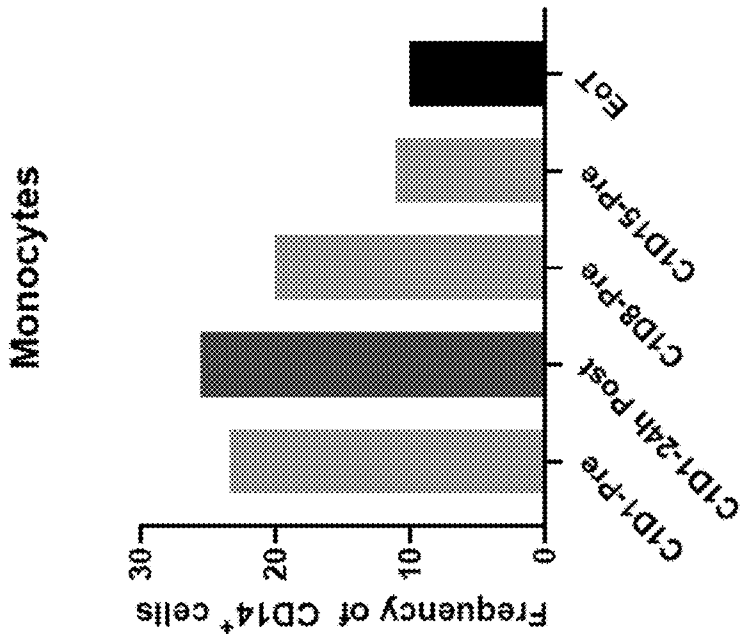

As a pharmacodynamic marker of 116297 target modulation in peripheral blood, CD14+ monocyte depletion was measured over the course of treatment. As shown in FIG. 9A-9C, the subject had greater than 95% monocyte depletion, and this level of depletion was maintained and is ongoing at 5+ months of dosing.

Figure 10:
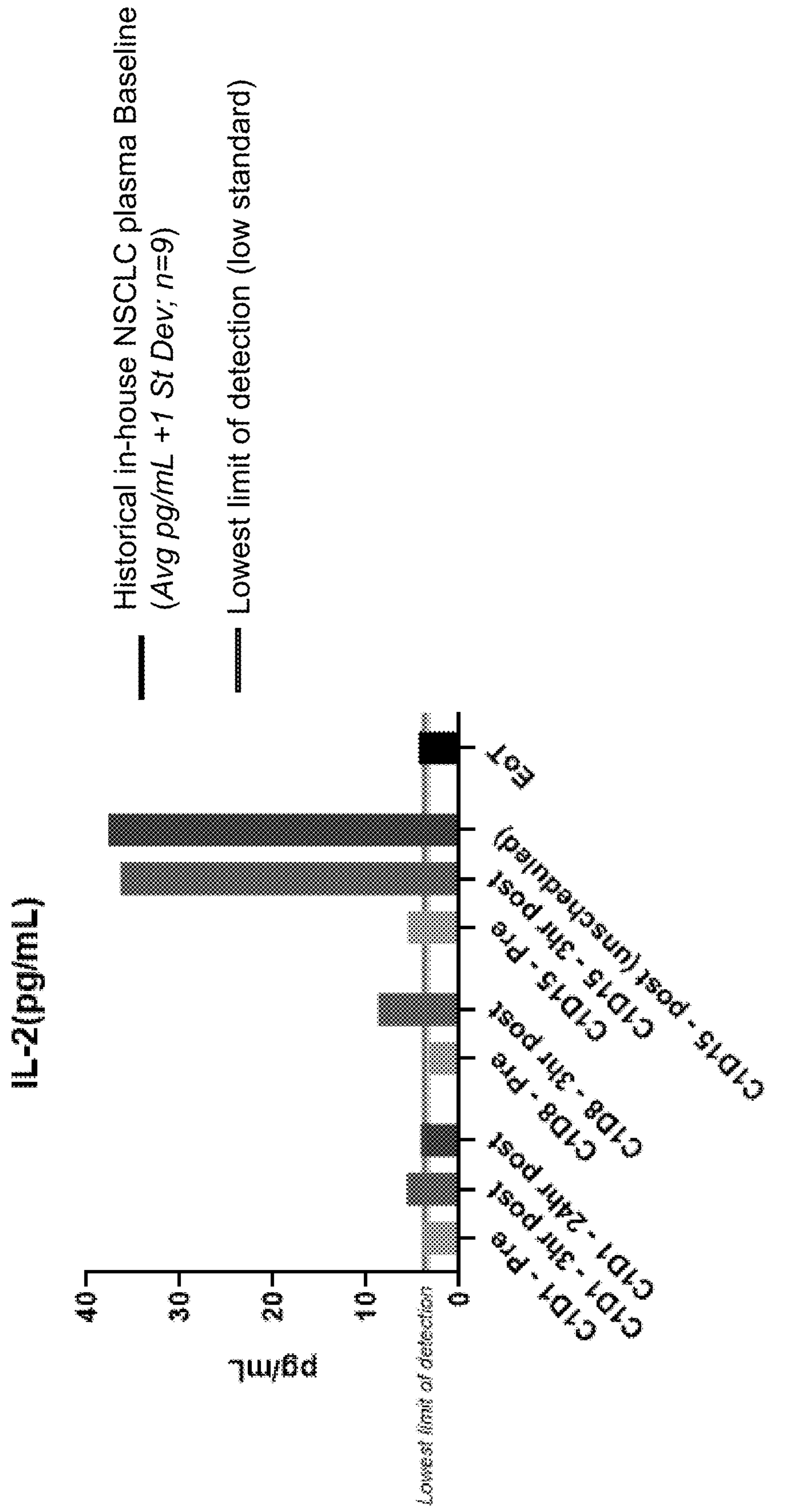
FIG. 10 shows level of IL-2 (pg/mL) in blood samples from the HLA-A2 CMV+ subject following treatment with 116297. Samples were obtained C1D1, C1D8, C1D15 and at the end of treatment (EoT), and were taken either pre-dosing, 3 hours post-dosing, or 24 hours post-dosing. Horizontal lines show lowest limit of detection, and historical in-house NSCLC plasma baseline. The historical in-house NSCLC plasma baseline is generated based on NSCLC patient samples, which serve as a negative control.
Figure 11:
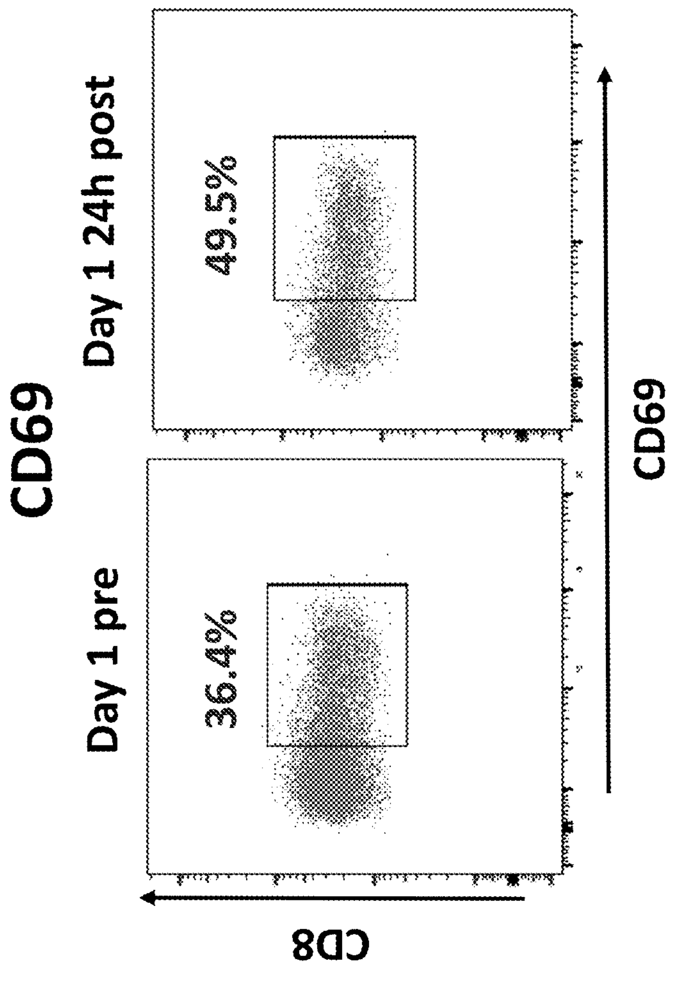
FIG. 11 presents flow cytometry data, showing numbers of CD8+ CD69+ cells before and after (i.e., 24 hours post) treatment with 116297. CD69 is an activated T-cell marker.

Significant increases in key cytokines including IL-2 (FIG. 10) and activated CD8+ T-cell markers including CD69 (FIG. 11) were noted. The highest increase in CD69+ CD8+ cells correlates to an increase in CMV T-cell frequencies at Day 1 (24 hours post-dose).

Figure 12A:
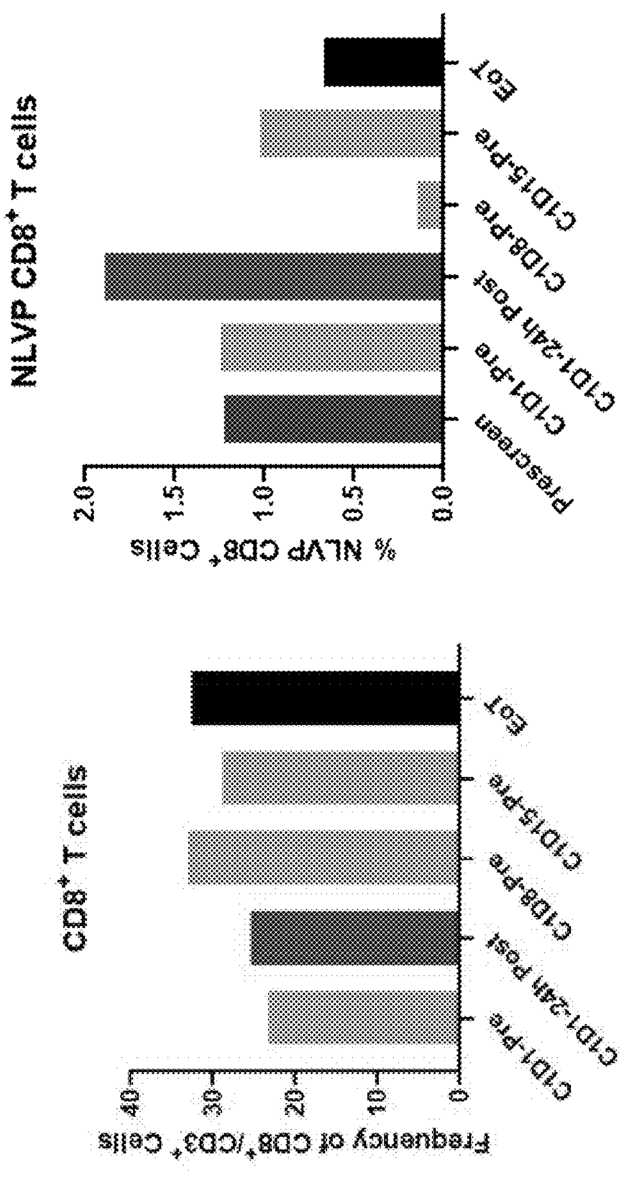
FIG. 12A shows numbers CD8+ T-cells (left panel) and CMV-specific CD8+ T-cells (right panel) in patient samples.
Figure 12B:
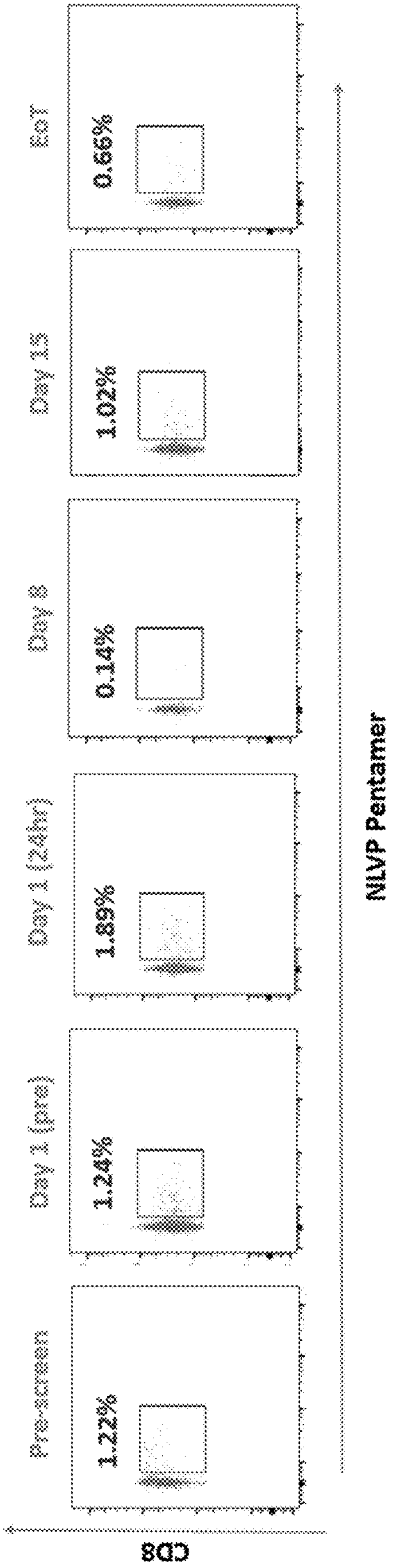
FIG. 12B shows changes in numbers of CD8+ CMV-specific T-cells patient samples over the course of treatment, as determined using flow cytometry. An initial increase of −50% in CMV antigen-specific T-cells was observed after dosing with 116297 with subsequent near-complete extravasation of CMV antigen-specific T-cells from the periphery despite a general increase in total peripheral CD8+ effector T-cells.

Pre-existing CMV specific T-cells were observed at approximately 1% in the subject (FIG. 12A). CMV-specific CD8 T-cells (i.e., expressing the NLVP CMV A2 peptide) increased after the first dose, and a marked decrease was observed by day 8 (FIG. 12B). A higher frequency of CMV specific T-cells was observed at day 1 (24 hours post treatment), relative to baseline. As shown in FIG. 12B, a drop in CMV specific T-cells was observed at day 8 post-treatment. Thus, this data shows an initial increase of −50% in CMV antigen-specific T-cells after dosing with 116297 with subsequent near-complete extravasation of CMV antigen-specific T-cells from the periphery despite a general increase in total peripheral CD8+ effector T-cells.

Taken together, the data suggests 116297 treatment led to successful expression of CMV antigen in the tumor cells, and caused antigen-specific T-cell expansion and AST activity. Without being bound by any theory, it is believed that this represents movement of the CMV specific T-cells into the tumor.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

NUMBERED EMBODIMENTS

Notwithstanding the appended claims, the following numbered embodiments also form part of the instant disclosure.

1. A pharmaceutical composition comprising: (i) a PD-L1 binding molecule comprising a polypeptide having the amino acid sequence of SEQ ID NO:1; and (ii) at least one pharmaceutically acceptable carrier or excipient.
2. The pharmaceutical composition of embodiment 1, wherein the concentration of the PD-L1 binding molecule is about 0.1 mg/mL to about 5 mg/mL.
3. The pharmaceutical composition of embodiment 1, wherein the concentration of the PD-L1 binding molecule is about 0.25 mg/mL, about 0.5 mg/mL, about 1 mg/mL, about 2 mg/mL, about 2.5 mg/mL, or about 5.0 mg/mL.
4. The pharmaceutical composition of embodiment 3, wherein the concentration of the PD-L1 binding molecule is about 0.5 mg/mL.
5. The pharmaceutical composition of embodiment 3, wherein the concentration of the PD-L1 binding molecule is about 1 mg/mL.
6. The pharmaceutical composition of any one of embodiments 1-5, wherein the at least one pharmaceutically acceptable carrier or excipient is selected from a co-solvent, a surfactant, a preservative, a viscosity modifier, a suspending agent, a buffer, an antioxidant, a chelating agent, a humectant, an emulsifying agent, a flocculating agent, and an isotonicity agent.
7. The pharmaceutical composition of any one of embodiments 1-5, wherein the at least one pharmaceutically acceptable carrier or excipient is a buffer.
8. The pharmaceutical composition of embodiment 7, wherein the buffer is a citrate buffer, a phosphate buffer, an acetate buffer, a succinate buffer, a histidine buffer, a Tris buffer, a tartrate buffer, a glycine buffer, a glutamate buffer, or a mixture thereof.
9. The pharmaceutical composition of embodiment 7, wherein the buffer is a citrate buffer.
10. The pharmaceutical composition of embodiment 9, wherein the buffer comprises sodium citrate at a concentration of about 5 mM to about 30 mM.
11. The pharmaceutical composition of embodiment 9, wherein the buffer comprises sodium citrate at a concentration of about 20 mM.
12. The pharmaceutical composition of any one of embodiments 1-5, wherein the at least one pharmaceutically acceptable carrier or excipient is an isotonicity agent.
13. The pharmaceutical composition of embodiment 12, wherein the isotonicity agent is a sugar or a sugar alcohol.
14. The pharmaceutical composition of embodiment 13, wherein the sugar or sugar alcohol is sorbitol, sucrose, or trehalose.
15. The pharmaceutical composition of any one of embodiments 1-5, wherein the at least one pharmaceutically acceptable carrier or excipient is a surfactant.
16. The pharmaceutical composition of embodiment 15, wherein the surfactant is polysorbate-20, polysorbate-80, or a combination thereof.
17. The pharmaceutical composition of any one of embodiments 1-16, wherein the composition comprises sorbitol and polysorbate-80.
18. The pharmaceutical composition of any one of embodiments 14 or 17, wherein the concentration of sorbitol is about 50 mM to about 300 mM.
19. The pharmaceutical composition any one of embodiments 14 or 17, wherein the concentration of sorbitol is about 200 mM.
20. The pharmaceutical composition of any one of embodiments 16-19, wherein the concentration of polysorbate-80 is about 0.005% (v/v) to about 0.015% (v/v).
21. The pharmaceutical composition of any one of embodiments 16-19, wherein the concentration of polysorbate-80 is about 0.01% (v/v).
22. The pharmaceutical composition of any one of embodiments 1-5, wherein the pharmaceutical composition comprises about 200 mM sorbitol, about 20 mM sodium citrate, and about 0.01% (v/v) polysorbate-80.
23. The pharmaceutical composition of any one of embodiments 1-22, wherein the pharmaceutical composition has a pH of about 5.2 to about 5.8.
24. The pharmaceutical composition of embodiment 23, wherein the pH is about 5.5.
25. The pharmaceutical composition of embodiment 23, wherein the pH is about 5.6.
26. The pharmaceutical composition of any one of embodiments 1-25, wherein the pharmaceutical composition is at least 99% (w/v) free of impurities.
27. The pharmaceutical composition of any one of embodiments 1-25, wherein the composition comprises no more than 1% (w/v) of impurities.
28. The pharmaceutical composition of embodiment 27, wherein the impurities comprise one or more of endotoxin, bioburden, host cell protein, host cell DNA, kanamycin, triton X-100, protein L, and glucan.
29. The pharmaceutical composition of embodiment 27, wherein the composition comprises endotoxin at a concentration of ≤5 EU/mL, ≤4 EU/mL, ≤3 EU/mL, ≤2 EU/mL, or ≤1 EU/mL.
30. The pharmaceutical composition of embodiment 27, wherein the composition comprises endotoxin at a concentration of ≤0.5 EU/mL.
31. The pharmaceutical composition of embodiment 27, wherein the composition comprises bioburden at a concentration of ≤1 CFU/mL.
32. The pharmaceutical composition of embodiment 27 wherein the composition comprises host cell protein at a concentration of ≤1 ng/mL.
33. The pharmaceutical composition of embodiment 27, wherein the composition comprises host cell DNA at a concentration of ≤0.1 ng/mL.
34. The pharmaceutical composition of embodiment 27, wherein the composition comprises kanamycin at a concentration of ≤250 ng/mL.
35. The pharmaceutical composition of embodiment 27, wherein the composition comprises kanamycin at a concentration of ≤50 ng/mL.
36. The pharmaceutical composition of embodiment 27, wherein the composition comprises triton X-100 at a concentration of ≤250 ng/mL.
37. The pharmaceutical composition of embodiment 27, wherein the composition comprises protein L at a concentration of ≤1 ng/mL.
38. The pharmaceutical composition of embodiment 27, wherein the composition comprises protein L at a concentration of ≤0.025 ng/mL.
39. The pharmaceutical composition of embodiment 27, wherein the composition comprises glucan at a concentration of ≤1 ng/mL.
40. The pharmaceutical composition of any one of embodiments 1-39, wherein the pharmaceutical composition is diluted with 5% dextrose in water.

41. The pharmaceutical composition of any one of embodiments 1-39, wherein the pharmaceutical composition is diluted with 0.9% sodium chloride in water.
42. The pharmaceutical composition of any one of embodiments 1-41, wherein the pharmaceutical composition is substantially stable for at least 3 months at about −10° C. to about −25° C.
43. The pharmaceutical composition of any one of embodiments 1-41, wherein the pharmaceutical composition is substantially stable for at least 3 months at about 2° C. to about 8° C.
44. The pharmaceutical composition of any one of embodiments 1-41, wherein the pharmaceutical composition is substantially stable after two freeze/thaw cycles.
45. The pharmaceutical composition of any one of embodiments 1-41, wherein the pharmaceutical composition is substantially stable for at least 24 hours at room temperature.
46. The pharmaceutical composition of embodiment 22, wherein the pharmaceutical composition further comprises a salt selected from sodium chloride and arginine.
47. A method for treating or slowing the progression of a solid tumor, the method comprising administering to a subject in need thereof an effective amount of the pharmaceutical composition of any one of embodiments 1-46.
48. The method of embodiment 47, wherein the solid tumor expresses PD-L1.
49. A method for treating or slowing the progression of a solid tumor, the method comprising administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose of about 1 μg/kg to about 200 μg/kg of the subject's body weight.
50. The method of embodiment 49, wherein the solid tumor expresses PD-L1.
51. The method of embodiment 49 or 50, wherein the PD-L1 biding molecule is administered at a dose of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight.
52. The method of 49 or 50, wherein the PD-L1 binding molecule is administered at a dose of about 16 μg/kg of the subject's body weight.
53. The method of any one of embodiments 49-50, wherein the PD-L1 binding molecule is administered weekly during a first 28-day cycle, wherein the PD-L1 binding molecule is administered on days 1, 8, 15, and 22 of the first 28-day cycle.
54. The method of any one of embodiments 49-50, wherein the PD-L1 binding molecule is administered two times during a first 28-day cycle, wherein the PD-L1 binding molecule is administered on days 1 and 15 of the first 28-day cycle.
55. The method of any one of embodiments 49-50, wherein the PD-L1 binding molecule is administered three times during a first 28-day cycle, wherein the PD-L1 binding molecule is administered on days 1, 8, and 15 of the first 28-day cycle.
56. The method of any one of embodiments 53-55, further comprising administering the PD-L1 binding molecule weekly during a second 28-day cycle following the first 28-day cycle, wherein the PD-L1 binding molecule is administered on days 1, 8, 15, and 22 of the second 28-day cycle.

57. The method of any one of embodiments 53-55, wherein the PD-L1 binding molecule is administered two times during a second 28-day cycle following the first 28-day cycle, wherein the PD-L1 binding molecule is administered on days 1 and 15 of the second 28-day cycle.
58. The method of any one of embodiments 53-55, wherein the PD-L1 binding molecule is administered three times during a second 28-day cycle, wherein the PD-L1 binding molecule is administered on days 1, 8, and 15 of the second 28-day cycle.
59. The method of any one of embodiments 56-58, wherein the PD-L1 binding molecule is administered at a dose of about 1 μg/kg to about 200 μg/kg of the subject's body weight during the second 28-day cycle.
60. The method of any one of embodiments 56-58, wherein the PD-L1 binding molecule is administered at a dose of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight during the second 28-day cycle.
61. The method of any one of embodiments 56-58, wherein the PD-L1 binding molecule is administered at a dose of about 16 μg/kg of the subject's body weight during the second 28-day cycle.
62. The method of any one of embodiments 56-61, further comprising administering the PD-L1 binding molecule weekly during a third 28-day cycle following the first and second 28-day cycles, wherein the PD-L1 binding molecule is administered on days 1, 8, 15, and 22 of the third 28-day cycle.
63. The method of any one of embodiments 56-61, wherein the PD-L1 binding molecule is administered two times during a third 28-day cycle following the first and second 28-day cycles, wherein the PD-L1 binding molecule is administered on days 1 and 15 of the third 28-day cycle.
64. The method of any one of embodiments 56-61, wherein the PD-L1 binding molecule is administered three times during a third 28-day cycle following the first and second 28-day cycles, wherein the PD-L1 binding molecule is administered on days 1, 8, and 15 of the third 28-day cycle.
65. The method of any one of embodiments 62-64, wherein the PD-L1 binding molecule is administered at a dose of about 1 μg/kg to about 200 μg/kg of the subject's body weight during the third 28-day cycle.
66. The method of any one of embodiments 62-64, wherein the PD-L1 binding molecule is administered at a dose of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight during the third 28-day cycle.
67. The method of any one of embodiments 62-64, wherein the PD-L1 binding molecule is administered at a dose of about 16 μg/kg of the subject's body weight during the third 28-day cycle.
68. The method of any one of embodiments 62-67, further comprising administering the PD-L1 binding molecule for at least one additional 28-day cycle.
69. The method of embodiment 68, wherein the PD-L1 binding molecule is administered at a dose of about 1

μg/kg to about 200 μg/kg of the subject's body weight during the at least one additional 28-day cycle.

70. The method of embodiment 68, wherein the PD-L1 binding molecule is administered at a dose of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight during the at least one additional 28-day cycle.
71. The method of embodiment 68, wherein the PD-L1 binding molecule is administered at a dose of about 16 μg/kg of the subject's body weight during the at least one additional 28-day cycle.
72. The method of any one of embodiments 53-71, wherein the dose of the PD-L1 binding molecule administered to the subject over one or more cycles is about 5 mg to about 100 mg.
73. The method of any one of embodiments 53-72, wherein the PD-L1 binding molecule is administered by intravenous infusion.
74. The method of embodiment 73, wherein the intravenous infusion is over about 5 minutes to about 120 minutes.
75. The method of embodiment 74, wherein the intravenous infusion is over about 30 minutes.
76. The method of any one of embodiments 49-75, wherein the solid tumor is squamous cell carcinoma of the head and neck.
77. The method of any one of embodiments 49-75, wherein the solid tumor is non-small cell lung cancer.
78. The method of any one of embodiments 49-77, wherein the solid tumor is unresectable, locally advanced, or metastatic.
79. The method of any one of embodiments 49-78, wherein the cancer is relapsed or refractory to treatment with at least one additional anti-cancer therapy.
80. The method of embodiment 79, wherein the cancer is relapsed or refractory to treatment with at least one of ipilimumab, nivolumab, pembrolizumab, atezolizumab, durvalumab, avelumab, tremelimumab or cemiplimab.
81. The method of embodiment 79, wherein the cancer is relapsed or refractory to a platinum-based therapy.
82. A method for treating or slowing the progression of non-small cell lung cancer, the method comprising administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight.
83. The method of embodiment 82, wherein the PD-L1 binding molecule is administered at a dose of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight.
84. The method of embodiment 82, wherein the non-small cell lung cancer expresses PD-L1.
85. A method for treating or slowing the progression of squamous cell carcinoma of the head and neck, the method comprising administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight.
86. The method of embodiment 85, wherein the PD-L1 binding molecule is administered at a dose in the range of about 8 μg/kg, about 10 μg/kg, about 16 μg/kg, about 20 μg/kg, about 25 μg/kg, about 30 μg/kg, about 40 μg/kg, about 50 μg/kg, or about 75 μg/kg of the subject's body weight.
87. The method of embodiment 85, wherein the non-small cell lung cancer expresses PD-L1.
88. A method for treating or slowing the progression of a solid tumor that expresses PD-L1, the method comprising administering to a subject in need thereof an effective amount of a PD-L 1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight.
89. A method of treating or slowing the progression of a solid tumor that expresses PD-L1, the method comprising screening the subject for an HLA:A*02 haplotype and treating the subject that is positive for the HLA:A*02 haplotype with a PD-L1 binding molecule comprising a polypeptide having the sequence of SEQ ID NO: 1; wherein the PD-L1 binding molecule is administered at a dose in the range of about 1 μg/kg to about 200 μg/kg of the subject's body weight.
90. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor.
91. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor; and wherein prior to administration of the PD-L1 binding molecule, the subject is screened for an HLA:A*02 haplotype.
92. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor; and wherein prior to administration of the PD-L1 binding molecule, the subject is screened for an HLA:A*02 haplotype.

93. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, PD-L1 expression is detected on cells isolated or derived from the solid tumor.
94. The method of embodiment 93, wherein the prior to administration of the PD-L1 binding molecule, the subject is screened for an HLA:A*02 haplotype.
95. The method of embodiment 93 or 94, wherein prior to administration of the PD-L1 binding molecule, the subject is screened for CMV.
96. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1; wherein the PD-L1 binding molecule is administered at a dose in the range of about 1 μg/kg to about 200 μg/kg of the subject's body weight; and wherein prior to administration of the PD-L1 binding molecule, the subject is screened for CMV.
97. The method of embodiment 96, wherein the prior to administration of the PD-L1 binding molecule, the subject is screened for an HLA:A*02 haplotype.
98. The method of embodiment 96 or 97, wherein prior to administration of the PD-L1 binding molecule, PD-L1 expression is detected on cells isolated or derived from the solid tumor.
99. A kit for detecting PD-L1 expression in a sample from a subject.
100. The kit of embodiment 99, wherein the kit comprises: (i) one or more PCR primers capable of amplifying a nucleic acid sequence encoding PD-L1; (ii) one or more antibodies that specifically bind to PD-L1; or (iii) a PD-L1 binding molecule of SEQ ID NO: 1.
101. The kit of embodiment 99 or 100, wherein the sample is isolated or derived from the subject's solid tumor.
102. A kit for detecting an HLA:A*02 haplotype in a sample from a subject.
103. The kit of embodiment 102, wherein the kit comprises: (i) one or more PCR primers capable of amplifying the HLA-A*02 gene or the B2M locus; or (ii) one or more antibodies capable of recognizing the HLA:A*02 haplotype.
104. The kit of embodiment 102 or 103, wherein the kit comprises one or more antibodies that specifically bind to the alpha-2 domain of the HLA-A alpha-chain.
105. The kit of any one of embodiments 102-104, wherein the sample is isolated or derived from the subject's solid tumor.
106. A method for determining whether a subject would be responsive to treatment with the PD-L1 binding molecule of SEQ ID NO: 1, the method comprising using the kit of any one of embodiments 95-97 to detect PD-L1 expression in a sample from the subject.
107. The method of embodiment 106, wherein detection of PD-L1 expression in the sample from the subject indicates that the subject would be responsive to treatment with the PD-L1 binding molecule of SEQ ID NO: 1.
108. A method for determining whether a subject would be responsive to treatment with the PD-L1 binding molecule of SEQ ID NO: 1, the method comprising using the kit of any one of embodiments 98-101 to detect an HLA:A*02 haplotype in a sample from a subject.
109. The method of embodiment 108, wherein detection of the HLA:A*02 haplotype in the sample from the subject indicates that the subject would be responsive to treatment with the PD-L1 binding molecule of SEQ ID NO: 1.

What is claimed is:

1. A method for treating or slowing the progression of a solid tumor, the method comprising administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose of about 50 μg/kg, about 63 μg/kg, about 75 μg/kg, about 80 μg/kg, or about 85 μg/kg 1 μg/kg to about 200 μg/kg of the subject's body weight.

2. The method of claim 1, wherein the solid tumor expresses PD-L1.

3. The method of claim 1, wherein the PD-L1 binding molecule is administered weekly during a first 28-day cycle, wherein the PD-L1 binding molecule is administered on days 1, 8, 15, and 22 of the first 28-day cycle.

4. The method of claim 1, wherein the PD-L1 binding molecule is administered two times during a first 28-day cycle, wherein the PD-L1 binding molecule is administered on days 1 and 15 of the first 28-day cycle.

5. The method of claim 1, wherein the PD-L1 binding molecule is administered three times during a first 28-day cycle, wherein the PD-L1 binding molecule is administered on days 1, 8, and 15 of the first 28-day cycle.

6. The method of claim 3, further comprising administering the PD-L1 binding molecule weekly during a second 28-day cycle following the first 28-day cycle, wherein the PD-L1 binding molecule is administered on days 1, 8, 15, and 22 of the second 28-day cycle.

7. The method of claim 3, wherein the PD-L1 binding molecule is administered two times during a second 28-day cycle following the first 28-day cycle, wherein the PD-L1 binding molecule is administered on days 1 and 15 of the second 28-day cycle.

8. The method of claim 3, wherein the PD-L1 binding molecule is administered three times during a second 28-day cycle, wherein the PD-L1 binding molecule is administered on days 1, 8, and 15 of the second 28-day cycle.

9. The method of claim 6, wherein the PD-L1 binding molecule is administered at a dose of about 50 μg/kg, about 63 μg/kg, about 75 μg/kg, about 80 μg/kg, or about 85 μg/kg, about 90 μg/kg, about 95 μg/kg, about 100 μg/kg, about 125 #g/kg, or about 150 μg/kg of the subject's body weight during the second 28-day cycle.

10. The method of claim 6, further comprising administering the PD-L1 binding molecule weekly during a third 28-day cycle following the first and second 28-day cycles, wherein the PD-L1 binding molecule is administered on days 1, 8, 15, and 22 of the third 28-day cycle.

11. The method of claim 6, wherein the PD-L1 binding molecule is administered two times during a third 28-day cycle following the first and second 28-day cycles, wherein the PD-L1 binding molecule is administered on days 1 and 15 of the third 28-day cycle.

12. The method of claim 6, wherein the PD-L1 binding molecule is administered three times during a third 28-day cycle following the first and second 28-day cycles, wherein the PD-L1 binding molecule is administered on days 1, 8, and 15 of the third 28-day cycle.

13. The method of claim 10, wherein the PD-L1 binding molecule is administered at a dose of about 50 μg/kg, about 63 μg/kg, about 75 μg/kg, about 80 μg/kg, or about 85 μg/kg of the subject's body weight during the third 28-day cycle.

14. The method of claim 10, further comprising administering the PD-L1 binding molecule for at least one additional 28-day cycle.

15. The method of claim 14, wherein the PD-L1 binding molecule is administered at a dose of about 50 μg/kg, about 63 μg/kg, about 75 μg/kg, about 80 μg/kg, or about 85 μg/kg of the subject's body weight during the at least one additional 28-day cycle.

16. The method of claim 3, wherein the dose of the PD-L1 binding molecule administered to the subject over one or more cycles is about 5 mg to about 100 mg.

17. The method of claim 3, wherein the PD-L1 binding molecule is administered by intravenous infusion.

18. The method of claim 17, wherein the intravenous infusion is over about 5 minutes to about 120 minutes.

19. The method of claim 18, wherein the intravenous infusion is over about 30 minutes.

20. The method of claim 1, wherein the solid tumor is squamous cell carcinoma of the head and neck.

21. The method of claim 1, wherein the solid tumor is non-small cell lung cancer.

22. The method of claim 1, wherein the solid tumor is unresectable, locally advanced, or metastatic.

23. The method of claim 1, wherein the cancer is relapsed or refractory to treatment with at least one additional anti-cancer therapy.

24. The method of claim 23, wherein the cancer is relapsed or refractory to treatment with at least one of ipilimumab, nivolumab, pembrolizumab, atezolizumab, durvalumab, avelumab, tremelimumab or cemiplimab.

25. The method of claim 23, wherein the cancer is relapsed or refractory to a platinum-based therapy.

26. A method for treating or slowing the progression of non-small cell lung cancer, the method comprising administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose in the range of about 50 μg/kg, about 63 μg/kg, about 75 μg/kg, about 80 μg/kg, or about 85 μg/kg of the subject's body weight.

27. The method of claim 26, wherein the non-small cell lung cancer expresses PD-L1.

28. A method for treating or slowing the progression of squamous cell carcinoma of the head and neck, the method comprising administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose in the range of about 50 μg/kg, about 63 μg/kg, about 75 μg/kg, about 80 μg/kg, or about 85 μg/kg of the subject's body weight.

29. The method of claim 28, wherein the squamous cell carcinoma of the head and neck expresses PD-L1.

30. A method for treating or slowing the progression of a solid tumor that expresses PD-L1, the method comprising administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose in the range of about 50 μg/kg, about 63 μg/kg, about 75 μg/kg, about 80 μg/kg, or about 85 μg/kg of the subject's body weight.

31. A method of treating or slowing the progression of a solid tumor that expresses PD-L1, the method comprising screening the subject for an HLA: A*02 haplotype and treating the subject that is positive for the HLA: A*02 haplotype with a PD-L1 binding molecule comprising a polypeptide having the sequence of SEQ ID NO: 1;

wherein the PD-L1 binding molecule is administered at a dose in the range of about 50 μg/kg, about 63 μg/kg, about 75 μg/kg, about 80 μg/kg, or about 85 μg/kg of the subject's body weight.

32. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose in the range of about 50 μg/kg, about 63 μg/kg, about 75 μg/kg, about 80 μg/kg, or about 85 μg/kg of the subject's body weight; and/or wherein prior to administration of the PD-L1 binding molecule, PD-L1 expression is detected on cells isolated or derived from the solid tumor; and/or wherein prior to administration of the PD-L1 binding molecule, the subject is screened for an HLA: A*02 haplotype.

33. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose in the range of about 50 μg/kg, about 63 μg/kg, about 75 μg/kg, about 80 μg/kg, or about 85 μg/kg of the subject's body weight; and wherein prior to administration of the PD-L1 binding molecule, PD-L1 expression is detected on cells isolated or derived from the solid tumor.

34. The method of claim 33, wherein prior to administration of the PD-L1 binding molecule, the subject is screened for an HLA: A*02 haplotype or the subject is screened for cytomegalovirus (CMV).

35. A method of treating or slowing the progression of a solid tumor, wherein the method comprises administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose in the range of about 50 μg/kg, about 63 μg/kg, about 75 μg/kg, about 80 μg/kg, or about 85 μg/kg 1 μg/kg to about 200 #g/kg of the subject's body weight; and wherein prior to administration of the PD-L1 binding molecule, the subject is screened for CMV.

36. The method of claim 35, wherein prior to administration of the PD-L1 binding molecule, the subject is screened for an HLA: A*02 haplotype or PD-L1 expression is detected on cells isolated or derived from the solid tumor.

37. The method of claim 1, wherein the PD-L1 binding molecule is administered at a dose of about 63 μg/kg of the subject's body weight.

38. The method of claim 1, A method for treating or slowing the progression of a solid tumor, the method comprising administering to a subject in need thereof an effective amount of a PD-L1 binding molecule, wherein the PD-L1 binding molecule comprises a polypeptide having the sequence of SEQ ID NO: 1;

wherein the PD-L1 binding molecule is administered at a dose of about 83 μg/kg of the subject's body weight.

39. The method of claim 26, wherein the PD-L1 binding molecule is administered at a dose of about 63 μg/kg of the subject's body weight.

40. The method of claim 28, wherein the PD-L1 binding molecule is administered at a dose of about 63 μg/kg of the subject's body weight.

41. The method of claim 3, wherein the dose of the PD-L1 binding molecule administered to the subject over the first 28-day cycle is about 1 mg.

* * * * *

```
                         SEQUENCE LISTING


<160> NUMBER OF SEQ ID NOS: 39

<210> SEQ ID NO 1
<211> LENGTH: 514
<212> TYPE: PRT
<213> ORGANISM: Artificial Sequence
<220> FEATURE:
<223> OTHER INFORMATION: PD-L1-binding molecule

<400> SEQUENCE: 1

Met Lys Glu Phe Thr Leu Asp Phe Ser Thr Ala Lys Thr Tyr Val Asp
1               5                   10                  15

Ser Leu Asn Val Ile Arg Ser Ala Ile Gly Thr Pro Leu Gln Thr Ile
            20                  25                  30

Ser Ser Gly Gly Thr Ser Leu Leu Met Ile Asp Ser Gly Ile Gly Asp
        35                  40                  45

Asn Leu Phe Ala Val Asp Ile Leu Gly Phe Asp Phe Thr Leu Gly Arg
    50                  55                  60

Phe Asn Asn Leu Arg Leu Ile Val Glu Arg Asn Asn Leu Tyr Val Thr
65                  70                  75                  80

Gly Phe Val Asn Arg Thr Asn Asn Val Phe Tyr Arg Phe Ala Asp Phe
                85                  90                  95
```

-continued

```
Ser His Val Thr Phe Pro Gly Thr Thr Ala Val Thr Leu Ser Ala Asp
            100                 105                 110

Ser Ser Tyr Thr Thr Leu Gln Arg Val Ala Gly Ile Ser Arg Thr Gly
        115                 120                 125

Met Gln Ile Asn Arg His Ser Leu Thr Thr Ser Tyr Leu Asp Leu Met
    130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Ala Ser Tyr Val
            180                 185                 190

Met Thr Ala Glu Asp Val Asp Leu Thr Leu Asn Trp Gly Arg Leu Ser
        195                 200                 205

Ser Val Leu Pro Asp Tyr His Gly Gln Asp Ser Val Arg Val Gly Arg
    210                 215                 220

Ile Ser Phe Gly Ser Ile Asn Ala Ile Leu Gly Ser Val Ala Leu Ile
225                 230                 235                 240

Leu Asn Ser His His His Ala Ser Ala Val Ala Ala Glu Phe Pro Lys
                245                 250                 255

Pro Ser Thr Pro Pro Gly Ser Ser Gly Gly Ala Pro Glu Val Gln Leu
            260                 265                 270

Gln Gln Ser Gly Pro Glu Leu Val Lys Pro Gly Ala Ser Val Lys Ile
        275                 280                 285

Ser Cys Lys Thr Ser Gly Tyr Thr Phe Thr Glu Tyr Thr Met His Trp
    290                 295                 300

Val Lys Gln Arg His Gly Lys Ser Leu Glu Trp Ile Gly Gly Ile Asn
305                 310                 315                 320

Pro Asn Asn Gly Gly Thr Trp Tyr Asn Gln Lys Phe Lys Gly Lys Ala
                325                 330                 335

Thr Leu Thr Val Asp Lys Ser Ser Ser Thr Ala Tyr Met Glu Leu Arg
            340                 345                 350

Ser Leu Thr Ser Glu Asp Ser Ala Val Tyr Phe Cys Ala Arg Pro Tyr
        355                 360                 365

Tyr Tyr Gly Ser Arg Glu Asp Tyr Phe Asp Tyr Trp Gly Gln Gly Thr
    370                 375                 380

Thr Leu Thr Val Ser Ser Gly Gly Gly Gly Ser Asp Ile Gln Met Thr
385                 390                 395                 400

Gln Ser Pro Ser Ser Leu Ser Ala Ser Val Gly Asp Arg Val Thr Ile
                405                 410                 415

Thr Cys Ser Ala Ser Ser Ser Val Ser Tyr Met Tyr Trp Tyr Gln Gln
            420                 425                 430

Lys Pro Arg Ser Ser Pro Lys Pro Trp Ile Tyr Leu Thr Ser Asn Leu
        435                 440                 445

Ala Ser Gly Val Pro Ala Arg Phe Ser Gly Ser Gly Ser Gly Thr Ser
    450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Pro Thr Phe Gly Gly Gly Thr
                485                 490                 495
```

```
Lys Leu Glu Leu Lys His His Ala Ala Asn Leu Val Pro Met Val Ala
            500                 505                 510

Thr Val


<210> SEQ ID NO 2
<211> LENGTH: 233
<212> TYPE: PRT
<213> ORGANISM: Artificial Sequence
<220> FEATURE:
<223> OTHER INFORMATION: anti-PD-L1 scFv

<400> SEQUENCE: 2

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45

Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Tyr Gly Ser Arg Glu Asp Tyr Phe Asp Tyr Trp
            100                 105                 110

Gly Gln Gly Thr Thr Leu Thr Val Ser Ser Gly Gly Gly Gly Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Ser Ala Ser Ser Ser Val Ser Tyr Met Tyr
145                 150                 155                 160

Trp Tyr Gln Gln Lys Pro Arg Ser Ser Pro Lys Pro Trp Ile Tyr Leu
                165                 170                 175

Thr Ser Asn Leu Ala Ser Gly Val Pro Ala Arg Phe Ser Gly Ser Gly
            180                 185                 190

Ser Gly Thr Ser Tyr Ser Leu Thr Ile Ser Ser Met Glu Ala Glu Asp
        195                 200                 205

Ala Ala Thr Tyr Tyr Cys Gln Gln Trp Ser Ser Asn Pro Pro Thr Phe
    210                 215                 220

Gly Gly Gly Thr Lys Leu Glu Leu Lys
225                 230


<210> SEQ ID NO 3
<211> LENGTH: 122
<212> TYPE: PRT
<213> ORGANISM: Artificial Sequence
<220> FEATURE:
<223> OTHER INFORMATION: VH domain

<400> SEQUENCE: 3

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Arg His Gly Lys Ser Leu Glu Trp Ile
        35                  40                  45
```

```
Gly Gly Ile Asn Pro Asn Asn Gly Gly Thr Trp Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Pro Tyr Tyr Tyr Gly Ser Arg Glu Asp Tyr Phe Asp Tyr Trp
            100                 105                 110

Gly Gln Gly Thr Thr Leu Thr Val Ser Ser
        115                 120


<210> SEQ ID NO 4
<211> LENGTH: 106
<212> TYPE: PRT
<213> ORGANISM: Artificial Sequence
<220> FEATURE:
<223> OTHER INFORMATION: VL domain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Leu Lys
            100                 105


<210> SEQ ID NO 5
<211> LENGTH: 5
<212> TYPE: PRT
<213> ORGANISM: Artificial Sequence
<220> FEATURE:
<223> OTHER INFORMATION: HCDR1

<400> SEQUENCE: 5

Glu Tyr Thr Met His
1               5


<210> SEQ ID NO 6
<211> LENGTH: 16
<212> TYPE: PRT
<213> ORGANISM: Artificial Sequence
<220> FEATURE:
<223> OTHER INFORMATION: HCDR2

<400> SEQUENCE: 6

Gly Ile Asn Pro Asn Asn Gly Gly Thr Trp Tyr Asn Gln Lys Phe Lys
1               5                   10                  15


<210> SEQ ID NO 7
<211> LENGTH: 13
<212> TYPE: PRT
<213> ORGANISM: Artificial Sequence
<220> FEATURE:
```

-continued

```
<223> OTHER INFORMATION: HCDR3

<400> SEQUENCE: 7

Pro Tyr Tyr Tyr Gly Ser Arg Glu Asp Tyr Phe Asp Tyr
1               5                   10


<210> SEQ ID NO 8
<211> LENGTH: 10
<212> TYPE: PRT
<213> ORGANISM: Artificial Sequence
<220> FEATURE:
<223> OTHER INFORMATION: LCDR1

<400> SEQUENCE: 8

Ser Ala Ser Ser Ser Val Ser Tyr Met Tyr
1               5                   10


<210> SEQ ID NO 9
<211> LENGTH: 7
<212> TYPE: PRT
<213> ORGANISM: Artificial Sequence
<220> FEATURE:
<223> OTHER INFORMATION: LCDR2

<400> SEQUENCE: 9

Leu Thr Ser Asn Leu Ala Ser
1               5


<210> SEQ ID NO 10
<211> LENGTH: 9
<212> TYPE: PRT
<213> ORGANISM: Artificial Sequence
<220> FEATURE:
<223> OTHER INFORMATION: LCDR3

<400> SEQUENCE: 10

Gln Gln Trp Ser Ser Asn Pro Pro Thr
1               5


<210> SEQ ID NO 11
<211> LENGTH: 5
<212> TYPE: PRT
<213> ORGANISM: Artificial Sequence
<220> FEATURE:
<223> OTHER INFORMATION: scFv linker

<400> SEQUENCE: 11

Gly Gly Gly Gly Ser
1               5


<210> SEQ ID NO 12
<211> LENGTH: 251
<212> TYPE: PRT
<213> ORGANISM: Artificial Sequence
<220> FEATURE:
<223> OTHER INFORMATION: Shiga Toxin subunit effector

<400> SEQUENCE: 12

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Gly Asp Asn
        35                  40                  45
```

-continued

```
Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Ala Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Ala Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ala Ser Ala Val Ala Ala
                245                 250


<210> SEQ ID NO 13
<211> LENGTH: 16
<212> TYPE: PRT
<213> ORGANISM: Artificial Sequence
<220> FEATURE:
<223> OTHER INFORMATION: Binding domain linker

<400> SEQUENCE: 13

Glu Phe Pro Lys Pro Ser Thr Pro Pro Gly Ser Ser Gly Gly Ala Pro
1               5                   10                  15


<210> SEQ ID NO 14
<211> LENGTH: 4
<212> TYPE: PRT
<213> ORGANISM: Artificial Sequence
<220> FEATURE:
<223> OTHER INFORMATION: Cleavable Spacer

<400> SEQUENCE: 14

His His Ala Ala
1


<210> SEQ ID NO 15
<211> LENGTH: 9
<212> TYPE: PRT
<213> ORGANISM: Artificial Sequence
<220> FEATURE:
<223> OTHER INFORMATION: T cell epitope

<400> SEQUENCE: 15

Asn Leu Val Pro Met Val Ala Thr Val
1               5
```

<210> SEQ ID NO 16
<211> LENGTH: 9
<212> TYPE: PRT
<213> ORGANISM: Artificial Sequence
<220> FEATURE:
<223> OTHER INFORMATION: T cell epitope

<400> SEQUENCE: 16

Val Thr Glu His Asp Thr Leu Leu Tyr
1               5

<210> SEQ ID NO 17
<211> LENGTH: 9
<212> TYPE: PRT
<213> ORGANISM: Artificial Sequence
<220> FEATURE:
<223> OTHER INFORMATION: T cell epitope

<400> SEQUENCE: 17

Ser Ile Ile Asn Phe Glu Lys Tyr Leu
1               5

<210> SEQ ID NO 18
<211> LENGTH: 9
<212> TYPE: PRT
<213> ORGANISM: Artificial Sequence
<220> FEATURE:
<223> OTHER INFORMATION: T cell epitope

<400> SEQUENCE: 18

Gly Leu Asp Arg Asn Ser Gly Asn Tyr
1               5

<210> SEQ ID NO 19
<211> LENGTH: 9
<212> TYPE: PRT
<213> ORGANISM: Artificial Sequence
<220> FEATURE:
<223> OTHER INFORMATION: T cell epitope

<400> SEQUENCE: 19

Gly Val Met Thr Arg Gly Arg Leu Lys
1               5

<210> SEQ ID NO 20
<211> LENGTH: 9
<212> TYPE: PRT
<213> ORGANISM: Artificial Sequence
<220> FEATURE:
<223> OTHER INFORMATION: T cell epitope

<400> SEQUENCE: 20

Gly Ile Leu Gly Phe Val Phe Thr Leu
1               5

<210> SEQ ID NO 21
<211> LENGTH: 9
<212> TYPE: PRT
<213> ORGANISM: Artificial Sequence
<220> FEATURE:
<223> OTHER INFORMATION: T cell epitope

<400> SEQUENCE: 21

Ile Leu Arg Gly Ser Val Ala His Lys
1               5

<210> SEQ ID NO 22
<211> LENGTH: 12
<212> TYPE: PRT
<213> ORGANISM: Artificial Sequence
<220> FEATURE:
<223> OTHER INFORMATION: Linker

<400> SEQUENCE: 22

```
Gly Lys Ser Ser Gly Ser Gly Ser Glu Ser Lys Ser
1               5                   10
```

<210> SEQ ID NO 23
<211> LENGTH: 14
<212> TYPE: PRT
<213> ORGANISM: Artificial Sequence
<220> FEATURE:
<223> OTHER INFORMATION: Linker

<400> SEQUENCE: 23

```
Glu Gly Lys Ser Ser Gly Ser Gly Ser Glu Ser Lys Glu Phe
1               5                   10
```

<210> SEQ ID NO 24
<211> LENGTH: 14
<212> TYPE: PRT
<213> ORGANISM: Artificial Sequence
<220> FEATURE:
<223> OTHER INFORMATION: Linker

<400> SEQUENCE: 24

```
Gly Ser Thr Ser Gly Ser Gly Lys Ser Ser Glu Gly Lys Gly
1               5                   10
```

<210> SEQ ID NO 25
<211> LENGTH: 18
<212> TYPE: PRT
<213> ORGANISM: Artificial Sequence
<220> FEATURE:
<223> OTHER INFORMATION: Linker

<400> SEQUENCE: 25

```
Gly Ser Thr Ser Gly Ser Gly Lys Ser Ser Glu Gly Ser Gly Ser Thr
1               5                   10                  15

Lys Gly
```

<210> SEQ ID NO 26
<211> LENGTH: 18
<212> TYPE: PRT
<213> ORGANISM: Artificial Sequence
<220> FEATURE:
<223> OTHER INFORMATION: Linker

<400> SEQUENCE: 26

```
Gly Ser Thr Ser Gly Ser Gly Lys Pro Gly Ser Gly Glu Gly Ser Thr
1               5                   10                  15

Lys Gly
```

<210> SEQ ID NO 27
<211> LENGTH: 5
<212> TYPE: PRT
<213> ORGANISM: Artificial Sequence
<220> FEATURE:
<223> OTHER INFORMATION: Linker

<400> SEQUENCE: 27

Ser Arg Ser Ser Gly
1 5

<210> SEQ ID NO 28
<211> LENGTH: 5
<212> TYPE: PRT
<213> ORGANISM: Artificial Sequence
<220> FEATURE:
<223> OTHER INFORMATION: Linker

<400> SEQUENCE: 28

Ser Gly Ser Ser Cys
1 5

<210> SEQ ID NO 29
<211> LENGTH: 15
<212> TYPE: PRT
<213> ORGANISM: Artificial Sequence
<220> FEATURE:
<223> OTHER INFORMATION: Linker

<400> SEQUENCE: 29

Gly Ser Thr Ser Gly Ser Gly Lys Pro Gly Ser Gly Glu Gly Ser
1 5 10 15

<210> SEQ ID NO 30
<211> LENGTH: 16
<212> TYPE: PRT
<213> ORGANISM: Artificial Sequence
<220> FEATURE:
<223> OTHER INFORMATION: Linker

<400> SEQUENCE: 30

Glu Phe Pro Lys Pro Ser Thr Pro Pro Gly Ser Ser Gly Gly Ala Pro
1 5 10 15

<210> SEQ ID NO 31
<211> LENGTH: 4
<212> TYPE: PRT
<213> ORGANISM: Artificial Sequence
<220> FEATURE:
<223> OTHER INFORMATION: Linker

<400> SEQUENCE: 31

Gly Gly Gly Ser
1

<210> SEQ ID NO 32
<211> LENGTH: 8
<212> TYPE: PRT
<213> ORGANISM: Artificial Sequence
<220> FEATURE:
<223> OTHER INFORMATION: Linker

<400> SEQUENCE: 32

Gly Gly Gly Gly Ser Gly Gly Gly
1 5

<210> SEQ ID NO 33
<211> LENGTH: 7
<212> TYPE: PRT
<213> ORGANISM: Artificial Sequence
<220> FEATURE:
<223> OTHER INFORMATION: Linker

<400> SEQUENCE: 33

Gly Gly Ser Gly Gly Gly Gly
1 5

<210> SEQ ID NO 34
<211> LENGTH: 18
<212> TYPE: PRT
<213> ORGANISM: Artificial Sequence
<220> FEATURE:
<223> OTHER INFORMATION: Linker

<400> SEQUENCE: 34

Gly Ser Thr Ser Gly Gly Gly Ser Gly Gly Gly Ser Gly Gly Gly Gly
1 5 10 15

Ser Ser

<210> SEQ ID NO 35
<211> LENGTH: 18
<212> TYPE: PRT
<213> ORGANISM: Artificial Sequence
<220> FEATURE:
<223> OTHER INFORMATION: Linker

<400> SEQUENCE: 35

Gly Ser Thr Ser Gly Ser Gly Lys Pro Gly Ser Ser Glu Gly Ser Thr
1 5 10 15

Lys Gly

<210> SEQ ID NO 36
<211> LENGTH: 4
<212> TYPE: PRT
<213> ORGANISM: Artificial Sequence
<220> FEATURE:
<223> OTHER INFORMATION: Furin-cleavage motif
<220> FEATURE:
<221> NAME/KEY: SITE
<222> LOCATION: (2)..(3)
<223> OTHER INFORMATION: Xaa is any amino acid

<400> SEQUENCE: 36

Arg Xaa Xaa Arg
1

<210> SEQ ID NO 37
<211> LENGTH: 293
<212> TYPE: PRT
<213> ORGANISM: Artificial Sequence
<220> FEATURE:
<223> OTHER INFORMATION: SLT-1A

<400> SEQUENCE: 37

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Ser Gly Asp Asn
35 40 45

Leu Phe Ala Val Asp Val Arg Gly Ile Asp Pro Glu Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Gly Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Gly Thr Ser Leu Thr Gln Ser Val Ala Arg Ala Met Leu Arg
145 150 155 160

Phe Val Thr Val Thr Ala Glu Ala Leu Arg Phe Arg Gln Ile Gln Arg
165 170 175

Gly Phe Arg Thr Thr Leu Asp Asp Leu Ser Gly Arg Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg Met Ala Ser Asp Glu
245 250 255

Phe Pro Ser Met Cys Pro Ala Asp Gly Arg Val Arg Gly Ile Thr His
260 265 270

Asn Lys Ile Leu Trp Asp Ser Ser Thr Leu Gly Ala Ile Leu Met Arg
275 280 285

Arg Thr Ile Ser Ser
290

<210> SEQ ID NO 38
<211> LENGTH: 293
<212> TYPE: PRT
<213> ORGANISM: Artificial Sequence
<220> FEATURE:
<223> OTHER INFORMATION: Stx

<400> SEQUENCE: 38

Lys Glu Phe Thr Leu Asp Phe Ser Thr Ala Lys Thr Tyr Val Asp Ser
1 5 10 15

Leu Asn Val Ile Arg Ser Ala Ile Gly Thr Pro Leu Gln Thr Ile Ser
20 25 30

Ser Gly Gly Thr Ser Leu Leu Met Ile Asp Ser Gly Thr Gly Asp Asn
35 40 45

Leu Phe Ala Val Asp Val Arg Gly Ile Asp Pro Glu Glu Gly Arg Phe
50 55 60

Asn Asn Leu Arg Leu Ile Val Glu Arg Asn Asn Leu Tyr Val Thr Gly
65 70 75 80

Phe Val Asn Arg Thr Asn Asn Val Phe Tyr Arg Phe Ala Asp Phe Ser
85 90 95

His Val Thr Phe Pro Gly Thr Thr Ala Val Thr Leu Ser Gly Asp Ser
100 105 110

Ser Tyr Thr Thr Leu Gln Arg Val Ala Gly Ile Ser Arg Thr Gly Met
115 120 125

Gln Ile Asn Arg His Ser Leu Thr Thr Ser Tyr Leu Asp Leu Met Ser
130 135 140

His Ser Gly Thr Ser Leu Thr Gln Ser Val Ala Arg Ala Met Leu Arg
145 150 155 160

```
Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290


<210> SEQ ID NO 39
<211> LENGTH: 297
<212> TYPE: PRT
<213> ORGANISM: Artificial Sequence
<220> FEATURE:
<223> OTHER INFORMATION: SLT-2A

<400> SEQUENCE: 39

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220
```

-continued

```
Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285

Pro Gln Asp Leu Thr Glu Pro Asn Gln
    290                 295
```